United States Patent
Sato et al.

(10) Patent No.: US 12,258,406 B2
(45) Date of Patent: Mar. 25, 2025

(54) ANTIBODIES THAT BIND CD3 EPSILON

(71) Applicant: Twist Bioscience Corporation, South San Francisco, CA (US)

(72) Inventors: Aaron Sato, Burlingame, CA (US); Qiang Liu, Palo Alto, CA (US); Mary Mathieu, South San Francisco, CA (US); Linya Wang, Milpitas, CA (US)

(73) Assignee: Twist Bioscience Corporation, South San Francisco, CA (US)

( * ) Notice: Subject to any disclaimer, the term of this patent is extended or adjusted under 35 U.S.C. 154(b) by 0 days.

(21) Appl. No.: 17/702,660

(22) Filed: Mar. 23, 2022

(65) Prior Publication Data

US 2022/0348659 A1 Nov. 3, 2022

Related U.S. Application Data

(60) Provisional application No. 63/165,656, filed on Mar. 24, 2021.

(51) Int. Cl.
 *C07K 16/28* (2006.01)
 *C07K 16/18* (2006.01)
 *C12N 15/10* (2006.01)

(52) U.S. Cl.
 CPC .......... *C07K 16/2809* (2013.01); *C07K 16/18* (2013.01); *C12N 15/1068* (2013.01); *C07K 2317/31* (2013.01); *C07K 2317/569* (2013.01); *C07K 2317/622* (2013.01); *C07K 2317/92* (2013.01)

(58) Field of Classification Search
 CPC ............ C07K 16/2809; C07K 2317/56; C07K 2317/92
 USPC ............................................. 424/133.1, 135.1
 See application file for complete search history.

(56) References Cited

U.S. PATENT DOCUMENTS

| | | | |
|---|---|---|---|
| 5,368,823 A | 11/1994 | McGraw et al. | |
| 5,474,796 A | 12/1995 | Brennan | |
| 5,534,507 A | 7/1996 | Cama et al. | |
| 5,677,195 A | 10/1997 | Winkler et al. | |
| 5,843,767 A | 12/1998 | Beattie | |
| 6,013,440 A | 1/2000 | Lipshutz et al. | |
| 6,028,189 A | 2/2000 | Blanchard | |
| 6,419,883 B1 | 7/2002 | Blanchard | |
| 6,472,147 B1 | 10/2002 | Janda et al. | |
| 6,492,107 B1 | 12/2002 | Kauffman et al. | |
| 6,893,816 B1 | 5/2005 | Beattie | |
| 7,163,660 B2 | 1/2007 | Lehmann | |
| 7,202,264 B2 | 4/2007 | Ravikumar et al. | |
| 8,198,071 B2 | 6/2012 | Goshoo et al. | |
| 9,334,331 B2* | 5/2016 | Igawa .................. A61P 7/04 | |
| 9,403,141 B2 | 8/2016 | Banyai et al. | |
| 9,409,139 B2 | 8/2016 | Banyai et al. | |
| 9,555,388 B2 | 1/2017 | Banyai et al. | |
| 9,677,067 B2 | 6/2017 | Toro et al. | |
| 9,745,619 B2 | 8/2017 | Rabbani et al. | |
| 9,765,387 B2 | 9/2017 | Rabbani et al. | |
| 9,833,761 B2 | 12/2017 | Banyai et al. | |
| 9,839,894 B2 | 12/2017 | Banyai et al. | |
| 9,889,423 B2 | 2/2018 | Banyai et al. | |
| 9,895,673 B2 | 2/2018 | Peck et al. | |
| 9,981,239 B2 | 5/2018 | Banyai et al. | |
| 10,053,688 B2 | 8/2018 | Cox | |
| 10,272,410 B2 | 4/2019 | Banyai et al. | |
| 10,384,188 B2 | 8/2019 | Banyai et al. | |
| 10,384,189 B2 | 8/2019 | Peck | |
| 10,417,457 B2 | 9/2019 | Peck | |
| 10,421,807 B2* | 9/2019 | Gonzales ............... A61P 17/08 | |
| 10,583,415 B2 | 3/2020 | Banyai et al. | |
| 10,618,024 B2 | 4/2020 | Banyai et al. | |
| 10,632,445 B2 | 4/2020 | Banyai et al. | |
| 10,639,609 B2 | 5/2020 | Banyai et al. | |
| 10,669,304 B2 | 6/2020 | Indermuhle et al. | |
| 10,744,477 B2 | 8/2020 | Banyai et al. | |
| 10,754,994 B2 | 8/2020 | Peck | |
| 10,773,232 B2 | 9/2020 | Banyai et al. | |
| 10,844,373 B2 | 11/2020 | Cox et al. | |
| 10,894,242 B2 | 1/2021 | Marsh et al. | |
| 10,894,959 B2 | 1/2021 | Cox et al. | |
| 10,907,274 B2 | 2/2021 | Cox | |
| 10,936,953 B2 | 3/2021 | Bramlett et al. | |
| 10,969,965 B2 | 4/2021 | Malina et al. | |
| 10,975,372 B2 | 4/2021 | Cox et al. | |
| 10,987,648 B2 | 4/2021 | Peck et al. | |
| 11,185,837 B2 | 11/2021 | Banyai et al. | |
| 11,214,798 B2 | 1/2022 | Brown | |
| 11,263,354 B2 | 3/2022 | Peck | |
| 11,332,738 B2 | 5/2022 | Nugent et al. | |

(Continued)

FOREIGN PATENT DOCUMENTS

| CN | 101277758 A | 10/2008 |
|---|---|---|
| CN | 106146661 A | 11/2016 |

(Continued)

OTHER PUBLICATIONS

Krah et al. (Immunopharmacology and Immunotoxicology, 38:1, 21-28 (2016)).*

(Continued)

*Primary Examiner* — Lynn A Bristol

(74) *Attorney, Agent, or Firm* — McNeill PLLC

(57) ABSTRACT

Provided herein are methods and compositions relating to CD3 libraries having nucleic acids encoding for a scaffold comprising a CD3 domain. CD3 libraries described herein encode for immunoglobulins such as antibodies.

8 Claims, 39 Drawing Sheets

Specification includes a Sequence Listing.

(56) References Cited

U.S. PATENT DOCUMENTS

| | | |
|---|---|---|
| 11,332,740 B2 | 5/2022 | Nugent et al. |
| 11,377,676 B2 | 7/2022 | Wu et al. |
| 2001/0018512 A1 | 8/2001 | Blanchard |
| 2002/0025561 A1 | 2/2002 | Hodgson |
| 2002/0094533 A1 | 7/2002 | Hess et al. |
| 2002/0095073 A1 | 7/2002 | Jacobs et al. |
| 2002/0160536 A1 | 10/2002 | Regnier et al. |
| 2002/0164824 A1 | 11/2002 | Xiao et al. |
| 2003/0120035 A1 | 6/2003 | Gao et al. |
| 2003/0171325 A1 | 9/2003 | Gascoyne et al. |
| 2004/0087008 A1 | 5/2004 | Schembri |
| 2004/0259146 A1 | 12/2004 | Friend et al. |
| 2005/0049402 A1 | 3/2005 | Babcook et al. |
| 2005/0137805 A1 | 6/2005 | Lewin et al. |
| 2005/0227235 A1 | 10/2005 | Carr et al. |
| 2006/0127920 A1 | 6/2006 | Church et al. |
| 2007/0196834 A1 | 8/2007 | Cerrina et al. |
| 2008/0085511 A1 | 4/2008 | Peck et al. |
| 2008/0085514 A1 | 4/2008 | Peck et al. |
| 2008/0227160 A1 | 9/2008 | Kool |
| 2008/0287320 A1 | 11/2008 | Baynes et al. |
| 2008/0300842 A1 | 12/2008 | Govindarajan et al. |
| 2009/0062129 A1 | 3/2009 | McKernan et al. |
| 2009/0239759 A1 | 9/2009 | Balch |
| 2009/0285825 A1 | 11/2009 | Kini et al. |
| 2010/0004143 A1 | 1/2010 | Shibahara |
| 2010/0099103 A1 | 4/2010 | Hsieh et al. |
| 2010/0111768 A1 | 5/2010 | Banerjee et al. |
| 2010/0216648 A1 | 8/2010 | Staehler et al. |
| 2010/0311960 A1 | 12/2010 | Dellinger |
| 2011/0172127 A1 | 7/2011 | Jacobson et al. |
| 2011/0217738 A1 | 9/2011 | Jacobson |
| 2012/0129704 A1 | 5/2012 | Gunderson et al. |
| 2012/0164691 A1 | 6/2012 | Eshoo et al. |
| 2012/0231968 A1 | 9/2012 | Bruhn et al. |
| 2012/0264653 A1 | 10/2012 | Carr et al. |
| 2013/0017642 A1 | 1/2013 | Milgrew et al. |
| 2013/0017977 A1 | 1/2013 | Oleinikov |
| 2013/0065017 A1 | 3/2013 | Sieber |
| 2013/0109595 A1 | 5/2013 | Routenberg |
| 2013/0109596 A1 | 5/2013 | Peterson et al. |
| 2013/0130321 A1 | 5/2013 | Staehler et al. |
| 2013/0165328 A1 | 6/2013 | Previte et al. |
| 2013/0289246 A1 | 10/2013 | Crowe et al. |
| 2014/0106394 A1 | 4/2014 | Ko et al. |
| 2014/0178992 A1 | 6/2014 | Nakashima et al. |
| 2015/0038373 A1 | 2/2015 | Banyai et al. |
| 2015/0120265 A1 | 4/2015 | Amirav-Drory et al. |
| 2015/0196917 A1 | 7/2015 | Kay et al. |
| 2016/0089651 A1 | 3/2016 | Banyai |
| 2016/0090592 A1 | 3/2016 | Banyai et al. |
| 2016/0096160 A1 | 4/2016 | Banyai et al. |
| 2016/0115241 A1 | 4/2016 | Yan et al. |
| 2016/0251651 A1 | 9/2016 | Banyai et al. |
| 2016/0303535 A1 | 10/2016 | Banyai et al. |
| 2016/0333340 A1 | 11/2016 | Wu |
| 2016/0339409 A1 | 11/2016 | Banyai et al. |
| 2016/0340672 A1 | 11/2016 | Banyai et al. |
| 2016/0354752 A1 | 12/2016 | Banyai et al. |
| 2017/0081716 A1 | 3/2017 | Peck |
| 2017/0095785 A1 | 4/2017 | Banyai et al. |
| 2017/0159044 A1 | 6/2017 | Toro et al. |
| 2017/0174762 A1 | 6/2017 | Zinzalla et al. |
| 2017/0327819 A1 | 11/2017 | Banyai et al. |
| 2017/0357752 A1 | 12/2017 | Diggans |
| 2017/0362589 A1 | 12/2017 | Banyai et al. |
| 2018/0029001 A1 | 2/2018 | Banyai et al. |
| 2018/0104664 A1 | 4/2018 | Fernandez |
| 2018/0142289 A1 | 5/2018 | Zeitoun et al. |
| 2018/0253563 A1 | 9/2018 | Peck et al. |
| 2018/0264428 A1 | 9/2018 | Banyai et al. |
| 2018/0282721 A1 | 10/2018 | Cox et al. |
| 2018/0296668 A1 | 10/2018 | Igawa et al. |
| 2018/0326388 A1 | 11/2018 | Banyai et al. |
| 2019/0135926 A1 | 5/2019 | Glanville |
| 2019/0153432 A1 | 5/2019 | Olson |
| 2019/0314783 A1 | 10/2019 | Banyai et al. |
| 2019/0352635 A1 | 11/2019 | Toro et al. |
| 2019/0366293 A1 | 12/2019 | Banyai et al. |
| 2019/0366294 A1 | 12/2019 | Banyai et al. |
| 2020/0017907 A1 | 1/2020 | Zeitoun et al. |
| 2020/0102611 A1 | 4/2020 | Zeitoun et al. |
| 2020/0156037 A1 | 5/2020 | Banyai et al. |
| 2020/0181667 A1 | 6/2020 | Wu et al. |
| 2020/0222875 A1 | 7/2020 | Peck et al. |
| 2020/0283760 A1 | 9/2020 | Nugent et al. |
| 2020/0299322 A1 | 9/2020 | Indermuhle et al. |
| 2020/0299385 A1 | 9/2020 | Tiefenthaler et al. |
| 2020/0299684 A1 | 9/2020 | Toro et al. |
| 2020/0308575 A1 | 10/2020 | Sato |
| 2020/0325235 A1* | 10/2020 | Tabibiazar ............ C40B 40/08 |
| 2020/0330953 A1 | 10/2020 | Banyai et al. |
| 2021/0002710 A1 | 1/2021 | Gantt et al. |
| 2021/0009691 A1 | 1/2021 | Mach et al. |
| 2021/0040476 A1 | 2/2021 | Cox et al. |
| 2021/0054097 A1* | 2/2021 | Lund ..................... C07K 16/36 |
| 2021/0071168 A1 | 3/2021 | Nugent et al. |
| 2021/0102192 A1 | 4/2021 | Tabibiazar et al. |
| 2021/0102195 A1* | 4/2021 | Sato ...................... C40B 40/08 |
| 2021/0102198 A1 | 4/2021 | Cox et al. |
| 2021/0115594 A1 | 4/2021 | Cox et al. |
| 2021/0129108 A1 | 5/2021 | Marsh et al. |
| 2021/0142182 A1 | 5/2021 | Bramlett et al. |
| 2021/0170356 A1 | 6/2021 | Peck et al. |
| 2021/0179724 A1 | 6/2021 | Sato et al. |
| 2021/0180046 A1 | 6/2021 | Cox et al. |
| 2021/0207197 A1 | 7/2021 | Gantt et al. |
| 2021/0332078 A1 | 10/2021 | Wu |
| 2021/0348220 A1 | 11/2021 | Zeitoun et al. |
| 2021/0355194 A1* | 11/2021 | Sato .................. C07K 16/2896 |
| 2021/0395344 A1 | 12/2021 | Sato et al. |
| 2022/0032256 A1 | 2/2022 | Lackey et al. |
| 2022/0064206 A1 | 3/2022 | Fernandez et al. |
| 2022/0064313 A1* | 3/2022 | Sato ........................ A61P 3/10 |
| 2022/0064628 A1 | 3/2022 | Toro et al. |
| 2022/0106586 A1 | 4/2022 | Nugent et al. |
| 2022/0106590 A1 | 4/2022 | Arbiza et al. |
| 2022/0135690 A1* | 5/2022 | Sato .................. C07K 16/2866 |
| | | 424/133.1 |
| 2022/0135965 A1 | 5/2022 | Gantt et al. |
| 2022/0138354 A1 | 5/2022 | Peck |
| 2022/0145289 A1 | 5/2022 | Lackey et al. |
| 2022/0206001 A1* | 6/2022 | Sato ...................... C07K 16/10 |
| 2022/0243195 A1 | 8/2022 | Nugent et al. |
| 2022/0246236 A1 | 8/2022 | Amirav-Drory |
| 2022/0259319 A1* | 8/2022 | Sato ...................... C07K 16/46 |
| 2022/0259638 A1 | 8/2022 | Brown |
| 2022/0277808 A1 | 9/2022 | Arbiza et al. |
| 2022/0281989 A1 | 9/2022 | Glanville |
| 2022/0307010 A1 | 9/2022 | Sato et al. |
| 2022/0315971 A1 | 10/2022 | Wu et al. |
| 2022/0323924 A1 | 10/2022 | Lackey et al. |
| 2022/0325276 A2 | 10/2022 | Banyai et al. |
| 2022/0325278 A1 | 10/2022 | Nugent et al. |
| 2022/0356463 A1 | 11/2022 | Shen et al. |
| 2022/0356468 A1 | 11/2022 | Sato et al. |
| 2022/0411784 A1 | 12/2022 | Sato et al. |
| 2023/0002478 A1 | 1/2023 | Sato et al. |
| 2023/0054232 A1 | 2/2023 | Peck |
| 2023/0086062 A1 | 3/2023 | Banyai et al. |
| 2023/0096464 A1 | 3/2023 | Sato |
| 2023/0115861 A1 | 4/2023 | Nugent et al. |

FOREIGN PATENT DOCUMENTS

| | | |
|---|---|---|
| EP | 3030682 A2 | 6/2016 |
| JP | H07505530 A | 6/1995 |
| JP | 2001518086 A | 10/2001 |
| JP | 2002538790 A | 11/2002 |
| JP | 2004268394 A | 9/2004 |
| JP | 2006503586 A | 2/2006 |
| JP | 2007314746 A | 12/2007 |
| JP | 2008214343 A | 9/2008 |
| JP | 2009294195 A | 12/2009 |

(56) References Cited

FOREIGN PATENT DOCUMENTS

| | | |
|---|---|---|
| JP | 2012507513 A | 3/2012 |
| JP | 2016527313 A | 9/2016 |
| WO | WO-9320242 A1 | 10/1993 |
| WO | WO-02072791 A2 | 9/2002 |
| WO | WO-2004039953 A2 | 5/2004 |
| WO | 2004106380 A2 | 12/2004 |
| WO | WO-2005059096 A2 | 6/2005 |
| WO | WO-2008054543 A2 | 5/2008 |
| WO | WO-2008063135 A1 | 5/2008 |
| WO | 2008068280 A1 | 6/2008 |
| WO | 2010054007 A1 | 5/2010 |
| WO | WO-2010053443 A1 | 5/2010 |
| WO | WO-2011109031 A1 | 9/2011 |
| WO | WO-2012078312 A2 | 6/2012 |
| WO | WO-2012154201 A1 | 11/2012 |
| WO | WO-2014021938 A1 | 2/2014 |
| WO | 2014144865 A2 | 9/2014 |
| WO | WO-2015021080 A2 | 2/2015 |
| WO | 2015081440 A1 | 6/2015 |
| WO | 2016022557 A1 | 2/2016 |
| WO | 2016126882 A1 | 8/2016 |
| WO | 2016126987 A1 | 8/2016 |
| WO | 2016172377 A1 | 10/2016 |
| WO | 2016183100 A1 | 11/2016 |
| WO | 2017049231 A1 | 3/2017 |
| WO | 2017053450 A1 | 3/2017 |
| WO | 2017095958 A1 | 6/2017 |
| WO | 2017214574 A1 | 12/2017 |
| WO | 2018026920 A1 | 2/2018 |
| WO | 2018038772 A1 | 3/2018 |
| WO | 2018057526 A2 | 3/2018 |
| WO | 2018094263 A1 | 5/2018 |
| WO | 2018112426 A1 | 6/2018 |
| WO | 2018156792 A1 | 8/2018 |
| WO | 2018170164 A1 | 9/2018 |
| WO | 2018170169 A1 | 9/2018 |
| WO | 2018231864 A1 | 12/2018 |
| WO | 2018231872 A1 | 12/2018 |
| WO | 2019051501 A1 | 3/2019 |
| WO | 2019057099 A1 | 3/2019 |
| WO | 2019079769 A1 | 4/2019 |
| WO | 2019084500 A1 | 5/2019 |
| WO | 2019136175 A1 | 7/2019 |
| WO | 2019147831 A1 | 8/2019 |
| WO | 2019222706 A1 | 11/2019 |
| WO | 2020001344 A1 | 1/2020 |
| WO | 2020139871 A1 | 7/2020 |
| WO | 2020176362 A1 | 9/2020 |
| WO | 2020176678 A1 | 9/2020 |
| WO | 2020176680 A1 | 9/2020 |
| WO | 2020257612 A2 | 12/2020 |
| WO | 2021061829 A1 | 4/2021 |
| WO | 2021119193 A2 | 6/2021 |
| WO | 2021222315 A2 | 11/2021 |
| WO | WO 2021222316 * | 11/2021 |
| WO | WO-2022010934 A2 | 1/2022 |
| WO | 2022046797 A1 | 3/2022 |
| WO | 2022046944 A2 | 3/2022 |
| WO | 2022047076 A1 | 3/2022 |
| WO | WO-2022076326 A1 | 4/2022 |
| WO | WO-2022086866 A1 | 4/2022 |
| WO | WO-2022087293 A1 | 4/2022 |
| WO | 2022093811 A1 | 5/2022 |
| WO | WO-2022098662 A2 | 5/2022 |
| WO | WO-2022159620 A1 | 7/2022 |
| WO | WO-2022178137 A1 | 8/2022 |
| WO | 2022204301 A1 | 9/2022 |
| WO | WO-2022204309 A1 | 9/2022 |
| WO | WO-2022204316 A2 | 9/2022 |
| WO | WO-2022217004 A1 | 10/2022 |
| WO | WO-2022235579 A1 | 11/2022 |
| WO | WO-2022235584 A1 | 11/2022 |
| WO | WO-2022271884 A2 | 12/2022 |
| WO | WO-2023023183 A2 | 2/2023 |
| WO | WO-2023023190 A2 | 2/2023 |
| WO | WO-2023023285 A2 | 2/2023 |
| WO | WO-2023069367 A1 | 4/2023 |
| WO | 2023076419 A2 | 5/2023 |
| WO | 2023076420 A2 | 5/2023 |
| WO | 2023076687 A1 | 5/2023 |
| WO | 2023091609 A2 | 5/2023 |
| WO | 2023091614 A2 | 5/2023 |
| WO | 2023102034 A2 | 6/2023 |
| WO | 2023114432 A2 | 6/2023 |
| WO | 2023130123 A2 | 7/2023 |
| WO | 2023154533 A2 | 8/2023 |
| WO | 2023172520 A2 | 9/2023 |
| WO | 2023191858 A2 | 10/2023 |
| WO | 2023192635 A2 | 10/2023 |
| WO | 2023196499 A1 | 10/2023 |
| WO | 2023205345 A2 | 10/2023 |

OTHER PUBLICATIONS

Kim et al. (Biochimica et Biophysica Acta 1844 (2014) 1983-2001).*
Vajda et al. Current Opinion in Structural Biology, 67 pp. 226-231 (2021).*
Marks et al., J. Biol. Chem. 295(29) 9823-9837 (2020 ).*
Akbar et al., Cell Reports 34, 108856, Mar. 16, 2021.*
Lo et al., BMC Genomics vol. 22, Article No. 116 (2021 (PTO 892)).*
Agbavwe et al.: Efficiency, Error and Yield in Light-Directed Maskless Synthesis of DNA Microarrays. Journal of Nanobiotechnology. 9(57):1-17 (2011).
Arkles et al.: The Role of Polarity in the Structure of Silanes Employed in Surface Modification. Silanes and Other Coupling Agents. 5:51-64 (2009).
ATDBio. Nucleic Acid Structure, Nucleic Acids Book, 9 pages, published on Jan. 22, 2005. from: http://www.atdbio.com/content/5/Nucleic-acid-structure.
ATDBio. Solid-Phase Oligonucleotide Synthesis, Nucleic Acids Book, 20 pages, Published on Jul. 31, 2011. from: http://www.atdbio.com/content/17/Solid-phase-oligonucleotide-synthesis.
Berg: Biochemistry. 5th ED. New York (2002) 148-149.
Blanchard et al.: High-Density Oligonucleotide Arrays. Biosensors & Bioelectronics, 11(6/7):687-690 (1996).
Buermans et al.: Next Generation sequencing technology: Advances and applications, Biochimica et Biophysica Acta (BBA)—Molecular Basis of Disease, 1842:1931-1941 (2014).
Cheng et al.: High throughput parallel synthesis of oligonucleotides with 1536 channel synthesizer. Nucleic Acids Res. 30(18):e93 (2002).
Cleary et al.: Production of complex nucleic acid libraries using highly parallel in situ oligonucleotide synthesis. Nat Methods. 1(3):241-248 (2004).
Cohen et al.: Human population: The next half century. Science. 302:1172-1175 (2003).
Cruse et al.: Atlas of Immunology. Third Edition. Boca Raton:CRC Press (pp. 282-283) (2010).
Elsik et al.: The Genome sequence of taurine cattle: A window of ruminant biology and evolution. Science. 324:522-528 (2009).
Fodor et al.: Light-directed, spatially addressable parallel chemical synthesis. Science. 251(4995):767-773 (1991).
Gao et al.: A method for the generation of combinatorial antibody libraries using pIX phage display. PNAS 99(20):12612-12616 (2002).
GE Healthcare. AKTA oligopilot plus. Data File 18-114-66 ADC. 8 pages (2006).
GE Healthcare. Robust and cost-efficient oligonucleotide synthesis. Application Note 28-4058-08 AA. 4 pages (2005).
Gibson et al.: Creation of a Bacterial Cell Controlled by A Chemically Synthesized Genome. Science. 329(5989):52-56 (2010).
Hudson: Matrix Assisted Synthetic Transformations: A Mosaic of Diverse Contributions. Journal of Combinatorial Chemistry. 1(6):403-457 (1999).
Kong et al.: Parallel gene synthesis in a microfluidic device. Nucleic Acids Res. 35(8) : e61 (2007).

(56) References Cited

OTHER PUBLICATIONS

Kosuri and Church. Large-scale de novo DNA synthesis: technologies and applications. Nature Methods. 11:499-507 (2014) Available at: http://www.nature.com/nmeth/journal/v11/n5/full/nmeth.2918.html.

Kosuri, et al. A scalable gene synthesis by selective amplification of DNA pools from high-fidelity microchips. Nature Biotechnology. 2010; 28:1295-1299.

Kosuri et al.: A scalable gene synthesis platform using high-fidelity DNA microchips Nat.Biotechnol. 28(12):1295-1299 (2010).

Krayden, Inc.: A Guide to Silane Solutions. Silane coupling agents. 7 pages. Published on May 31, 2005 at: http://krayden.com/pdf/xia_silane_chemistry.pdf.

Lausted et al.: POSaM: a fast, flexible, open-source, inkjet oligonucleotide synthesizer and microarrayer. Genome Biology. 5:R58, 17 pages (2004) available at https://www.ncbi.nlm.nih.gov/pmc/articles/PMC507883/.

Lebl et al.: Economical Parallel Oligonucleotide and Peptide Synthesizer—Pet Oligator. Int. J. Peptide Res. Ther. 13(1-2):367-376 (2007).

Leproust et al.: Synthesis of high-quality libraries of long (150mer) oligonucleotides by a novel depurination controlled process. Nucleic Acids Research. 38(8):2522-2540 (2010).

Lewontin and Harti, Population genetics in forensic DNA typing. Science, 254:1745-1750, 1991.

Ma et al.: DNA synthesis, assembly and application in synthetic biology. Current Opinion in Chemical Biology. 16:260-267 (2012).

Ma et al.: Versatile surface functionalization of cyclic olefin copolymer (COC) with sputtered SiO2 thin film for potential BioMEMS applications. Journal of Materials Chemistry. 11 pages (2009).

Mazor et al.: Isolation of Full-Length IgG Antibodies from Combinatorial Libraries Expressed in *Escherichia coli*; Antony S. Dimitrov (ed.), Therapeutic Antibodies: Methods and Protocols, vol. 525, Chapter 11, pp. 217-239 (2009).

McBride & Caruthers. An investigation of several deoxynucleoside phosphoramidites useful for synthesizing deoxyoligonucleotides. Tetrahedron Lett. 24:245-248 (1983).

Mitra et al.: In situ localized amplification and contact replication of many individual DNA molecules. Nucleic Acids Res. 27(24):e34 (1999).

Morin et al.: Profiling the HeLa S3 transcriptome using randomly primed cDNA and massively parallel short-read sequencing. Biotechniques. 45:81-94 (2008).

Opposition to European Patent No. 3030682 filed Mar. 3, 2021.

PCT/US2014/049834 International Preliminary Report on Patentability dated Feb. 18, 2016.

PCT/US2014/049834 International Search Report and Written Opinion mailed Mar. 19, 2015.

PCT/US2014/049834 Invitation to Pay Additional Fees and, where applicable, protest fee mailed Jan. 5, 2015.

Pirrung. How to make a DNA chip. Angew. Chem. Int. Ed. 41:1276-1289 (2002).

Pray. Discovery of DNA Structure and Function: Watson and Crick. Nature Education.6 pages (2008) available at: http://www.nature.com/scitable/topicpage/discovery-of-dna-structure-and-function-watson-397.

Quan et al.: Parallel on-chip gene synthesis and application to optimization of protein expression. Nature Biotechnology. 29:449-452 (2011).

Rafalski and Morgante, Corn and humans: recombination and linkage disequilibrium in two genomes of similar size. Trends in Genetics. 20(2):103-111. (2004).

Rogozin et al.: Origin and evolution of spliceosomal introns. Biology Direct, 7:11 (2012).

Saaem et al.: In situ synthesis of DNA microarray on functionalized cyclic olefin copolymer substrate ACS Applied Materials & Interfaces. 2(2):491-497 (2010).

Sargolzaei et al.: Extent of linkage disequilibrium in Holstein cattle in North America. J.Dairy Science. 91:2106-2117 (2007).

Srivannavit et al.: Design and fabrication of microwell array chips for a solution-based, photogenerated acid-catalyzed parallel oligonucleotide DNA synthesis. Sensors and Actuators A. 116:150-160 (2004).

Steel. The Flow-Thru Chip A Three-dimensional biochip platform. In: Schena, Microarray Biochip Technology, Chapter 5, Natick, MA: Eaton Publishing, 2000, 33 pages.

Taylor et al.: Impact of surface chemistry and blocking strategies on DNA microarrays. Nucleic Acids Research, 31(16):e87 19 pages (2003).

Tian et al.: Accurate multiplex gene synthesis from programmable DNA microchips. Nature. 432(7020):1050-1054 (2004).

U.S. Appl. No. 16/737,401 Final Office Action dated Jun. 13, 2022.
U.S. Appl. No. 14/452,429 Notice of Allowance dated Jun. 7, 2016.
U.S. Appl. No. 14/452,429 Office Action mailed Apr. 9, 2015.
U.S. Appl. No. 14/452,429 Office Action mailed Oct. 21, 2015.
U.S. Appl. No. 14/452,429 Restriction Requirement mailed Dec. 12, 2014.
U.S. Appl. No. 14/885,962 Notice of Allowance dated Nov. 8, 2017 and Sep. 29, 2017.
U.S. Appl. No. 14/885,962 Office Action dated Dec. 16, 2016.
U.S. Appl. No. 14/885,962 Office Action dated Sep. 8, 2016.
U.S. Appl. No. 14/885,962 Restriction Requirement dated Mar. 1, 2016.
U.S. Appl. No. 14/885,963 Notice of Allowance dated May 24, 2016.
U.S. Appl. No. 14/885,963 Office Action dated Feb. 5, 2016.
U.S. Appl. No. 14/885,965 Office Action dated Aug. 28, 2018.
U.S. Appl. No. 14/885,965 Office Action dated Aug. 30, 2017.
U.S. Appl. No. 14/885,965 Office Action dated Feb. 10, 2017.
U.S. Appl. No. 14/885,965 Office Action dated Feb. 18, 2016.
U.S. Appl. No. 14/885,965 Office Action dated Jan. 4, 2018.
U.S. Appl. No. 14/885,965 Office Action dated Jul. 7, 2016.
U.S. Appl. No. 15/187,714 Final Office Action dated Sep. 17, 2019.
U.S. Appl. No. 15/187,714 Office Action dated Apr. 4, 2019.
U.S. Appl. No. 15/187,714 Restriction Requirement dated Sep. 17, 2018.
U.S. Appl. No. 15/187,721 Notice of Allowance dated Dec. 7, 2016.
U.S. Appl. No. 15/187,721 Office Action dated Oct. 14, 2016.
U.S. Appl. No. 15/233,835 Notice of Allowance dated Oct. 4, 2017.
U.S. Appl. No. 15/233,835 Office Action dated Feb. 8, 2017.
U.S. Appl. No. 15/233,835 Office Action dated Jul. 26, 2017.
U.S. Appl. No. 15/233,835 Restriction Requirement dated Nov. 4, 2016.
U.S. Appl. No. 15/245,054 Notice of Allowance dated Dec. 14, 2017.
U.S. Appl. No. 15/245,054 Office Action dated Mar. 21, 2017.
U.S. Appl. No. 15/245,054 Office Action dated Oct. 19, 2016.
U.S. Appl. No. 15/377,547 Final Office Action dated Feb. 8, 2019.
U.S. Appl. No. 15/377,547 Office Action dated Jul. 27, 2018.
U.S. Appl. No. 15/377,547 Office Action dated Mar. 24, 2017.
U.S. Appl. No. 15/377,547 Office Action dated Nov. 30, 2017.
U.S. Appl. No. 15/602,991 Final Office Action dated Dec. 13, 2018.
U.S. Appl. No. 15/602,991 Notice of Allowance dated Oct. 25, 2017.
U.S. Appl. No. 15/602,991 Office Action dated May 31, 2018.
U.S. Appl. No. 15/602,991 Office Action dated May 31, 2019.
U.S. Appl. No. 15/602,991 Office Action dated Sep. 21, 2017.
U.S. Appl. No. 15/603,013 Final Office Action dated Nov. 6, 2019.
U.S. Appl. No. 15/603,013 Office Action dated Jan. 30, 2018.
U.S. Appl. No. 15/603,013 Office Action dated Jul. 10, 2018.
U.S. Appl. No. 15/603,013 Office Action dated Jun. 26, 2019.
U.S. Appl. No. 15/603,013 Office Action dated Oct. 20, 2017.
U.S. Appl. No. 15/729,564 Final Office Action dated Dec. 13, 2018.
U.S. Appl. No. 15/729,564 Office Action dated Jan. 8, 2018.
U.S. Appl. No. 15/729,564 Office Action dated Jun. 6, 2018.
U.S. Appl. No. 15/729,564 Office Action dated May 30, 2019.
U.S. Appl. No. 15/991,992 Office Action dated May 21, 2020.
U.S. Appl. No. 15/991,992 Restriction Requirement dated Mar. 10, 2020.
U.S. Appl. No. 16/039,256 Final Office Action dated Mar. 30, 2021.
U.S. Appl. No. 16/039,256 Office Action dated Aug. 20, 2020.
U.S. Appl. No. 16/039,256 Office Action dated May 10, 2022.

(56) References Cited

OTHER PUBLICATIONS

U.S. Appl. No. 16/039,256 Restriction Requirement dated May 18, 2020.
U.S. Appl. No. 16/409,608 Office Action dated Sep. 9, 2019.
U.S. Appl. No. 16/535,777 Final Office Action dated Oct. 20, 2020.
U.S. Appl. No. 16/535,777 Office Action dated Feb. 8, 2021.
U.S. Appl. No. 16/535,777 Office Action dated Jan. 23, 2020.
U.S. Appl. No. 16/535,779 First Action Interview dated Feb. 10, 2020.
U.S. Appl. No. 16/737,401 Office Action dated Jan. 5, 2022.
U.S. Appl. No. 16/737,401 Restriction Requirement dated Nov. 15, 2021.
Van Tassell et al.: SNP discovery and allele frequency estimation by deep sequencing of reduced representation libraries. Nature Methods. 5:247-252 (2008).
Xu et al.: Design of 240,000 orthogonal 25mer DNA barcode probes. PNAS. 106(7):2289-2294 (2009).
Hasin-Brumshtein et al.: The Effects of Mismatches on DNA Capture by Hybridization. Twist WhitePaper. 6 pages (May 7, 2019).
PCT/US2022/021596 International Search Report mailed Oct. 12, 2022.
PCT/US2022/021596 Invitation to Pay Additional Fees mailed Aug. 15, 2022.
Avnir, Y., et al., "Structural Determination of the Broadly Reactive Anti-IGHV1-69 Anti-idiotypic Antibody G6 and Its Idiotope," Cell Reports, vol. 21, No. 11, pp. 3243-3255 (2017).
Bai et al., "A Novel Human ScFv Library with Non-Combinatorial Synthetic CDR Diversity," pp. 1-18, PLOS One, Oct. 20, 2015.
Chen et al., "Enhancement and destruction of antibody function by some mutation: unequal occurrence is controlled by V gene combinatorial associations," The EMBO Journal, vol. 14, No. 12, pp. 2784-2794, 1995 (11 pages).
Extended European Search Report issued for European Application No. 20867522.3 on Nov. 14, 2023 (11 pages).
File History of U.S. Appl. No. 17/030,216, filed Sep. 23, 2020, available on PAIR.
International Search Report and Written Opinion of International Application No. PCT/US2020/52306, dated Mar. 2, 2021, by Examiner S. Thomas (14 pages).
Janeway et al." The rearrangement of antigen-receptor gene segments controls lymphocyte development," Immunobiology: The Immune System in Health and Disease, 5th edition. New York: Garland Science 2001 (17 pages).
Kussie et al., "A Single Engineered Amino Acid Substitution Changes Antibody Fine Specifitiy," J Immunol, Jan. 1, 1994, 1;152(1) pp. 146-152 (7 pages).
Ponsel et al., "High Affinity, Developability and Functional Size: The Holy Grail of Combinatorial Antibody Library Generation," Molecules, 16:3675-3700 (2011).
Sela-Culang et al., "The structural basis of antibody-antigen recognition," Frontiers in Immunology, vol. 4, Article 302, Oct. 2013 (13 pages).
DATABASE Geneseq, "Anti-CD3-epsilon IgG antibody 252-005 VH region, SEQ:25.", retrieved from EBI accession No. GSP:BLV55389 Database accession No. Bl V55389, Nov. 17, 2022 (2022-11-17)(1 page).
Kuhn et al., "Therapeutic anti-CD3 monoclonal antibodies: from bench to bedside," Immunotherapy, (2016) 8(8), pp. 889-906 (18 pages).
Ma et al., "Anti-CD3 x EGFR bispecific antibody redirects cytokine induced killer cells to glioblastoma in vitro and in vivo," Oncology Reports, 34: pp. 2567-2575, May 14, 2015 (9 pages).
Moradi-Kalbolandi et al., "Evaluation the potential of recombinant anti-CD3 nanobody on immunomodulatory function," Molecular Immunology, 118 (2019), pp. 174-181.
Partial Supplementary European Search Report issued in European Application No. 22776592.2, dated Dec. 12, 2024, by Examiner G. Wimmer (27 pages).
Yu et al., "A novel asymmetrical anti-HER2/CD3 bispecific antibody exhibits potent cytotoxicity for HER2-positive tumor cells," Journal of Experimental & Clinical Cancer Research, 38:355, 16 pages (2019).

\* cited by examiner

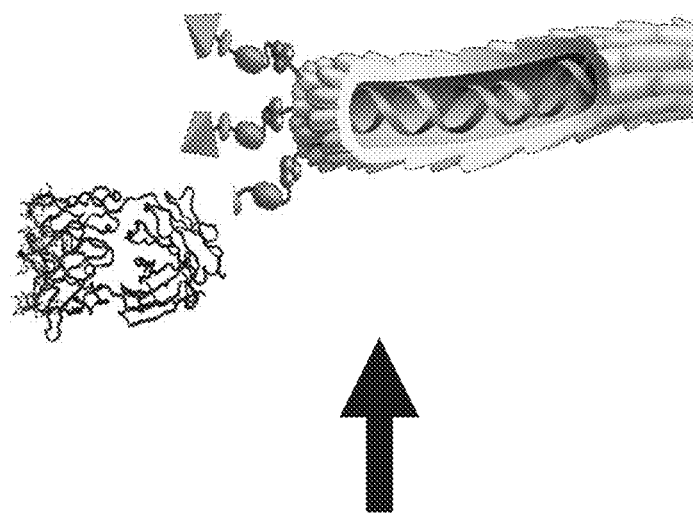
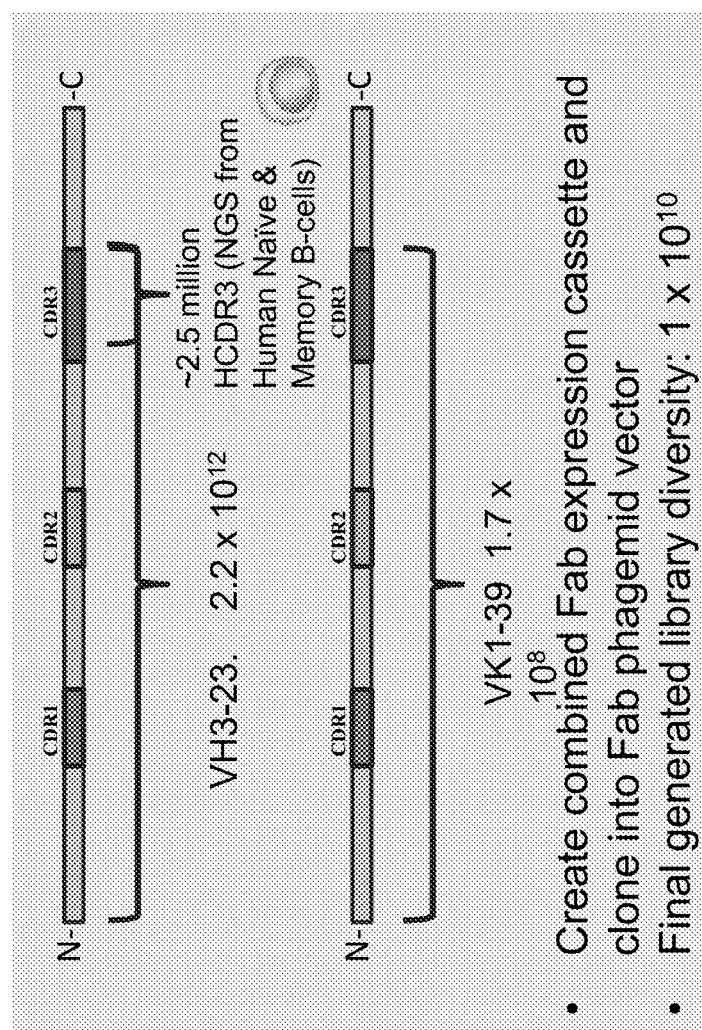
FIG. 8

SEQUENCE LISTING

```
<160> NUMBER OF SEQ ID NOS: 50

<210> SEQ ID NO 1
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Gly Tyr Thr Phe Thr Ser Asn Met His
1               5

<210> SEQ ID NO 2
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Phe Thr Phe Ser Ser Tyr Ala Met Asn
1               5

<210> SEQ ID NO 3
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Phe Thr Phe Ser Ser Tyr Ala Ile Asn
1               5
```

```
<210> SEQ ID NO 4
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Val Ala Ser Ile Ser Ser Tyr Tyr Gly Tyr Thr Tyr Tyr Ala
1               5                   10

<210> SEQ ID NO 5
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Val Ser Ala Val Ser Gly Ser Gly Gly Arg Thr Tyr Tyr Ala
1               5                   10

<210> SEQ ID NO 6
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Val Ser Ala Leu Ser Gly Ser Gly Gly Ser Thr Tyr Tyr Ala
1               5                   10

<210> SEQ ID NO 7
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Gly Gly Asn Tyr Tyr Asn Leu Trp Thr Gly Tyr Tyr Pro Leu Ala Tyr
1               5                   10                  15

<210> SEQ ID NO 8
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Ala Arg Glu Arg Ala Thr Thr Leu Asp Tyr
1               5                   10

<210> SEQ ID NO 9
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9
```

```
Ala Arg Arg Ser Ala Gln Leu Gly Asp Tyr
1               5                   10

<210> SEQ ID NO 10
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Cys Ala Arg Glu Arg Ala Thr Thr Leu Asp Tyr Trp
1               5                   10

<210> SEQ ID NO 11
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Cys Ala Arg Asp Ser Leu Thr Thr Arg Gly Tyr Tyr Tyr Tyr Met Asp
1               5                   10                  15

Val Trp

<210> SEQ ID NO 12
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Arg Ala Ser Gln Asp Ile Ser Thr Tyr Leu Asn
1               5                   10

<210> SEQ ID NO 13
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Arg Ala Ser Gln Thr Ile Tyr Ser His Leu Asn
1               5                   10

<210> SEQ ID NO 14
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Arg Ala Ser Gln Ser Ile Ser Ser Phe Leu Asn
1               5                   10

<210> SEQ ID NO 15
<211> LENGTH: 7
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Tyr Thr Asp Arg Leu Gln Thr
1               5

<210> SEQ ID NO 16
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Val Ala Ser Arg Leu Gln Ser
1               5

<210> SEQ ID NO 17
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Ala Ala Pro Ser Leu Gln Ser
1               5

<210> SEQ ID NO 18
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Gln Gln Gly Gly Ala Leu Pro Phe Thr
1               5

<210> SEQ ID NO 19
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Gln Gln Ser Phe Ser Thr Ser Trp Thr
1               5

<210> SEQ ID NO 20
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Gln Gln Ser Phe Arg Thr Pro Phe Thr
```

```
<210> SEQ ID NO 21
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Asn Trp Val Arg Gln Ala Pro Gly Lys Gly Leu Glu Trp Val
        35                  40                  45

Ser Ala Val Ser Gly Ser Gly Gly Arg Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Arg Ala Thr Thr Leu Asp Tyr Trp Gly Gln Gly Thr Leu
            100                 105                 110

Val Thr Val Ser Ser
        115

<210> SEQ ID NO 22
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 22

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Arg Phe Ser Thr Tyr
            20                  25                  30

Ala Met Asn Trp Val Arg Gln Ala Pro Gly Lys Gly Leu Glu Trp Val
        35                  40                  45

Ser Gly Ile Ser Gly Ser Gly Ser Lys Tyr His Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Ser Leu Thr Thr Arg Gly Tyr Tyr Tyr Met Asp Val
            100                 105                 110

Trp Gly Gln Gly Thr Leu Val Thr Val Ser Ser
        115                 120

<210> SEQ ID NO 23
<211> LENGTH: 123
<212> TYPE: PRT
<213> ORGANISM: Artificial Sequence
<220> FEATURE:
<223> OTHER INFORMATION: Description of Artificial Sequence: Synthetic
``` polypeptide

<400> SEQUENCE: 23

Glu Val Gln Leu Leu Glu Ser Gly Gly Gly Leu Val Gln Pro Gly Gly
1               5                   10                  15

Ser Leu Arg Leu Ser Cys Ala Ala Ser Gly Tyr Thr Phe Thr Ser
            20                  25                  30

Asn Met His Trp Val Arg Gln Ala Pro Gly Lys Gly Leu Glu Trp Val
        35                  40                  45

Ala Ser Ile Ser Ser Tyr Tyr Gly Tyr Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Gly Gly Asn Tyr Tyr Asn Leu Trp Thr Gly Tyr Tyr Pro Leu Ala Tyr
            100                 105                 110

Trp Gly Gln Gly Thr Leu Val Thr Val Ser Ser
        115                 120

<210> SEQ ID NO 24
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 24

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Ala Leu Asn Trp Val Arg Gln Ala Pro Gly Lys Gly Leu Glu Trp Val
        35                  40                  45

Ser Ala Val Thr Gly Ser Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Val Arg Ala Thr Thr Leu Asp Tyr Trp Gly Gln Gly Thr Leu
            100                 105                 110

Val Thr Val Ser Ser
        115

<210> SEQ ID NO 25
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 25

Glu Val Gln Leu Val Glu Ser Gly Gly Gly Leu Val Gln Pro Gly Gly
1               5                   10                  15

Ser Leu Arg Leu Ser Cys Ala Ala Ser Gly Arg Ile Ser Asn Ile Asn
            20                  25                  30

Ile Met Gly Trp Phe Arg Gln Ala Pro Gly Lys Glu Arg Glu Phe Val
            35                  40                  45

Ala Ala Ile Ser Trp Asn Ser Gly Thr Thr Arg Tyr Ala Asp Ser Val
        50                  55                  60

Lys Gly Arg Phe Thr Ile Ser Ala Asp Asn Ser Lys Asn Thr Ala Tyr
65                  70                  75                  80

Leu Gln Met Asn Ser Leu Lys Pro Glu Asp Thr Ala Val Tyr Tyr Cys
                85                  90                  95

Ala Ser Gln Gly Pro Gly Leu Tyr Gly Ser Gly Ser Tyr Leu Arg Tyr
            100                 105                 110

Trp Gly Gln Gly Thr Leu Val Thr Val Ser Ser
            115                 120

<210> SEQ ID NO 26
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 26

Glu Val Gln Leu Val Glu Ser Gly Gly Gly Leu Val Gln Pro Gly Gly
1               5                   10                  15

Ser Leu Arg Leu Ser Cys Ala Ala Ser Gly Arg Ser Leu Tyr Asp Arg
            20                  25                  30

Ala Tyr Val Met Gly Trp Phe Arg Gln Ala Pro Gly Lys Glu Arg Glu
        35                  40                  45

Phe Val Ala Ala Ile Asn Arg Ser Gly Ser Ala Leu Tyr Ala Asp Ser
    50                  55                  60

Val Lys Gly Arg Phe Thr Ile Ser Ala Asp Asn Ser Lys Asn Thr Ala
65                  70                  75                  80

Tyr Leu Gln Met Asn Ser Leu Lys Pro Glu Asp Thr Ala Val Tyr Tyr
                85                  90                  95

Cys Ala Ala Lys Ala Val Thr Ser Arg Asp His Glu Trp Gly Gln Gly
            100                 105                 110

Thr Leu Val Thr Val Ser Ser
        115

<210> SEQ ID NO 27
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 27

Glu Val Gln Leu Val Glu Ser Gly Gly Gly Leu Val Gln Pro Gly Gly
1               5                   10                  15

Ser Leu Arg Leu Ser Cys Ala Ala Ser Val Asp Ile Phe Thr Arg Asn
            20                  25                  30

Ile Met Gly Trp Phe Arg Gln Ala Pro Gly Lys Glu Arg Glu Phe Val
            35                  40                  45

Ala Ala Ile Arg Ser Ser Asp Gly Thr Thr Tyr Tyr Ala Asp Ser Val
        50                  55                  60

Lys Gly Arg Phe Thr Ile Ser Ala Asp Asn Ser Lys Asn Thr Ala Tyr
65                  70                  75                  80

```
Leu Gln Met Asn Ser Leu Lys Pro Glu Asp Thr Ala Val Tyr Tyr Cys
                85                  90                  95

Ala Lys Arg Ala Gly Arg Gly Tyr Ser Tyr Gly Tyr Val Asp Tyr Trp
            100                 105                 110

Gly Gln Gly Thr Leu Val Thr Val Ser Ser
        115                 120

<210> SEQ ID NO 28
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 28

Glu Val Gln Leu Val Glu Ser Gly Gly Gly Leu Val Gln Pro Gly Gly
1               5                   10                  15

Ser Leu Arg Leu Ser Cys Ala Ala Ser Gly Arg Thr Phe Ser Asn Asn
            20                  25                  30

Val Met Gly Trp Phe Arg Gln Ala Pro Gly Lys Glu Arg Glu Phe Val
        35                  40                  45

Ala Ala Ile Ser Ser Ser Ala Thr Thr Leu Tyr Ala Asp Ser Val Lys
    50                  55                  60

Gly Arg Phe Thr Ile Ser Ala Asp Asn Ser Lys Asn Thr Ala Tyr Leu
65                  70                  75                  80

Gln Met Asn Ser Leu Lys Pro Glu Asp Thr Ala Val Tyr Tyr Cys Ala
                85                  90                  95

Gln Lys Asp Thr Ala Leu Lys Val Trp Gly Gln Gly Thr Leu Val Thr
            100                 105                 110

Val Ser Ser
        115

<210> SEQ ID NO 29
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 29

Glu Val Gln Leu Val Glu Ser Gly Gly Gly Leu Val Gln Pro Gly Gly
1               5                   10                  15

Ser Leu Arg Leu Ser Cys Ala Ala Ser Gly Asn Ile Phe Thr Arg His
            20                  25                  30

Ile Met Gly Trp Phe Arg Gln Ala Pro Gly Lys Glu Arg Glu Phe Val
        35                  40                  45

Ala Ala Ile Thr Asn Gly Gly Ser Thr Lys Tyr Ala Asp Ser Val Lys
    50                  55                  60

Gly Arg Phe Thr Ile Ser Ala Asp Asn Ser Lys Asn Thr Ala Tyr Leu
65                  70                  75                  80

Gln Met Asn Ser Leu Lys Pro Glu Asp Thr Ala Val Tyr Tyr Cys Ala
                85                  90                  95

Arg Gln Asp Tyr Tyr Asp Ser Ser Gly His Ile Arg Tyr Trp Gly Gln
            100                 105                 110

Gly Thr Leu Val Thr Val Ser Ser
        115                 120
```

<210> SEQ ID NO 30
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 30

Glu Val Gln Leu Val Glu Ser Gly Gly Gly Leu Val Gln Pro Gly Gly
1               5                   10                  15

Ser Leu Arg Leu Ser Cys Ala Ala Ser Gly Ile Thr Phe Lys Arg Tyr
            20                  25                  30

Val Met Gly Trp Phe Arg Gln Ala Pro Gly Lys Glu Arg Glu Phe Val
        35                  40                  45

Ala Ala Ile Thr Asn Gly Gly Ser Thr Lys Tyr Ala Asp Ser Val Lys
    50                  55                  60

Gly Arg Phe Thr Ile Ser Ala Asp Asn Ser Lys Asn Thr Ala Tyr Leu
65                  70                  75                  80

Gln Met Asn Ser Leu Lys Pro Glu Asp Thr Ala Val Tyr Tyr Cys Ala
                85                  90                  95

Arg Asp Leu Ser Ala Gly Pro Gly Lys Ala Val Tyr Trp Gly Gln Gly
            100                 105                 110

Thr Leu Val Thr Val Ser Ser
        115

<210> SEQ ID NO 31
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 31

Glu Val Gln Leu Val Glu Ser Gly Gly Gly Leu Val Gln Pro Gly Gly
1               5                   10                  15

Ser Leu Arg Leu Ser Cys Ala Ala Ser Gly Thr Thr Phe Arg Ile Asn
            20                  25                  30

Val Met Gly Trp Phe Arg Gln Ala Pro Gly Lys Glu Arg Glu Phe Val
        35                  40                  45

Ala Ala Ile Thr Ser Ser Gly Ser Ser Thr Leu Tyr Ala Asp Ser Val
    50                  55                  60

Lys Gly Arg Phe Thr Ile Ser Ala Asp Asn Ser Lys Asn Thr Ala Tyr
65                  70                  75                  80

Leu Gln Met Asn Ser Leu Lys Pro Glu Asp Thr Ala Val Tyr Tyr Cys
                85                  90                  95

Ala Arg Gly Gly Gly Tyr His Arg Leu Trp Gly Gln Gly Thr Leu Val
            100                 105                 110

Thr Val Ser Ser
        115

<210> SEQ ID NO 32
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 32

Glu Val Gln Leu Val Glu Ser Gly Gly Gly Leu Val Gln Pro Gly Gly
1               5                   10                  15

Ser Leu Arg Leu Ser Cys Ala Ala Ser Gly Ser Ala Phe Ser Ser Thr
            20                  25                  30

Val Met Gly Trp Phe Arg Gln Ala Pro Gly Lys Glu Arg Glu Phe Val
        35                  40                  45

Ala Ala Ile Asn Asn Phe Gly Thr Thr Lys Tyr Ala Asp Ser Val Lys
    50                  55                  60

Gly Arg Phe Thr Ile Ser Ala Asp Asn Ser Lys Asn Thr Ala Tyr Leu
65                  70                  75                  80

Gln Met Asn Ser Leu Lys Pro Glu Asp Thr Ala Val Tyr Tyr Cys Ala
                85                  90                  95

His Arg Val Arg His Tyr Gly Asp Trp Glu Gly Gly Ala Leu Asp Val
            100                 105                 110

Trp Gly Gln Gly Thr Leu Val Thr Val Ser Ser
            115                 120

<210> SEQ ID NO 33
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 33

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Thr Ile Tyr Ser His
            20                  25                  30

Leu Asn Trp Tyr Gln Gln Lys Pro Gly Lys Ala Pro Lys Leu Leu Ile
        35                  40                  45

Tyr Val Ala Ser Arg Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Phe Ser Thr Ser Trp
                85                  90                  95

Thr Phe Gly Gly Gly Thr Lys Val Glu Ile Lys
            100                 105

<210> SEQ ID NO 34
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 34

Asp Ile Gln Met Thr Gln Ser Gln Ser Ser Leu Ser Ala Ser Val Gly
1               5                   10                  15

Asp Arg Val Thr Ile Thr Cys Arg Ala Ser Gln Ser Ile Arg Thr Ser
            20                  25                  30

Leu Asn Trp Tyr Gln Gln Pro Gly Lys Ala Pro Lys Leu Leu Ile Tyr
        35                  40                  45

```
Ala Ala Ser Arg Leu Gln Ser Gly Val Pro Ser Arg Phe Ser Gly Ser
 50                  55                  60

Gly Ser Gly Thr Asp Phe Thr Leu Thr Ile Ser Ser Leu Gln Pro Glu
 65                  70                  75                  80

Asp Phe Ala Thr Tyr Tyr Cys Gln Gln Ser Tyr Ser Thr Leu Tyr Ser
                 85                  90                  95

Phe Gly Gly Gly Thr Lys Val Glu Ile Lys
            100                 105
```

<210> SEQ ID NO 35
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 35

```
Asp Ile Gln Met Thr Gln Ser Pro Ser Ser Leu Ser Ala Ser Val Gly
 1               5                   10                  15

Asp Arg Val Thr Ile Thr Cys Arg Ala Ser Gln Asp Ile Ser Thr Tyr
                 20                  25                  30

Leu Asn Trp Tyr Gln Gln Lys Pro Gly Lys Ala Pro Lys Leu Leu Ile
             35                  40                  45

Tyr Tyr Thr Asp Arg Leu Gln Thr Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Gly Gly Ala Leu Pro Phe
                 85                  90                  95

Thr Phe Gly Gln Gly Thr Lys Val Glu Ile Lys
            100                 105
```

<210> SEQ ID NO 36
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 36

```
Asp Ile Gln Met Thr Gln Ser Pro Ser Ser Leu Ser Ala Ser Val Gly
 1               5                   10                  15

Asp Arg Val Thr Ile Thr Cys Arg Thr Ser Gln Ser Ile Ser Thr Tyr
                 20                  25                  30

Leu Asn Trp Tyr Gln Gln Lys Pro Gly Lys Ala Pro Lys Leu Leu Ile
             35                  40                  45

Tyr Thr Ala Ser Arg Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ser Tyr Ser Thr Pro Trp
                 85                  90                  95

Thr Phe Gly Gly Gly Thr Lys Val Glu Ile Lys
            100                 105
```

<210> SEQ ID NO 37
<211> LENGTH: 509

<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 37

Met Glu Trp Ser Trp Val Phe Leu Phe Phe Leu Ser Val Thr Thr Gly
1               5                   10                  15

Val His Ser Glu Val Gln Leu Val Glu Ser Gly Gly Gly Leu Val Gln
            20                  25                  30

Pro Gly Gly Ser Leu Lys Leu Ser Cys Ala Ala Ser Gly Phe Thr Phe
        35                  40                  45

Asn Lys Tyr Ala Met Asn Trp Val Arg Gln Ala Pro Gly Lys Gly Leu
    50                  55                  60

Glu Trp Val Ala Arg Ile Arg Ser Lys Tyr Asn Asn Tyr Ala Thr Tyr
65                  70                  75                  80

Tyr Ala Asp Ser Val Lys Asp Arg Phe Thr Ile Ser Arg Asp Asp Ser
                85                  90                  95

Lys Asn Thr Ala Tyr Leu Gln Met Asn Asn Leu Lys Thr Glu Asp Thr
            100                 105                 110

Ala Val Tyr Tyr Cys Val Arg His Gly Asn Phe Gly Asn Ser Tyr Ile
        115                 120                 125

Ser Tyr Trp Ala Tyr Trp Gly Gln Gly Thr Leu Val Thr Val Ser Ser
    130                 135                 140

Gly Gly Gly Gly Ser Gly Gly Gly Ser Gly Gly Gly Gly Ser Gln
145                 150                 155                 160

Thr Val Val Thr Gln Glu Pro Ser Leu Thr Val Ser Pro Gly Gly Thr
                165                 170                 175

Val Thr Leu Thr Cys Gly Ser Ser Thr Gly Ala Val Thr Ser Gly Asn
            180                 185                 190

Tyr Pro Asn Trp Val Gln Gln Lys Pro Gly Gln Ala Pro Arg Gly Leu
        195                 200                 205

Ile Gly Gly Thr Lys Phe Leu Ala Pro Gly Thr Pro Ala Arg Phe Ser
    210                 215                 220

Gly Ser Leu Leu Gly Gly Lys Ala Ala Leu Thr Leu Ser Gly Val Gln
225                 230                 235                 240

Pro Glu Asp Glu Ala Glu Tyr Tyr Cys Val Leu Trp Tyr Ser Asn Arg
                245                 250                 255

Trp Val Phe Gly Gly Gly Thr Lys Leu Thr Val Leu Gly Gly Gly Gly
            260                 265                 270

Ser Gly Gly Gly Gly Ser Glu Pro Lys Ser Ser Asp Lys Thr His Thr
        275                 280                 285

Cys Pro Pro Cys Pro Ala Pro Glu Ala Ala Gly Gly Pro Ser Val Phe
    290                 295                 300

Leu Phe Pro Pro Lys Pro Lys Asp Thr Leu Met Ile Ser Arg Thr Pro
305                 310                 315                 320

Glu Val Thr Cys Val Val Val Asp Val Ser His Glu Asp Pro Glu Val
                325                 330                 335

Lys Phe Asn Trp Tyr Val Asp Gly Val Glu Val His Asn Ala Lys Thr
            340                 345                 350

Lys Pro Arg Glu Glu Gln Tyr Asn Ser Thr Tyr Arg Val Val Ser Val
        355                 360                 365

Leu Thr Val Leu His Gln Asp Trp Leu Asn Gly Lys Glu Tyr Lys Cys
    370                 375                 380

Lys Val Ser Asn Lys Ala Leu Pro Ala Pro Ile Glu Lys Thr Ile Ser
385                 390                 395                 400

Lys Ala Lys Gly Gln Pro Arg Glu Pro Gln Val Tyr Thr Leu Pro Pro
            405                 410                 415

Ser Arg Glu Glu Met Thr Lys Asn Gln Val Ser Leu Ser Cys Ala Val
        420                 425                 430

Lys Gly Phe Tyr Pro Ser Asp Ile Ala Val Glu Trp Glu Ser Asn Gly
    435                 440                 445

Gln Pro Glu Asn Asn Tyr Lys Thr Thr Pro Pro Val Leu Asp Ser Asp
450                 455                 460

Gly Ser Phe Phe Leu Val Ser Lys Leu Thr Val Asp Lys Ser Arg Trp
465                 470                 475                 480

Gln Gln Gly Asn Val Phe Ser Cys Ser Val Met His Glu Ala Leu His
                485                 490                 495

Asn Arg Tyr Thr Gln Lys Ser Leu Ser Leu Ser Pro Gly
            500                 505

<210> SEQ ID NO 38
<211> LENGTH: 486
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 38

Glu Val Gln Leu Leu Glu Ser Gly Gly Gly Leu Val Gln Pro Gly Gly
1               5                   10                  15

Ser Leu Arg Leu Ser Cys Ala Ala Ser Gly Gly Tyr Thr Phe Thr Ser
            20                  25                  30

Asn Met His Trp Val Arg Gln Ala Pro Gly Lys Gly Leu Glu Trp Val
        35                  40                  45

Ala Ser Ile Ser Ser Tyr Tyr Gly Tyr Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Gly Gly Asn Tyr Tyr Asn Leu Trp Thr Gly Tyr Tyr Pro Leu Ala Tyr
            100                 105                 110

Trp Gly Gln Gly Thr Leu Val Thr Val Ser Ser Gly Gly Gly Gly Ser
        115                 120                 125

Gly Gly Gly Gly Ser Gly Gly Gly Gly Ser Asp Ile Gln Met Thr Gln
    130                 135                 140

Ser Pro Ser Ser Leu Ser Ala Ser Val Gly Asp Arg Val Thr Ile Thr
145                 150                 155                 160

Cys Arg Ala Ser Gln Asp Ile Ser Thr Tyr Leu Asn Trp Tyr Gln Gln
                165                 170                 175

Lys Pro Gly Lys Ala Pro Lys Leu Leu Ile Tyr Tyr Thr Asp Arg Leu
            180                 185                 190

Gln Thr Gly Val Pro Ser Arg Phe Ser Gly Ser Gly Ser Gly Thr Asp
        195                 200                 205

Phe Thr Leu Thr Ile Ser Ser Leu Gln Pro Glu Asp Phe Ala Thr Tyr
    210                 215                 220

Tyr Cys Gln Gln Gly Gly Ala Leu Pro Phe Thr Phe Gly Gln Gly Thr

```
                225                 230                 235                 240
Lys Val Glu Ile Lys Gly Gly Gly Ser Gly Gly Gly Gly Ser Glu
                        245                 250                 255
Pro Lys Ser Ser Asp Lys Thr His Thr Cys Pro Pro Cys Pro Ala Pro
                260                 265                 270
Glu Ala Ala Gly Gly Pro Ser Val Phe Leu Phe Pro Pro Lys Pro Lys
                275                 280                 285
Asp Thr Leu Met Ile Ser Arg Thr Pro Glu Val Thr Cys Val Val Val
                290                 295                 300
Asp Val Ser His Glu Asp Pro Glu Val Lys Phe Asn Trp Tyr Val Asp
305                 310                 315                 320
Gly Val Glu Val His Asn Ala Lys Thr Lys Pro Arg Glu Glu Gln Tyr
                    325                 330                 335
Asn Ser Thr Tyr Arg Val Val Ser Val Leu Thr Val Leu His Gln Asp
                340                 345                 350
Trp Leu Asn Gly Lys Glu Tyr Lys Cys Lys Val Ser Asn Lys Ala Leu
            355                 360                 365
Pro Ala Pro Ile Glu Lys Thr Ile Ser Lys Ala Lys Gly Gln Pro Arg
        370                 375                 380
Glu Pro Gln Val Tyr Thr Leu Pro Pro Ser Arg Glu Glu Met Thr Lys
385                 390                 395                 400
Asn Gln Val Ser Leu Ser Cys Ala Val Lys Gly Phe Tyr Pro Ser Asp
                    405                 410                 415
Ile Ala Val Glu Trp Glu Ser Asn Gly Gln Pro Glu Asn Asn Tyr Lys
                420                 425                 430
Thr Thr Pro Pro Val Leu Asp Ser Asp Gly Ser Phe Phe Leu Val Ser
            435                 440                 445
Lys Leu Thr Val Asp Lys Ser Arg Trp Gln Gln Gly Asn Val Phe Ser
        450                 455                 460
Cys Ser Val Met His Glu Ala Leu His Asn Arg Tyr Thr Gln Lys Ser
465                 470                 475                 480
Leu Ser Leu Ser Pro Gly
                485

<210> SEQ ID NO 39
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 39

Glu Val Gln Leu Val Glu Ser Gly Gly Gly Leu Val Gln Pro Gly Gly
1               5                   10                  15
Ser Leu Arg Leu Ser Cys Ala Ala Ser Gly Ile Ser Ile Ser Thr Lys
            20                  25                  30
Val Met Gly Trp Phe Arg Gln Ala Pro Gly Lys Glu Arg Glu Phe Val
        35                  40                  45
Ala Ala Ile Thr Trp Ser Gly Gly Ser Thr Lys Tyr Ala Asp Ser Val
    50                  55                  60
Lys Gly Arg Phe Thr Ile Ser Ala Asp Asn Ser Lys Asn Thr Ala Tyr
65                  70                  75                  80
Leu Gln Met Asn Ser Leu Lys Pro Glu Asp Thr Ala Val Tyr Tyr Cys
                85                  90                  95
```

Ala Gly Arg Phe Ala Arg Gly Arg Tyr Tyr Gly Met Asp Val Trp Gly
            100                 105                 110

Gln Gly Thr Leu Val Thr Val Ser Ser
        115                 120

<210> SEQ ID NO 40
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 40

Glu Val Gln Leu Val Glu Ser Gly Gly Gly Leu Val Gln Pro Gly Gly
1               5                   10                  15

Ser Leu Arg Leu Ser Cys Ala Ala Ser Val Asp Ile Phe Thr Arg Asn
            20                  25                  30

Ile Met Gly Trp Phe Arg Gln Ala Pro Gly Lys Glu Arg Glu Phe Val
        35                  40                  45

Ala Ala Ile Arg Ser Ser Asp Gly Thr Thr Tyr Tyr Ala Asp Ser Val
    50                  55                  60

Lys Gly Arg Phe Thr Ile Ser Ala Asp Asn Ser Lys Asn Thr Ala Tyr
65                  70                  75                  80

Leu Gln Met Asn Ser Leu Lys Pro Glu Asp Thr Ala Val Tyr Tyr Cys
                85                  90                  95

Ala Lys Arg Ala Gly Arg Gly Tyr Ser Tyr Gly Tyr Val Asp Tyr Trp
            100                 105                 110

Gly Gln Gly Thr Leu Val Thr Val Ser Ser
        115                 120

<210> SEQ ID NO 41
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 41

Glu Val Gln Leu Val Glu Ser Gly Gly Gly Leu Val Gln Pro Gly Gly
1               5                   10                  15

Ser Leu Arg Leu Ser Cys Ala Ala Ser Gly Asn Ile Phe Thr Arg His
            20                  25                  30

Ile Met Gly Trp Phe Arg Gln Ala Pro Gly Lys Glu Arg Glu Phe Val
        35                  40                  45

Ala Ala Ile Thr Asn Gly Gly Ser Thr Lys Tyr Ala Asp Ser Val Lys
    50                  55                  60

Gly Arg Phe Thr Ile Ser Ala Asp Asn Ser Lys Asn Thr Ala Tyr Leu
65                  70                  75                  80

Gln Met Asn Ser Leu Lys Pro Glu Asp Thr Ala Val Tyr Tyr Cys Ala
                85                  90                  95

Arg Gln Asp Tyr Tyr Asp Ser Ser Gly His Ile Arg Tyr Trp Gly Gln
            100                 105                 110

Gly Thr Leu Val Thr Val Ser Ser
        115                 120

<210> SEQ ID NO 42
<211> LENGTH: 614

<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 42

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Gly Gly Gly Ser Gly Gly Gly
        115                 120                 125

Gly Ser Gly Gly Gly Gly Ser Gly Gly Gly Gly Ser Asp Ile Gln Met
    130                 135                 140

Thr Gln Ser Pro Ser Ser Leu Ser Ala Ser Val Gly Asp Arg Val Thr
145                 150                 155                 160

Ile Thr Cys Arg Ala Ser Gln Asp Val Asn Thr Ala Val Ala Trp Tyr
                165                 170                 175

Gln Gln Lys Pro Gly Lys Ala Pro Lys Leu Leu Ile Tyr Ser Ala Ser
            180                 185                 190

Phe Leu Tyr Ser Gly Val Pro Ser Arg Phe Ser Gly Ser Arg Ser Gly
        195                 200                 205

Thr Asp Phe Thr Leu Thr Ile Ser Ser Leu Gln Pro Glu Asp Phe Ala
    210                 215                 220

Thr Tyr Tyr Cys Gln Gln His Tyr Thr Thr Pro Pro Thr Phe Gly Gln
225                 230                 235                 240

Gly Thr Lys Val Glu Ile Lys Glu Pro Lys Ser Ser Asp Lys Thr His
                245                 250                 255

Thr Cys Pro Pro Cys Pro Ala Pro Glu Ala Ala Gly Gly Pro Ser Val
            260                 265                 270

Phe Leu Phe Pro Pro Lys Pro Lys Asp Thr Leu Met Ile Ser Arg Thr
        275                 280                 285

Pro Glu Val Thr Cys Val Val Val Asp Val Ser His Glu Asp Pro Glu
    290                 295                 300

Val Lys Phe Asn Trp Tyr Val Asp Gly Val Glu Val His Asn Ala Lys
305                 310                 315                 320

Thr Lys Pro Arg Glu Glu Gln Tyr Asn Ser Thr Tyr Arg Val Val Ser
                325                 330                 335

Val Leu Thr Val Leu His Gln Asp Trp Leu Asn Gly Lys Glu Tyr Lys
            340                 345                 350

Cys Lys Val Ser Asn Lys Ala Leu Pro Ala Pro Ile Glu Lys Thr Ile
        355                 360                 365

Ser Lys Ala Lys Gly Gln Pro Arg Glu Pro Gln Val Tyr Thr Leu Pro
    370                 375                 380

Pro Ser Arg Glu Glu Met Thr Lys Asn Gln Val Ser Leu Thr Cys Leu
385                 390                 395                 400

Val Lys Gly Phe Tyr Pro Ser Asp Ile Ala Val Glu Trp Glu Ser Asn
            405                 410                 415

Gly Gln Pro Glu Asn Asn Tyr Lys Thr Thr Pro Pro Val Leu Asp Ser
        420                 425                 430

Asp Gly Ser Phe Phe Leu Tyr Ser Lys Leu Thr Val Asp Lys Ser Arg
    435                 440                 445

Trp Gln Gln Gly Asn Val Phe Ser Cys Ser Val Met His Glu Ala Leu
450                 455                 460

His Asn His Tyr Thr Gln Lys Ser Leu Ser Leu Ser Pro Gly Gly Gly
465                 470                 475                 480

Gly Gly Ser Gly Gly Gly Ser Gly Gly Gly Ser Glu Val Gln
            485                 490                 495

Leu Val Glu Ser Gly Gly Leu Val Gln Pro Gly Gly Ser Leu Arg
            500                 505                 510

Leu Ser Cys Ala Ala Ser Gly Ile Ser Ile Ser Thr Lys Val Met Gly
            515                 520                 525

Trp Phe Arg Gln Ala Pro Gly Lys Glu Arg Glu Phe Val Ala Ala Ile
530                 535                 540

Thr Trp Ser Gly Gly Ser Thr Lys Tyr Ala Asp Ser Val Lys Gly Arg
545                 550                 555                 560

Phe Thr Ile Ser Ala Asp Asn Ser Lys Asn Thr Ala Tyr Leu Gln Met
                565                 570                 575

Asn Ser Leu Lys Pro Glu Asp Thr Ala Val Tyr Tyr Cys Ala Gly Arg
            580                 585                 590

Phe Ala Arg Gly Arg Tyr Tyr Gly Met Asp Val Trp Gly Gln Gly Thr
            595                 600                 605

Leu Val Thr Val Ser Ser
    610

<210> SEQ ID NO 43
<211> LENGTH: 615
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 43

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Gly Gly Gly Gly Ser Gly Gly Gly

-continued

```
            115                 120                 125
Gly Ser Gly Gly Gly Ser Gly Gly Gly Ser Asp Ile Gln Met
        130                 135                 140
Thr Gln Ser Pro Ser Ser Leu Ser Ala Ser Val Gly Asp Arg Val Thr
145                     150                  155                 160
Ile Thr Cys Arg Ala Ser Gln Asp Val Asn Thr Ala Val Ala Trp Tyr
                    165                  170                  175
Gln Gln Lys Pro Gly Lys Ala Pro Lys Leu Leu Ile Tyr Ser Ala Ser
                180                  185                  190
Phe Leu Tyr Ser Gly Val Pro Ser Arg Phe Ser Gly Ser Arg Ser Gly
            195                  200                  205
Thr Asp Phe Thr Leu Thr Ile Ser Ser Leu Gln Pro Glu Asp Phe Ala
210                  215                  220
Thr Tyr Tyr Cys Gln Gln His Tyr Thr Thr Pro Pro Thr Phe Gly Gln
225                  230                  235                  240
Gly Thr Lys Val Glu Ile Lys Glu Pro Lys Ser Ser Asp Lys Thr His
                 245                  250                  255
Thr Cys Pro Pro Cys Pro Ala Pro Glu Ala Ala Gly Gly Pro Ser Val
             260                  265                  270
Phe Leu Phe Pro Pro Lys Pro Lys Asp Thr Leu Met Ile Ser Arg Thr
             275                  280                  285
Pro Glu Val Thr Cys Val Val Asp Val Ser His Glu Asp Pro Glu
290                  295                  300
Val Lys Phe Asn Trp Tyr Val Asp Gly Val Glu Val His Asn Ala Lys
305                  310                  315                  320
Thr Lys Pro Arg Glu Glu Gln Tyr Asn Ser Thr Tyr Arg Val Val Ser
                 325                  330                  335
Val Leu Thr Val Leu His Gln Asp Trp Leu Asn Gly Lys Glu Tyr Lys
             340                  345                  350
Cys Lys Val Ser Asn Lys Ala Leu Pro Ala Pro Ile Glu Lys Thr Ile
             355                  360                  365
Ser Lys Ala Lys Gly Gln Pro Arg Glu Pro Gln Val Tyr Thr Leu Pro
370                  375                  380
Pro Ser Arg Glu Glu Met Thr Lys Asn Gln Val Ser Leu Thr Cys Leu
385                  390                  395                  400
Val Lys Gly Phe Tyr Pro Ser Asp Ile Ala Val Glu Trp Glu Ser Asn
                 405                  410                  415
Gly Gln Pro Glu Asn Asn Tyr Lys Thr Thr Pro Pro Val Leu Asp Ser
             420                  425                  430
Asp Gly Ser Phe Phe Leu Tyr Ser Lys Leu Thr Val Asp Lys Ser Arg
             435                  440                  445
Trp Gln Gln Gly Asn Val Phe Ser Cys Ser Val Met His Glu Ala Leu
450                  455                  460
His Asn His Tyr Thr Gln Lys Ser Leu Ser Leu Ser Pro Gly Gly Gly
465                  470                  475                  480
Gly Gly Ser Gly Gly Gly Gly Ser Gly Gly Gly Gly Ser Glu Val Gln
                 485                  490                  495
Leu Val Glu Ser Gly Gly Gly Leu Val Gln Pro Gly Gly Ser Leu Arg
             500                  505                  510
Leu Ser Cys Ala Ala Ser Val Asp Ile Phe Thr Arg Asn Ile Met Gly
             515                  520                  525
Trp Phe Arg Gln Ala Pro Gly Lys Glu Arg Glu Phe Val Ala Ala Ile
530                  535                  540
```

```
Arg Ser Ser Asp Gly Thr Thr Tyr Tyr Ala Asp Ser Val Lys Gly Arg
545                 550                 555                 560

Phe Thr Ile Ser Ala Asp Asn Ser Lys Asn Thr Ala Tyr Leu Gln Met
                565                 570                 575

Asn Ser Leu Lys Pro Glu Asp Thr Ala Val Tyr Tyr Cys Ala Lys Arg
            580                 585                 590

Ala Gly Arg Gly Tyr Ser Tyr Gly Tyr Val Asp Tyr Trp Gly Gln Gly
        595                 600                 605

Thr Leu Val Thr Val Ser Ser
610                 615

<210> SEQ ID NO 44
<211> LENGTH: 613
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 44

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Gly Gly Gly Gly Ser Gly Gly Gly
        115                 120                 125

Gly Ser Gly Gly Gly Gly Ser Gly Gly Gly Gly Ser Asp Ile Gln Met
    130                 135                 140

Thr Gln Ser Pro Ser Ser Leu Ser Ala Ser Val Gly Asp Arg Val Thr
145                 150                 155                 160

Ile Thr Cys Arg Ala Ser Gln Asp Val Asn Thr Ala Val Ala Trp Tyr
                165                 170                 175

Gln Gln Lys Pro Gly Lys Ala Pro Lys Leu Leu Ile Tyr Ser Ala Ser
            180                 185                 190

Phe Leu Tyr Ser Gly Val Pro Ser Arg Phe Ser Gly Ser Arg Ser Gly
        195                 200                 205

Thr Asp Phe Thr Leu Thr Ile Ser Ser Leu Gln Pro Glu Asp Phe Ala
    210                 215                 220

Thr Tyr Tyr Cys Gln Gln His Tyr Thr Thr Pro Pro Thr Phe Gly Gln
225                 230                 235                 240

Gly Thr Lys Val Glu Ile Lys Glu Pro Lys Ser Ser Asp Lys Thr His
                245                 250                 255

Thr Cys Pro Pro Cys Pro Ala Pro Glu Ala Ala Gly Gly Pro Ser Val
            260                 265                 270

Phe Leu Phe Pro Pro Lys Pro Lys Asp Thr Leu Met Ile Ser Arg Thr
```

```
                275                 280                 285
Pro Glu Val Thr Cys Val Val Asp Val Ser His Glu Asp Pro Glu
290                 295                 300

Val Lys Phe Asn Trp Tyr Val Asp Gly Val Glu Val His Asn Ala Lys
305                 310                 315                 320

Thr Lys Pro Arg Glu Glu Gln Tyr Asn Ser Thr Tyr Arg Val Val Ser
                325                 330                 335

Val Leu Thr Val Leu His Gln Asp Trp Leu Asn Gly Lys Glu Tyr Lys
            340                 345                 350

Cys Lys Val Ser Asn Lys Ala Leu Pro Ala Pro Ile Glu Lys Thr Ile
            355                 360                 365

Ser Lys Ala Lys Gly Gln Pro Arg Glu Pro Gln Val Tyr Thr Leu Pro
370                 375                 380

Pro Ser Arg Glu Glu Met Thr Lys Asn Gln Val Ser Leu Thr Cys Leu
385                 390                 395                 400

Val Lys Gly Phe Tyr Pro Ser Asp Ile Ala Val Glu Trp Glu Ser Asn
                405                 410                 415

Gly Gln Pro Glu Asn Asn Tyr Lys Thr Thr Pro Pro Val Leu Asp Ser
            420                 425                 430

Asp Gly Ser Phe Phe Leu Tyr Ser Lys Leu Thr Val Asp Lys Ser Arg
            435                 440                 445

Trp Gln Gln Gly Asn Val Phe Ser Cys Ser Val Met His Glu Ala Leu
450                 455                 460

His Asn His Tyr Thr Gln Lys Ser Leu Ser Leu Ser Pro Gly Gly Gly
465                 470                 475                 480

Gly Gly Ser Gly Gly Gly Gly Ser Gly Gly Gly Gly Ser Glu Val Gln
                485                 490                 495

Leu Val Glu Ser Gly Gly Gly Leu Val Gln Pro Gly Gly Ser Leu Arg
            500                 505                 510

Leu Ser Cys Ala Ala Ser Gly Asn Ile Phe Thr Arg His Ile Met Gly
            515                 520                 525

Trp Phe Arg Gln Ala Pro Gly Lys Glu Arg Glu Phe Val Ala Ala Ile
530                 535                 540

Thr Asn Gly Gly Ser Thr Lys Tyr Ala Asp Ser Val Lys Gly Arg Phe
545                 550                 555                 560

Thr Ile Ser Ala Asp Asn Ser Lys Asn Thr Ala Tyr Leu Gln Met Asn
                565                 570                 575

Ser Leu Lys Pro Glu Asp Thr Ala Val Tyr Tyr Cys Ala Arg Gln Asp
            580                 585                 590

Tyr Tyr Asp Ser Ser Gly His Ile Arg Tyr Trp Gly Gln Gly Thr Leu
            595                 600                 605

Val Thr Val Ser Ser
    610

<210> SEQ ID NO 45
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 45

His His His His His His
1               5
```

<210> SEQ ID NO 46
<211> LENGTH: 62
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (51)..(52)
<223> OTHER INFORMATION: Thymidine-succinyl hexamide CED phosphoramidite

<400> SEQUENCE: 46
agacaatcaa ccatttgggg tggacagcct tgacctctag acttcggcat ttttttttt      60 tt                                                                    62

<210> SEQ ID NO 47
<211> LENGTH: 112
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (101)..(102)
<223> OTHER INFORMATION: Thymidine-succinyl hexamide CED phosphoramidite

<400> SEQUENCE: 47
cgggatcctt atcgtcatcg tcgtacagat cccgacccat tgctgtcca ccagtcatgc       60 tagccatacc atgatgatga tgatgatgag aaccccgcat tttttttttt tt            112

<210> SEQ ID NO 48
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 48
atgcggggtt ctcatcatc                                                   19

<210> SEQ ID NO 49
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 49
cgggatcctt atcgtcatcg                                                  20

<210> SEQ ID NO 50
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: F, L, W, or G
<220> FEATURE:
<221> NAME/KEY: MOD_RES
<222> LOCATION: (4)..(4)

```
<223> OTHER INFORMATION: A or S
<220> FEATURE:
<221> NAME/KEY: MOD_RES
<222> LOCATION: (5)..(5)
<223> OTHER INFORMATION: A, G, S, or T
<220> FEATURE:
<221> NAME/KEY: MOD_RES
<222> LOCATION: (7)..(7)
<223> OTHER INFORMATION: S, T, or N
<220> FEATURE:
<221> NAME/KEY: MOD_RES
<222> LOCATION: (8)..(8)
<223> OTHER INFORMATION: W, S, R, T, or G
<220> FEATURE:
<221> NAME/KEY: MOD_RES
<222> LOCATION: (9)..(9)
<223> OTHER INFORMATION: S, G, N, or D
<220> FEATURE:
<221> NAME/KEY: MOD_RES
<222> LOCATION: (10)..(10)
<223> OTHER INFORMATION: G, S, or D
<220> FEATURE:
<221> NAME/KEY: MOD_RES
<222> LOCATION: (11)..(11)
<223> OTHER INFORMATION: G, S, T, D, A, or N
<220> FEATURE:
<221> NAME/KEY: MOD_RES
<222> LOCATION: (12)..(12)
<223> OTHER INFORMATION: G, S, T, D, or A
<220> FEATURE:
<221> NAME/KEY: MOD_RES
<222> LOCATION: (14)..(14)
<223> OTHER INFORMATION: Y, N, S, or D

<400> SEQUENCE: 50

Glu Xaa Val Xaa Xaa Ile Xaa Xaa Xaa Xaa Xaa Xaa Thr Xaa Tyr
1               5                   10                  15
```

ANTIBODIES THAT BIND CD3 EPSILON

CROSS REFERENCE

This application claims the benefit of U.S. Provisional Patent Application No. 63/165,656, filed on Mar. 24, 2021, which is incorporated by reference in its entirety.

SEQUENCE LISTING

The instant application contains a Sequence Listing which has been submitted electronically in ASCII format and is hereby incorporated by reference in its entirety. Said ASCII copy, created on Jun. 2, 2022, is named 44854-820_201_SL.txt and is 54,266 bytes in size.

BACKGROUND

Cluster of differentiation 3 (CD3) is a multimeric protein complex and T cell co-receptor. CD3 is required for T-cell activation and plays an important role in various diseases including cancer, autoimmune disease, and diabetes and therapeutic antibodies targeting CD3 have clinical significance. Antibodies possess the capability to bind with high specificity and affinity to biological targets. However, the design of therapeutic antibodies is challenging due to balancing of immunological effects with efficacy. Thus, there is a need to develop compositions and methods for generation of antibodies for use in therapeutics.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF SUMMARY

Provided herein are antibodies or antibody fragments comprising an amino acid sequence at least about 90% identical to that set forth in any one of SEQ NOs: 25-32. In some embodiments, the antibody or antibody fragment comprises an amino acid sequence at least about 95% identical to that set forth in any one of SEQ ID NOs: 25-32. In some embodiments, the antibody or antibody fragment comprises an amino acid sequence as set forth in any one of SEQ ID NOs: 25-32. In some embodiments, the antibody is a monoclonal antibody, a polyclonal antibody, a bi-specific antibody, a multispecific antibody, a grafted antibody, a human antibody, a humanized antibody, a synthetic antibody, a chimeric antibody, a camelized antibody, a single-chain Fvs (scFv), a single chain antibody, a Fab fragment, a F(ab')2 fragment, a Fd fragment, a Fv fragment, a single-domain antibody, an isolated complementarily determining region (CDR), a diabody, fragment comprised of only a single monomeric variable domain, disulfide-linked Fvs (sdFv), an intrabody, an anti-idiotypic (anti-Id) antibody, or ab antigen-binding fragments thereof. In some embodiments, the antibody or antibody fragment binds to CD3 with a $K_D$ of less than 75 nM. In some embodiments, the antibody or antibody fragment binds to CD3 with a $K_D$ of less than 50 nM. In some embodiments, the antibody or antibody fragment binds to CD3 with a $K_D$ of less than 25 nM. In some embodiments, the antibody or antibody fragment binds to CD3 with a $K_D$ of less than 10 nM.

Provided herein are antibodies or antibody fragments that bind CD3, comprising an immunoglobulin heavy chain comprising an amino acid sequence at least about 90% identical to that set forth in any one of SEQ ID NOs: 25-32. In some embodiments, the immunoglobulin heavy chain comprises an amino acid sequence at least about 95% identical to that set forth in any one of SEQ ID NOs: 25-32. In some embodiments, the immunoglobulin heavy chain comprises an amino acid sequence as set forth in any one of SEQ ID NOs: 25-32. In some embodiments, the antibody is a monoclonal antibody, a polyclonal antibody, a bi-specific antibody, a multispecific antibody, a grafted antibody, a human antibody, a humanized antibody, a synthetic antibody, a chimeric antibody, a camelized antibody, a single-chain Fvs (say), a single chain antibody, a Fab fragment, a F(ab')2 fragment, a Fd fragment, a Fv fragment, a single-domain antibody, an isolated complementarity determining region (CDR), a diabody, a fragment comprised of only a single monomeric variable domain, disulfide-linked Fvs (sdFv), an intrabody, an anti-idiotypic (anti-Id) antibody, or ab antigen-binding fragments thereof. In some embodiments, the antibody or antibody fragment thereof is chimeric or humanized, in some embodiments, the antibody or antibody fragment binds to CD3 with a $K_D$ of less than 75 nM. In some embodiments, the antibody or antibody fragment binds to CD3 with a $K_D$ of less than 50 nM. In some embodiments, the antibody or antibody fragment binds to CD3 with a $K_D$ of less than 25 nM. In some embodiments, the antibody or antibody fragment binds to CD3 with a $K_D$ of less than 10 nM.

Provided herein are methods of treating cancer comprising administering the antibodies or antibody fragments described herein.

Provided herein are methods of treating a viral infection comprising administering the antibodies or antibody fragments described herein.

BRIEF DESCRIPTION OF THE DRAWINGS

FIG. 8 depicts a schema of design of phage-displayed hyperimmune libraries generated herein.

FIG. 9A depicts a graph of CDR3 counts per length. FIG. 9B depicts graphs of CDRH1, CDRH2, and CDRH3 lengths.

FIG. 19A depicts all results and FIG. 19B shows a subset of the top 10. FIG. 19C depicts another comparison of cytotoxic assays, and FIG. 19D depicts top clones for cell killing based on human T-cell binding profiles

FIG. 24B is enlarged version of FIG. 24A at the 0-250 MFI region.

DETAILED DESCRIPTION

Figure 1:
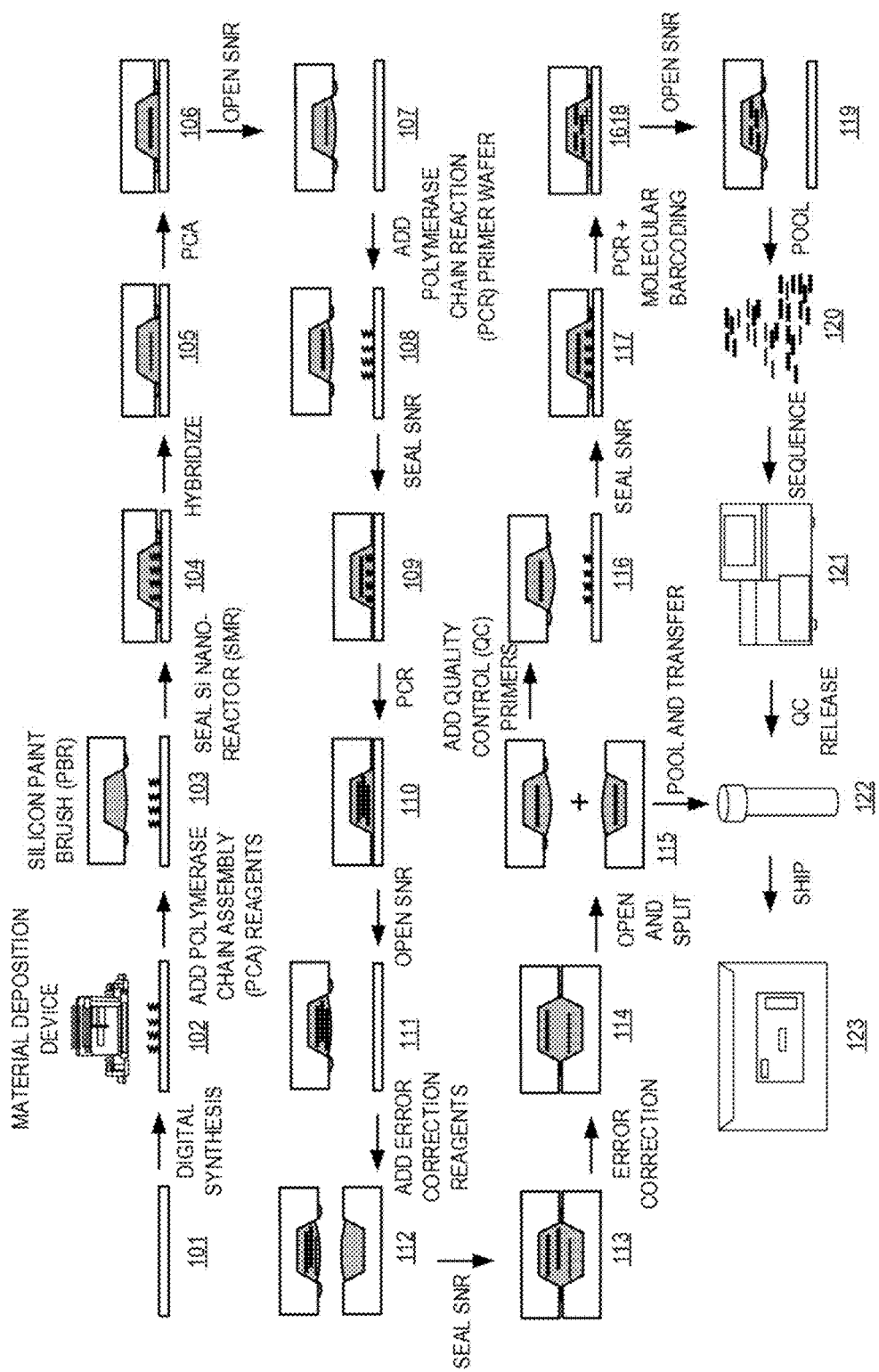
FIG. 1 presents a diagram of steps demonstrating an exemplary process workflow for gene synthesis as disclosed herein.

The present disclosure employs, unless otherwise indicated, conventional molecular biology techniques, which are within the skill of the art. Unless defined otherwise, all technical and scientific terms used herein have the same meaning as is commonly understood by one of ordinary skill in the art.

Definitions

Throughout this disclosure, various embodiments are presented in a range format. It should be understood that the description in range format is merely for convenience and brevity and should not be construed as an inflexible limitation on the scope of any embodiments. Accordingly, the description of a range should be considered to have specifically disclosed all the possible subranges as well as individual numerical values within that range to the tenth of the unit of the lower limit unless the context clearly dictates otherwise. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual values within that range, for example, 1.1, 2, 2.3, 5, and 5.9. This applies regardless of the breadth of the range. The upper and lower limits of these intervening ranges may independently be included in the smaller ranges, and are also encompassed within the disclosure, subject to any specifically excluded limit in the stated range. Where the stated range includes one or both of the limits, ranges excluding either or both of those included limits are also included in the disclosure, unless the context clearly dictates otherwise.

The terminology used herein is for the purpose of describing particular embodiments only and is not intended to be limiting of any embodiment. As used herein, the singular forms "a," "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items.

Unless specifically stated or obvious from context, as used herein, the term "about" in reference to a number or range of numbers is understood to mean the stated number and numbers +/−10% thereof, or 10% below the lower listed limit and 10% above the higher listed limit for the values listed for a range.

Unless specifically stated, as used herein, the term "nucleic acid" encompasses double- or triple-stranded nucleic acids, as well as single-stranded molecules. In double- or triple-stranded nucleic acids, the nucleic acid strands need not be coextensive (i.e., a double-stranded nucleic acid need not be double-stranded along the entire length of both strands). Nucleic acid sequences, when provided, are listed in the 5' to 3' direction, unless stated otherwise. Methods described herein provide for the generation of isolated nucleic acids. Methods described herein additionally provide for the generation of isolated and purified nucleic acids. A "nucleic acid" as referred to herein can comprise at least 5, 10, 20, 30, 40, 50, 60, 70, 80, 90, 100, 125, 150, 175, 200, 225, 250, 275, 300, 325, 350, 375, 400, 425, 450, 475, 500, 600, 700, 800, 900, 1000, 1100, 1200, 1300, 1400, 1500, 1600, 1700, 1800, 1900, 2000, or more bases in length. Moreover, provided herein are methods for the synthesis of any number of polypeptide-segments encoding nucleotide sequences, including sequences encoding non-ribosomal peptides (NRPs), sequences encoding non-ribosomal peptide-synthetase (NRPS) modules and synthetic variants, polypeptide segments of other modular proteins, such as antibodies, polypeptide segments from other protein families, including non-coding DNA or RNA, such as regulatory sequences e.g. promoters, transcription factors, enhancers, siRNA, shRNA, RNAi, miRNA, small nucleolar RNA derived from microRNA, or any functional or structural DNA or RNA unit of interest. The following are non-limiting examples of polynucleotides: coding or non-coding regions of a gene or gene fragment, intergenic DNA, loci (locus) defined from linkage analysis, exons, introns, messenger RNA (mRNA), transfer RNA, ribosomal RNA, short interfering RNA (siRNA), short-hairpin RNA (shRNA), micro-RNA (miRNA), small nucleolar RNA, ribozymes, complementary DNA (cDNA), which is a DNA representation of mRNA, usually obtained by reverse transcription of messenger RNA (mRNA) or by amplification; DNA molecules produced synthetically or by amplification; genomic DNA, recombinant polynucleotides, branched polynucleotides, plasmids, vectors, isolated DNA of any sequence, isolated RNA of any sequence, nucleic acid probes, and primers. cDNA encoding for a gene or gene fragment referred herein may comprise at least one region encoding for exon sequences without an intervening introit sequence in the genomic equivalent sequence.

Antibody Libraries

Provided herein are methods, compositions, and systems for generation of antibodies. Methods, compositions, and systems described herein for the optimization of antibodies comprise a ratio-variant approach that mirror the natural diversity of antibody sequences. In some instances, libraries of optimized antibodies comprise variant antibody sequences. In some instances, the variant antibody sequences are designed comprising variant CDR regions. In some instances, the variant antibody sequences comprising variant CDR regions are generated by shuffling the natural CDR sequences in a llama, humanized, or chimeric framework. In some instances, such libraries are synthesized, cloned into expression vectors, and translation products (antibodies) evaluated for activity. In some instances, fragments of sequences are synthesized and subsequently assembled. In some instances, expression vectors are used to display and enrich desired antibodies, such as phage display. In some instances, the phage vector is a Fab phagemid vector. Selection pressures used during enrichment in some instances includes binding affinity, toxicity, immunological tolerance, stability, or other factor. Such expression vectors allow antibodies with specific properties to be selected ("panning"), and subsequent propagation or amplification of such sequences enriches the library with these sequences. Panning rounds can be repeated any number of times, such as 1, 2, 3, 4, 5, 6, 7, or more than 7 rounds. In some instances, each round of panning involves a number of washes. In some instances, each round of panning involves at least or about 1, 2, 3, 4, 5, 6, 7, 8, 9, 10, 11, 12, 13, 14, 15, 16, or more than 16 washes.

Described herein are methods and systems of in-silico library design. Libraries as described herein, in some instances, are designed based on a database comprising a variety of antibody sequences. In some instances, the database comprises a plurality of variant antibody sequences against various targets. In some instances, the database comprises at least 100, 500, 1000, 1500, 2000, 2500, 3000, 3500, 4000, 4500, 5000, or more than 5000 antibody sequences. An exemplary database is an iCAN database. In some instances, the database comprises naïve and memory B-cell receptor sequences. In some instances, the naïve and memory B-cell receptor sequences are human, mouse, or primate sequences. In some instances, the naïve and memory B-cell receptor sequences are human sequences. In some instances, the database is analyzed for position specific variation. In some instances, antibodies described herein comprise position specific variations in CDR regions. In some instances, the CDR regions comprise multiple sites for variation.

Described herein are libraries comprising variation in a CDR region. In some instances, the CDR is CDR1, CDR2, or CDR3 of a variable heavy chain. In some instances, the CDR is CDR1, CDR2, or CDR3 of a variable light chain. In some instances, the libraries comprise multiple variants encoding for CDR1, CDR2, or CDR3. In some instances, the libraries as described herein encode for at least 50, 100, 200, 300, 400, 500, 1000, 1200, 1500, 1700, 2000, 2500, 3000, 3500, 4000, 4500, 5000, or more than 5000 CDR1 sequences. In some instances, the libraries as described herein encode for at least 50, 100, 200, 300, 400, 500, 1000, 1200, 1500, 1700, 2000, 2500, 3000, 3500, 4000, 4500, 5000, or more than 5000 CDR2 sequences. In some instances, the libraries as described herein encode for at least 50, 100, 200, 300, 400, 500, 1000, 1200, 1500, 1700, 2000, 2500, 3000, 3500, 4000, 4500, 5000, or more than 5000 CDR3 sequences. In-silico antibodies libraries are in some instances synthesized, assembled, and enriched for desired sequences.

Following synthesis of CDR1 variants, CDR2 variants, and CDR3 variants, in some instances, the CDR1 variants, the CDR2 variants, and the CDR3 variants are shuffled to generate a diverse library. In some instances, the diversity of the libraries generated by methods described herein have a theoretical diversity of at least or about $10^7$, $10^8$, $10^9$, $10^{10}$, $10^{11}$, $10^{12}$, $10^{13}$, $10^{14}$, $10^{15}$, $10^{16}$, $10^{17}$, $10^{18}$, or more than $10^{18}$ sequences. In some instances, the library has a final library diversity of at least or about $10^7$, $10^8$, $10^9$, $10^{10}$, $10^{11}$, $10^{12}$, $10^{13}$, $10^{14}$, $10^{15}$, $10^{16}$, $10^{17}$, $10^{18}$, or more than $10^{18}$ sequences.

The germline sequences corresponding to a variant sequence may also be modified to generate sequences in a library. For example, sequences generated by methods described herein comprise at least 1, 2, 3, 4, 5, 6, 7, 8, 9, 10, 11, 12, 13, 14, 15, 16, or more than 16 mutations from the germline sequence. In some instances, sequences generated comprise no more than 1, 2, 3, 4, 5, 6, 7, 8, 9, 10, 11, 12, 13, 14, 15, 16, or no more than 18 mutations from the germline sequence. In some instances, sequences generated comprise about 1, 2, 3, 4, 5, 6, 7, 8, 9, 10, 11, 12, 13, 14, 15, 16, or about 18 mutations relative to the germline sequence.

Antibody Libraries

Provided herein are libraries generated from methods described herein. Antibodies described herein result in improved functional activity, structural stability, expression, specificity, or a combination thereof. In some instances, the antibody is a single domain antibody. In some instances, the single domain antibody comprises one heavy chain variable domain. In some instances, the single domain antibody is a VHH antibody.

As used herein, the term antibody will be understood to include proteins having the characteristic two-armed, V-shape of a typical antibody molecule as well as one or more fragments of an antibody that retain the ability to specifically bind to an antigen. Exemplary antibodies include, but are not limited to, a monoclonal antibody, a polyclonal antibody, a bi-specific antibody, a multispecific antibody, a grafted antibody, a human antibody, a humanized antibody, a synthetic antibody, a chimeric antibody, a camelized antibody, a single-chain Fvs (scFv) (including fragments in which the VL and VH are joined using recombinant methods by a synthetic or natural linker that enables them to be made as a single protein chain in which the VL and VH regions pair to form monovalent molecules, including single chain Fab and scFab), a single chain antibody, a Fab fragment (including monovalent fragments comprising the VL, VH, CL, and CH1 domains), a F(ab')2 fragment (including bivalent fragments comprising two Fab fragments linked by a disulfide bridge at the hinge region), a Fd fragment (including fragments comprising the VH and CH1 fragment), a Fv fragment (including fragments comprising the VL and VH domains of a single arm of an antibody), a single-domain antibody (dAb or sdAb) (including fragments comprising a VH domain), an isolated complementarity determining region (CDR), a diabody (including fragments comprising bivalent dimers such as two VL and VH domains bound to each other and recognizing two different antigens), a fragment comprised of only a single monomeric variable domain, disulfide-linked Fvs (sdFv), an intrabody, an anti-idiotypic (anti-Id) antibody, or ab antigen-binding fragments thereof. In some instances, the libraries disclosed herein comprise nucleic acids encoding for an antibody, wherein the antibody is a Fv antibody, including Fv antibodies comprised of the minimum antibody fragment which contains a complete antigen-recognition and antigen-binding site. In some embodiments, the Fv antibody consists of a dimer of one heavy chain and one light chain variable domain in tight, non-covalent association, and the three hypervariable regions of each variable domain interact to define an antigen-binding site on the surface of the VH-VL dimer. In some embodiments, the six hypervariable regions confer antigen-binding specificity to the antibody. In some embodiments, a single variable domain (or half of an Fv comprising only three hypervariable regions specific for an antigen, including single domain antibodies isolated from camelid animals comprising one heavy chain variable domain such as VHH antibodies or nanobodies) has the ability to recognize and bind antigen. In some instances, the libraries disclosed herein comprise nucleic acids encoding for an antibody, wherein the antibody is a single-chain Fv or say, including antibody fragments comprising a VH, a VL, or both a VH and VL domain, wherein both domains are present in a single polypeptide chain, in some embodiments, the Fv polypeptide further comprises a polypeptide linker between the VH and VL domains allowing the scFv to form the desired structure for antigen binding. In some instances, a scFv is linked to the Fc fragment or a VHH is linked to the Fc fragment (including minibodies). In some instances, the antibody comprises immunoglobulin molecules and immunologically active fragments of immunoglobulin molecules, e.g., molecules that contain an antigen binding site. Immunoglobulin molecules are of any type (e.g., IgG, IgM, IgD, IgA and IgY), class (e.g., IgG 1, IgG 2, IgG 3, IgG 4, IgA 1 and IgA 2) or subclass.

In some embodiments, libraries comprise immunoglobulins that are adapted to the species of an intended therapeutic target. Generally, these methods include "mammalization" and comprises methods for transferring donor antigen-binding information to a less immunogenic mammal antibody acceptor to generate useful therapeutic treatments. In some instances, the mammal is mouse, rat, equine, sheep, cow, primate (e.g., chimpanzee, baboon, gorilla, orangutan, monkey), dog, cat, pig, donkey, rabbit, and human. In some instances, provided herein are libraries and methods for felinization and caninization of antibodies.

"Humanized" forms of non-human antibodies can be chimeric antibodies that contain minimal sequence derived from the non-human antibody. A humanized antibody is generally a human antibody (recipient antibody) in which residues from one or more CDRs are replaced by residues from one or more CDRs of a non-human antibody (donor antibody). The donor antibody can be any suitable non-human antibody, such as a mouse, rat, rabbit, chicken, or non-human primate antibody having a desired specificity, affinity, or biological effect. In some instances, selected framework region residues of the recipient antibody are replaced by the corresponding framework region residues from the donor antibody. Humanized antibodies may also comprise residues that are not found in either the recipient antibody or the donor antibody. In some instances, these modifications are made to further refine antibody performance.

"Caninization" can comprise a method for transferring non-canine antigen-binding information from a donor antibody to a less immunogenic canine antibody acceptor to generate treatments useful as therapeutics in dogs. In some instances, caninized forms of non-canine antibodies provided herein are chimeric antibodies that contain minimal sequence derived from non-canine antibodies. In some instances, caninized antibodies are canine antibody sequences ("acceptor" or "recipient" antibody) in which hypervariable region residues of the recipient are replaced by hypervariable region residues from a non-canine species ("donor" antibody) such as mouse, rat, rabbit, cat, dogs, goat, chicken, bovine, horse, llama, camel, dromedaries, sharks, non-human primates, human, humanized, recombinant sequence, or an engineered sequence having the desired properties. In some instances, framework region (FR) residues of the canine antibody are replaced by corresponding non-canine FR residues. In some instances, caninized antibodies include residues that are not found in the recipient antibody or in the donor antibody. In some instances, these modifications are made to further refine antibody performance. The caninized antibody may also comprise at least a portion of an immunoglobulin constant region (Fc) of a canine antibody.

"Felinization" can comprise a method for transferring non-feline antigen-binding information from a donor antibody to a less immunogenic feline antibody acceptor to generate treatments useful as therapeutics in cats. In some instances, felinized forms of non-feline antibodies provided herein are chimeric antibodies that contain minimal sequence derived from non-feline antibodies. In some instances, felinized antibodies are feline antibody sequences ("acceptor" or "recipient" antibody) in which hypervariable region residues of the recipient are replaced by hypervariable region residues from a non-feline species ("donor" antibody) such as mouse, rat, rabbit, cat, dogs, goat, chicken, bovine, horse, llama, camel, dromedaries, sharks, non-human primates, human, humanized, recombinant sequence, or an engineered sequence having the desired properties. In some instances, framework region (FR) residues of the feline antibody are replaced by corresponding non-feline FR residues. In some instances, felinized antibodies include residues that are not found in the recipient antibody or in the donor antibody. In some instances, these modifications are made to further refine antibody performance. The felinized antibody may also comprise at least a portion of an immunoglobulin constant region (Fc) of a felinize antibody.

Methods as described herein may be used for generation of libraries encoding a non-immunoglobulin. In some instances, the libraries comprise antibody mimetics. Exemplary antibody mimed cs include, but are not limited to, anticalins, affilins, affibody molecules, affimers, affitins, alphabodies, avimers, atrimers, DARPins, fynomers, Kunitz domain-based proteins, monobodies, anticalins, knottins, armadillo repeat protein-based proteins, and bicyclic peptides.

Libraries described herein comprising nucleic acids encoding for an antibody comprise variations in at least one region of the antibody. Exemplary regions of the antibody for variation include, but are not limited to, a complementarity-determining region (CDR), a variable domain, or a constant domain. In some instances, the CDR is CDR1, CDR2, or CDR3. In some instances, the CDR is a heavy domain including, but not limited to, CDRH1, CDRH2, and CDRH3. In some instances, the CDR is a light domain including, but not limited to, CDRL1, CDRL2, and CDRL3. In some instances, the variable domain is variable domain, light chain (VL) or variable domain, heavy chain (VH). In some instances, the CDR1, CDR2, or CDR3 is of a variable domain, light chain (VL). CDR1, CDR2, or CDR3 of a variable domain, light chain (VL) can be referred to as CDRL1, CDRL2, or CDRL3, respectively. CDR1, CDR2, or CDR3 of a variable domain, heavy chain (VH) can be referred to as CDRH1, CDRH2, or CDRH3, respectively. In some instances, the VL domain comprises kappa or lambda chains. In some instances, the constant domain is constant domain, light chain (CL) or constant domain, heavy chain (CH).

Provided herein are libraries comprising nucleic acids encoding for an antibody comprising variation in at least one region of the antibody, wherein the region is the CDR region. In some instances, the antibody is a single domain antibody comprising one heavy chain variable domain such as a VHH antibody. In some instances, the VHH antibody comprises variation in one or more CDR regions. In some instances, the VHH libraries described herein comprise at least or about 100, 200, 300, 400, 500, 600, 700, 800, 900, 1000, 1200, 1400, 1600, 1800, 2000, 2400, 2600, 2800, 3000, or more than 3000 sequences of a CDR1, CDR2, or CDR3. For example, the libraries comprise at least 2000 sequences of a CDR1, at least 1200 sequences for CDR2, and at least 1600 sequences for CDR3. In some instances, each sequence is non-identical.

Libraries as described herein may comprise varying lengths of a CDRH1, CDRH2, CDRH3, CDR1, CDR2, CDRL3, or combinations thereof of amino acids when translated. In some instances, the length of the CDRH1, CDRH2, CDRH3, CDRL1, CDRL2, CDRL3, or combinations thereof of amino acids when translated is at least or about 5, 6, 7, 8, 9, 10, 11, 12, 13, 14, 15, 16, 17, 18, 19, 20, 21, 22, 23, 24, 25, 26, 27, 28, 29, 30, or more than 30 amino acids.

Libraries comprising nucleic acids encoding for antibodies having variant CDR sequences as described herein comprise various lengths of amino acids when translated. In some instances, the length of each of the amino acid fragments or average length of the amino acid synthesized may be at least or about 15, 20, 25, 30, 35, 40, 45, 50, 55, 60, 65, 70, 75, 80, 85, 90, 95, 100, 105, 110, 115, 120, 125, 130, 135, 140, 145, 150, or more than 150 amino acids. In some instances, the length of the amino acid is about 15 to 150, 20 to 145, 25 to 140, 30 to 135, 35 to 130, 40 to 125, 45 to 120, 50 to 115, 55 to 110, 60 to 110, 65 to 105, 70 to 100, or 75 to 95 amino acids. In some instances, the length of the amino acid is about 22 amino acids to about 75 amino acids. In some instances, the antibodies comprise at least or about 100, 200, 300, 400, 500, 600, 700, 800, 900, 1000, 2000, 3000, 4000, 5000, or more than 5000 amino acids. In some instances, the library is a VHH library. In some instances, the library is an antibody library.

Libraries as described herein encoding for a VHH antibody comprise variant CDR sequences that are shuffled to generate a library with a theoretical diversity of at least or about $10^7$, $10^8$, $10^9$, $10^{10}$, $10^{11}$, $10^{12}$, $10^{13}$, $10^{14}$, $10^{15}$, $10^{16}$, $10^{17}$, $10^{18}$, or more than $10^{18}$ sequences. In some instances, the library has a final library diversity of at least or about $10^7$, $10^8$, $10^9$, $10^{10}$, $10^{12}$, $10^{13}$, $10^{14}$, $10^{15}$, $10^{16}$, $10^{17}$, $10^{18}$ or more than $10^{18}$ sequences.

Libraries as described herein encoding for an antibody or immunoglobulin comprise variant CDR sequences that are shuffled to generate a library with a theoretical diversity of at least or about $10^7$, $10^8$, $10^9$, $10^{10}$, $10^{11}$, $10^{12}$, $10^{13}$, $10^{14}$, $10^{15}$, $10^{16}$, $10^{17}$, $10^{18}$, or more than $10^{18}$ sequences. In some instances, the library has a final library diversity of at least or about $10^7$, $10^8$, $10^9$, $10^{10}$, $10^{11}$, $10^{12}$, $10^{13}$, $10^{14}$, $10^{15}$, $10^{16}$, $10^{17}$, $10^{18}$, or more than $10^{18}$ sequences.

Methods described herein provide for synthesis of libraries comprising nucleic acids encoding an antibody or immunoglobulin, wherein each nucleic acid encodes for a predetermined variant of at least one predetermined reference nucleic acid sequence. In some cases, the predetermined reference sequence is a nucleic acid sequence encoding for a protein, and the variant library comprises sequences encoding for variation of at least a single codon such that a plurality of different variants of a single residue in the subsequent protein encoded by the synthesized nucleic acid are generated by standard translation processes. In some instances, the antibody library comprises varied nucleic acids collectively encoding variations at multiple positions. In some instances, the variant library comprises sequences encoding for variation of at least a single codon of a CDRH1, CDRH2, CDRH3, CDRL1, CDRL2, CDRL3, VL, or VE domain. In some instances, the variant library comprises sequences encoding for variation of multiple codons of a CDRH1, CDRH2, CDRH3, CDRL1, CDRL2, CDRL3, VL, or VH domain. In some instances, the variant library comprises sequences encoding for variation of multiple codons of framework element 1 (FW1), framework element 2 (FW2), framework element 3 (FW3), or framework element 4 (FW4). An exemplary number of codons for variation include, but are not limited to, at least or about 1, 5, 10, 15, 20, 25, 30, 35, 40, 45, 50, 55, 60, 65, 70, 75, 80, 85, 90, 95, 100, 125, 150, 175, 225, 250, 275, 300, or more than 300 codons.

In some instances, the at least one region of the antibody for variation is from heavy chain V-gene family, heavy chain D-gene family, heavy chain J-gene family, light chain V-gene family, or light chain J-gene family. In some instances, the light chain V-gene family comprises immunoglobulin kappa (IGK) gene or immunoglobulin lambda (IGL). Exemplary regions of the antibody for variation include, but are not limited to, IGHV1-18, IGHV1-69, IGHV1-8, IGHV3-21, IGHV3-23, IGHV3-30/33m, IGHV3-28, IGHV1-69, IGHV4-39, IGHV4-59/61, IGKV1-39, IGKV1-9, IGKV2-28, IGKV3-11, IGKV3-15, IGKV3-20, IGKV4-1, IGLV1-51, IGLV2-14, IGLV1-40, and IGLV3-1. In some instances, the gene is IGHV1-69, IGHV3-30, IGHV3-23, IGHV3, IGHV1-46, IGHV1, or IGHV1-8. In some instances, the gene is IGHV1-69 and IGHV3-30. In some instances, the region of the antibody for variation is IGHJ3, IGHJ6, IGHJ, IGHJ4, IGHJ5, IGHJ2, or IGH1. In some instances, the region of the antibody for variation is IGHJ3, IGHJ6, IGHJ, or IGHJ4. In some instances, the at least one region of the antibody for variation is IGHV1-69, IGHV3-23, IGKV3-20, IGKV1-39 or combinations thereof. In some instances, the at least one region of the antibody for variation is IGHV1-69 or IGHV3-23. In some instances, the at least one region of the antibody for variation is IGKV3-20 or IGKV1-39. In some instances, the at least one region of the antibody for variation is IGHV1-69 and IGKV3-20, In some instances, the at least one region of the antibody for variation is IGHV1-69 and IGKV1-39. In some instances, the at least one region of the antibody for variation is IGHV3-23 and IGKV3-20. In some instances, the at least one region of the antibody for variation is IGHV3-23 and IGKV1-39.

Provided herein are libraries comprising nucleic acids encoding for antibodies, wherein the libraries are synthesized with various numbers of fragments. In some instances, the fragments comprise the CDRH1, CDRH2, CDRH3, CDRL1, CDRL2, CDRL3, VL, or VH domain. In some instances, the fragments comprise framework element 1 (FW1), framework element 2 (FW2), framework element 3 (FW3), or framework element 4 (FW4). In some instances, the antibody libraries are synthesized with at least or about 2 fragments, 3 fragments, 4 fragments, 5 fragments, or more than 5 fragments. The length of each of the nucleic acid fragments or average length of the nucleic acids synthesized may be at least or about 50, 75, 100, 125, 150, 175, 200, 225, 250, 275, 300, 325, 350, 375, 400, 425, 450, 475, 500, 525, 550, 575, 600, or more than 600 base pairs. In some instances, the length is about 50 to 600, 75 to 575, 100 to 550, 125 to 525, 150 to 500, 175 to 475, 200 to 450, 225 to 425, 250 to 400, 275 to 375, or 300 to 350 base pairs.

Libraries comprising nucleic acids encoding for antibodies or immunoglobulins as described herein comprise various lengths of amino acids when translated. In some instances, the length of each of the amino acid fragments or average length of the amino acid synthesized may be at least or about 15, 20, 25, 30, 35, 40, 45, 50, 55, 60, 65, 70, 75, 80, 85, 90, 95, 100, 105, 110, 115, 120, 125, 130, 135, 140, 145, 150, or more than 150 amino acids. In some instances, the length of the amino acid is about 15 to 150, 20 to 145, 25 to 140, 30 to 135, 35 to 130, 40 to 125, 45 to 120, 50 to 115, 55 to 110, 60 to 110, 65 to 105, 70 to 100, or 75 to 95 amino acids. In some instances, the length of the amino acid is about 22 amino acids to about 75 amino acids. In some instances, the antibodies comprise at least or about 100, 200, 300, 400, 500, 600, 700, 800, 900, 1000, 2000, 3000, 4000, 5000, or more than 5000 amino acids.

A number of variant sequences for the at least one region of the antibody for variation are de novo synthesized using methods as described herein. In some instances, a number of variant sequences is de novo synthesized for CDRH1, CDRH2, CDRH3, CDRL1, CDRL2, CDRL3, VL, VH, or combinations thereof. In some instances, a number of variant sequences is de novo synthesized for framework element 1 (FW1), framework element 2 (FW2), framework element 3 (FW3), or framework element 4 (FW4). The number of variant sequences may be at least or about 5, 10, 15, 20, 25, 30, 35, 40, 45, 50, 55, 60, 65, 70, 75, 80, 85, 90, 95, 100, 125, 150, 175, 200, 225, 250, 275, 300, 325, 350, 375, 400, 425, 450, 475, 500, or more than 500 sequences. In some instances, the number of variant sequences is at least or about 500, 600, 700, 800, 900, 1000, 2000, 3000, 4000, 5000, 6000, 7000, 8000, or more than 8000 sequences. In some instances, the number of variant sequences is about 10 to 500, 25 to 475, 50 to 450, 75 to 425, 100 to 400, 125 to 375, 150 to 350, 175 to 325, 200 to 300, 225 to 375, 250 to 350, or 275 to 325 sequences.

Variant sequences for the at least one region of the antibody, in some instances, vary in length or sequence. In some instances, the at least one region that is de novo synthesized is for CDRH1, CDRH2, CDRH3, CDRL1, CDRL2, CDRL3, VL, VH, or combinations thereof. In some instances, the at least one region that is de novo synthesized is for framework element 1 (FW1), framework element 2 (FW2), framework element 3 (FW3), or framework element 4 (FW4). In some instances, the variant sequence comprises at least or about 1, 2, 3, 4, 5, 6, 7, 8, 9, 10, 15, 20, 25, 30, 35, 40, 45, 50, or more than 50 variant nucleotides or amino acids as compared to wild-type. In some instances, the variant sequence comprises at least or about 1, 2, 3, 4, 5, 6, 7, 8, 9, 10, 15, 20, 25, 30, 35, 40, 45, 50 additional nucleotides or amino acids as compared to wild-type. In some instances, the variant sequence comprises at least or about 1, 2, 3, 4, 5, 6, 7, 8, 9, 10, 15, 20, 25, 30, 35, 40, 45, or 50 less nucleotides or amino acids as compared to wild-type. In some instances, the libraries comprise at least or about $10^1$, $10^2$, $10^3$, $10^4$, $10^5$, $10^6$, $10^7$, $10^8$, $10^9$, $10^{10}$, or more than $10^{10}$ variants.

Following synthesis of antibody libraries, antibody libraries may be used for screening and analysis. For example, antibody libraries are assayed for library displayability and panning. In some instances, displayability is assayed using a selectable tag. Exemplary tags include, but are not limited to, a radioactive label, a fluorescent label, an enzyme, a chemiluminescent tag, a colorimetric tag, an affinity tag or other labels or tags that are known in the art. In some instances, the tag is histidine, polyhistidine, myc, hemagglutinin (HA), or FLAG. For example, as seen in FIG. 2B. In some instances, antibody libraries are assayed by sequencing using various methods including, but not limited to, single-molecule real-time (SMRT) sequencing, Polony sequencing, sequencing by ligation, reversible terminator sequencing, proton detection sequencing, ion semiconductor sequencing, nanopore sequencing, electronic sequencing, pyrosequencing, Maxam-Gilbert sequencing, chain termination (e.g., Sanger) sequencing, +S sequencing, or sequencing by synthesis. In some instances, antibody libraries are displayed on the surface of a cell or phage. In some instances, antibody libraries are enriched for sequences with a desired activity using phage display.

In some instances, the antibody libraries are assayed for functional activity, structural stability (e.g., thermal stable or pH stable), expression, specificity, or a combination thereof. In some instances, the antibody libraries are assayed for antibody capable of folding. In some instances, a region of the antibody is assayed for functional activity, structural stability, expression, specificity, folding, or a combination thereof. For example, a VH region or VL region is assayed for functional activity, structural stability, expression, specificity, folding, or a combination thereof.

Antibodies or IgGs generated by methods as described herein comprise improved binding affinity. In some instances, the antibody comprises a binding affinity (e.g., $K_D$) of less than 1 nM, less than 1.2 nM, less than 2 nM, less than 5 nM, less than 10 nM, less than 11 nm, less than 13.5 nM, less than 15 nM, less than 20 nM, less than 25 nM, or less than 30 nM. In some instances, the antibody comprises a $K_D$ of less than 400 nM, less than 350 nM, less than 300 nM, less than 250 nM, less than 200 nM, less than 150 nm, less than 100 nM, less than 50 nM, less than 25 nM, less than 15 nM, or less than 10 nM. In some instances, the antibody comprises a $K_D$ of less than 1 nM. In some instances, the antibody comprises a $K_D$ of less than 1.2 nM. In some instances, the antibody comprises a $K_D$ of less than 2 nM. In some instances, the antibody comprises a $K_D$ of less than 5 nM. In some instances, the antibody comprises a $K_D$ of less than 10 nM. In some instances, the antibody comprises a $K_D$ of less than 13.5 nM. In some instances, the antibody comprises a $K_D$ of less than 15 nM. In some instances, the antibody comprises a $K_D$ of less than 20 nM. In some instances, the antibody comprises a $K_D$ of less than 25 nM. In some instances, the antibody comprises a $K_D$ of less than 30 nM.

In some instances, the affinity of antibodies or IgGs generated by methods as described herein is at least or about 1.5×, 2.0×, 5×, 10×, 20×, 30×, 40×, 50×, 60×, 70×, 80×, 90×, 100×, 200×, or more than 200× improved binding affinity as compared to a comparator antibody. In some instances, the affinity of antibodies or IgGs generated by methods as described herein is at least or about 1.5×, 2.0×, 5×, 10×, 20×, 30×, 40×, 50×, 60×, 70×, 80×, 90×, 100×, 200×, or more than 200× improved function as compared to a comparator antibody. In some instances, the comparator antibody is an antibody with similar structure, sequence, or antigen target.

In some embodiments, the variant antibodies or IgGs generated by methods as described herein result in a decreased $EC_{50}$ in a T-cell cytotoxicity assay as compared to the $EC_{50}$ in a T-cell cytotoxicity assay of a reference antibody or IgG. In some embodiments, the variant antibodies or IgGs have an $EC_{50}$ in a T-cell cytotoxicity assay that is at least 5× decreased as compared to the $EC_{50}$ in a T-cell cytotoxicity assay of a reference antibody or IgG. In some embodiments, the variant antibodies or IgGs have an $EC_{50}$ in a T-cell cytotoxicity assay that is at least 8× decreased as compared to the $EC_{50}$ in a T-cell cytotoxicity assay of a reference antibody or IgG. In some embodiments, the variant antibodies or IgGs have an $EC_{50}$ in a T-cell cytotoxicity assay that is at least 10× decreased as compared to the $EC_{50}$ in a T-cell cytotoxicity assay of a reference antibody or IgG. In some embodiments, the variant antibodies or IgGs have an $EC_{50}$ in a T-cell cytotoxicity assay that is at least 20× decreased as compared to the $EC_{50}$ in a T-cell cytotoxicity assay of a reference antibody or IgG. In some embodiments, the variant antibodies or IgGs have an $EC_{50}$ in a T-cell cytotoxicity assay that is at least 25× decreased as compared to the $EC_{50}$ in a T-cell cytotoxicity assay of a reference antibody or IgG. In some embodiments, the variant antibodies or IgGs have an $EC_{50}$ in a T-cell cytotoxicity assay that is at least 30× decreased as compared to the $EC_{50}$ in a T-cell cytotoxicity assay of a reference antibody or IgG. In some embodiments, the variant antibodies or IgGs have an $EC_{50}$ in a T-cell cytotoxicity assay that is at least 40× decreased as compared to the $EC_{50}$ in a T-cell cytotoxicity assay of a reference antibody or IgG. In some embodiments, the variant antibodies or IgGs have an $EC_{50}$ in a T-cell cytotoxicity assay that is at least 50× decreased as compared to the $EC_{50}$ in a T-cell cytotoxicity assay of a reference antibody or IgGs.

Methods as described herein, in some instances, result in increased yield of antibodies ax IgGs. In some instances, the yield is at least or about 5, 10, 15, 20, 25, 30, 35, 40, 45, 50, 55, 60, 65, 70, 75, 80, or more than 80 micrograms (ug). In some instances, the yield is in a range of about 5 to about 80, about 10 to about 75, about 15 to about 60, about 20 to about 50, or about 30 to about 40 micrograms (ug).

Expression Systems

Provided herein are libraries comprising nucleic acids encoding for antibody comprising binding domains, wherein the libraries have improved specificity, stability, expression, folding, or downstream activity. In some instances, libraries described herein are used for screening and analysis.

Provided herein are libraries comprising nucleic acids encoding for antibody comprising binding domains, wherein the nucleic acid libraries are used for screening and analysis. In some instances, screening and analysis comprises in vitro, in vivo, or ex vivo assays. Cells for screening include primary cells taken from living subjects or cell lines. Cells may be from prokaryotes (e.g., bacteria and fungi) or eukaryotes (e.g., animals and plants). Exemplary animal cells include, without limitation, those from a mouse, rabbit, primate, and insect. In some instances, cells for screening include a cell line including, but not limited to, Chinese Hamster Ovary (CHO) cell line, human embryonic kidney (HEK) cell line, or baby hamster kidney (BHK) cell line. In some instances, nucleic acid libraries described herein may also be delivered to a multicellular organism. Exemplary multicellular organisms include, without limitation, a plant, a mouse, rabbit, primate, and insect.

Nucleic acid libraries described herein may be screened for various pharmacological or pharmacokinetic properties. In some instances, the libraries are screened using in vitro assays, in vivo assays, or ex vivo assays. For example, in vitro pharmacological or pharmacokinetic properties that are screened include, but are not limited to, binding affinity, binding specificity, and binding avidity. Exemplary in vivo pharmacological or pharmacokinetic properties of libraries described herein that are screened include, but are not limited to, therapeutic efficacy, activity, preclinical toxicity properties, clinical efficacy properties, clinical toxicity properties, immunogenicity, potency, and clinical safety properties.

Provided herein are nucleic acid libraries, wherein the nucleic acid libraries may be expressed in a vector. Expression vectors for inserting nucleic acid libraries disclosed herein may comprise eukaryotic or prokaryotic expression vectors. Exemplary expression vectors include, without limitation, mammalian expression vectors: pSF-CMV-NEO-NH2-PPT-3XFLAG, pSF-CMV-NEO-COOH-3XFLAG, pSF-CMV-PURO-NH2-GST-TEV, pSF-OXB20-COOH-TEV-FLAG(R)-6His ("6His" disclosed as SEQ ID NO: 45), pCEP4 pDEST27, pSF-CMV-Ub-KrYFP, pSF-CMV-FMDV-daGFP, pEF1a-mCherry-N1 Vector, pEF1a-tdTomato Vector, pSF-CMV-FMDV-Hygro, pSF-CMV-PGK-Puro, pMCP-tag(m), and pSF-CMV-PURO-NH2-CMYC; bacterial expression vectors: pSF-OXB20-BetaGal,pSF-OXB20-Fluc, pSF-OXB20, and PSF-Tac; plant expression vectors: pRI 101-AN DNA and pCambia2301; and yeast expression vectors: pTVB21 and pKLAC2, and insect vectors: pAc5.1/V-5-His A and pDEST8. In some instances, the vector is pcDNA3 or pcDNA3.1.

Described herein are nucleic acid libraries that are expressed in a vector to generate a construct comprising an antibody. In some instances, a size of the construct varies. In some instances, the construct comprises at least or about 500, 600, 700, 800, 900, 1000, 1100, 1300, 1400, 1500, 1600, 1700, 1800, 2000, 2400, 2600, 2800, 3000, 3200, 3400, 3600, 3800, 4000, 4200, 4400, 4600, 4800, 5000, 6000, 7000, 8000, 9000, 10000, or more than 10000 bases. In some instances, the construct comprises a range of about 300 to 1,000, 300 to 2,000, 300 to 3,000, 300 to 4,000, 300 to 5,000, 300 to 6,000, 300 to 7,000, 300 to 8,000, 300 to 9,000, 300 to 10,000, 1,000 to 2,000, 1,000 to 3,000, 1,000 to 4,000, 1,000 to 5,000, 1,000 to 6,000, 1,000 to 7,000, 1,000 to 8,000, 1,000 to 9,000, 1,000 to 10,000, 2,000 to 3,000, 2,000 to 4,000, 2,000 to 5,000, 2,000 to 6,000, 2,000 to 7,000, 2,000 to 8,000, 2,000 to 9,000, 2,000 to 10,000, 3,000 to 4,000, 3,000 to 5,000, 3,000 to 6,000, 3,000 to 7,000, 3,000 to 8,000, 3,000 to 9,000, 3,000 to 10,000, 4,000 to 5,000, 4,000 to 6,000, 4,000 to 7,000, 4,000 to 8,000, 4,000 to 9,000, 4,000 to 10,000, 5,000 to 6,000, 5,000 to 7,000, 5,000 to 8,000, 5,000 to 9,000, 5,000 to 10,000, 6,000 to 7,000, 6,000 to 8,000, 6,000 to 9,000, 6,000 to 10,000, 7,000 to 8,000, 7,000 to 9,000, 7,000 to 10,000, 8,000 to 9,000, 8,000 to 10,000, or 9,000 to 10,000 bases.

Provided herein are libraries comprising nucleic acids encoding for antibodies, wherein the nucleic acid libraries are expressed in a cell. In some instances, the libraries are synthesized to express a reporter gene. Exemplary reporter genes include, but are not limited to, acetohydroxyacid synthase (AHAS), alkaline phosphatase (AP), beta galactosidase (LacZ), beta glucoronidase (GUS), chloramphenicol acetyltransferase (CAT), green fluorescent protein (GFP), red fluorescent protein (RFP), yellow fluorescent protein (YFP), cyan fluorescent protein (CFP), cerulean fluorescent protein, citrine fluorescent protein, orange fluorescent protein, cherry fluorescent protein, turquoise fluorescent protein, blue fluorescent protein, horseradish peroxidase (HRP), luciferase (Luc), nopaline synthase (NOS), octopine synthase (OCS), luciferase, and derivatives thereof. Methods to determine modulation of a reporter gene are well known in the art, and include, but are not limited to, fluorometric methods (e.g. fluorescence spectroscopy, Fluorescence Activated Cell Sorting (FACS), fluorescence microscopy), and antibiotic resistance determination.

Diseases and Disorders

Provided herein are libraries comprising nucleic acids encoding for antibodies or immunoglobulins that may have therapeutic effects. In some instances, the antibodies or immunoglobulin result in protein when translated that is used to treat a disease or disorder in a subject. Exemplary diseases include, but are not limited to, cancer, inflammatory diseases or disorders, a metabolic disease or disorder, a cardiovascular disease or disorder, a respiratory disease or disorder, pain, a digestive disease or disorder, a reproductive disease or disorder, an endocrine disease or disorder, or a neurological disease or disorder. In some instances, the cancer is a solid cancer or a hematologic cancer. In some instances, the disease or disorder is an autoimmune disease. In some instances, the disease or disorder is diabetes. In some instances, the disease or disorder is Type I diabetes. In some instances, the subject is a mammal. In some instances, the subject is a mouse, rabbit, dog, or human. Subjects treated by methods described herein may be infants, adults, or children. Pharmaceutical compositions comprising antibodies or antibody fragments as described herein may be administered intravenously or subcutaneously.

In some instances, the disease or disorder is associated with CD3 dysfunction. In some instances, the disease or disorder is associated with aberrant signaling via CD3. In some instances, the disease or disorder is cancer. In some instances, the disease or disorder is a viral infection. In some instances, the disease or disorder is an autoimmune disease. In some instances, the disease or disorder is diabetes. In some instances, the disease or disorder is Type I diabetes.

Protein Targets

Provided herein are libraries comprising nucleic acids encoding for antibodies or immunoglobulins that target Cluster of Differentiation 3 (CD3). In some instances, the libraries comprise nucleic acids encoding for antibodies or immunoglobulins that target Cluster of Differentiation 3 epsilon (CD3ε).

Provided herein are CD3 antibodies or immunoglobulins, wherein the CD3 antibody or immunoglobulin comprises a sequence at least or about 70%, 80%, 85%, 90%, 91%, 92%, 93%, 94%, 95%, 96%, 97%, 98%, 99%, or 100% sequence identity to any one of SEQ NOs: 1-32, some instances, the antibody or immunoglobulin sequence comprises at least or about 95% sequence identity to any one of SEQ ID NOs: 1-32. In some instances, the antibody or immunoglobulin sequence comprises at least or about 97% sequence identity to any one of SE ID NOs: 1-32. In some instances, the antibody or immunoglobulin sequence comprises at least or about 99% sequence identity to any one of SEQ ID NOs: 1-32. In some instances, the antibody or immunoglobulin sequence comprises at least or about 100% sequence identity to any one SEQ ID NOs: 1-32. In some instances, the antibody or immunoglobulin sequence comprises at least a portion having at least or about 1, 2, 3, 4, 5, 6, 7, 8, 9, 10, 12, 14, 16, 18, 20, 30, 40, 50, 60, 70, 80, 90, 100, 110, 120, 130, 140, 150, or more than 150 amino acids of any one of SEQ ID NOs: 1-32.

In some embodiments, the CD3 antibody or immunoglobulin sequence comprises complementarity determining regions (CDRs) comprising at least or about 70%, 80%, 85%, 90%, 91%, 92%, 93%, 94%, 95%, 96%, 97%, 98%, 99%, or 100% sequence identity to any one of SEQ ID NOs: 1-20. In some instances, the antibody or immunoglobulin sequence comprises complementarily determining regions (CDRs) comprising at least or about 95% homology to any one of SEQ ID NOs: 1-20. In some instances, the antibody or immunoglobulin sequence comprises complementarity determining regions (CDRs) comprising at least or about 97% homology to any one of SEQ ID NOs: 1-20. In some instances, the antibody or immunoglobulin sequence comprises complementarity determining regions (CDRs) comprising at least or about 99% homology to any one of SEQ ID NOs: 1-20. In some instances, the antibody or immunoglobulin sequence comprises complementarity determining regions (CDRs) comprising at least or about 100% homology to any one of SEQ ID NOs: 1-20. In some instances, the antibody or immunoglobulin sequence comprises complementarity determining regions (CDRs) comprising at least a portion having at least or about 3, 4, 5, 6, 7, 8, 9, 10, 12, 14, 16, or more than 16 amino acids of any one of SEQ ID NOs: 1-20.

In some embodiments, the CD3 antibody or immunoglobulin sequence comprises a CDR1 comprising at least or about 70%, 80%, 85%, 90%, 91%, 92%, 93%, 94%, 95%, 96%, 97%, 98%, 99%, or 100% sequence identity to any one of SEQ NOs: 1-3 or 12-14. In some instances, the antibody or immunoglobulin sequence comprises CDR1 comprising at least or about 95% homology of any one of SEQ ID NOs: 1-3 or 12-14. In some instances, the antibody or immunoglobulin sequence comprises CDR1 comprising at least or about 97% homology to any one of SEQ ID NOs: 1-3 or 12-14. In some instances, the antibody or immunoglobulin sequence comprises CDR1 comprising at least or about 99% homology to any one of SEQ ID NOs: 1-3 or 12-14. In some instances, the antibody or immunoglobulin sequence comprises CDR1 comprising at least or about 100% homology to any one of SEQ ID NOs: 1-3 or 12-14. In some instances, the antibody or immunoglobulin sequence comprises CDR1 comprising at least a portion having at least or about 3, 4, 5, 6, 7, 8, 9, 10, 12, 14, 16, or more than 16 amino acids of any one of SEQ ID NOs: 1-3 or 12-14.

In some embodiments, the CD3 antibody or immunoglobulin sequence comprises a CDR2 comprising at least or about 70%, 80%, 85%, 90%, 91%, 92%, 93%, 94%, 95%, 96%, 97%, 98%, 99%, or 100% sequence identity to any one of SEQ ID NOs: 4-6 or 15-17. In some instances, the antibody or immunoglobulin sequence comprises CDR2 comprising at least or about 95% homology to any one of SEQ D NOs: 4-6 or 15-17. In some instances, the antibody or immunoglobulin sequence comprises CDR2 comprising at least or about 97% homology to any one of SEQ ID NOs: 4-6 or 15-17. In some instances, the antibody or immunoglobulin sequence comprises CDR2 comprising at least or about 99% homology to any one of SEQ ID NOs: 4-6 or 15-17. In some instances, the antibody or immunoglobulin sequence comprises CDR2 comprising at least or about 100% homology to any one of SEQ ID NOs: 4-6 or 15-17. In some instances, the antibody or immunoglobulin sequence comprises CDR2 comprising at least a portion having at least or about 3, 4, 5, 6, 7, 8, 9, 10, 12, 14, 16, or more than 16 amino acids of any one of SEQ ID NOs: 4-6 or 15-17.

In some embodiments, the CD3 antibody or immunoglobulin sequence comprises a CDR3 comprising at least or about 70%, 80%, 85%, 90%, 91%, 92%, 93%, 94%, 95%, 96%, 97%, 98%, 99%, or 100% sequence identity to any one of SEQ ID NOs: 7-11 or 18-20. In some instances, the antibody or immunoglobulin sequence comprises CDR3 comprising at least or about 95% homology to any one of SEQ NOs: 7-11 or 18-20, in some instances, the antibody or immunoglobulin sequence comprises CDR3 comprising at least or about 97% homology to any one of SEQ ID NOs: 7-11 or 18-20. In some instances, the antibody or immunoglobulin sequence comprises CDR3 comprising at least or about 99% homology to any one of SEQ ID NOs: 7-11 or 18-20. In some instances, the antibody or immunoglobulin sequence comprises CDR3 comprising at least or about 100% homology to any one of SEQ ID NOs: 7-11 or 18-20. In some instances, the antibody or immunoglobulin sequence comprises CDR3 comprising at least a portion having at least or about 3, 4, 5, 6, 7, 8, 9, 10, 12, 14, 16, or more than 16 amino acids of any one of SEQ ID NOs: 7-11 or 18-20.

In some embodiments, the CD3 antibody or immunoglobulin sequence comprises a CDRH1 comprising at least or about 70%, 80%, 85%, 90%, 91%, 92%, 93%, 94%, 95%, 96%, 97%, 98%, 99%, or 100% sequence identity to SEQ ID NO: 1; a CDRH2 comprising at least or about 70%, 80%, 85%, 90%, 91%, 92%, 93%, 94%, 95%, 96%, 97%, 98%, 99%, or 100% sequence identity to SEQ ID NO: 4; and a CDRH3 comprising at least or about 70%, 80%, 85%, 90%, 91%, 92%, 93%, 94%, 95%, 96%, 97%, 98%, 99%, or 100% sequence identity to SEQ ID NO: 7. In some instances, the antibody or immunoglobulin sequence comprises CDRH1 comprising at least or about 95%, 97%, 99%, or 100% homology to SEQ ID NO: 1; a CDRH2 comprising at least or about 95%, 97%, 99%, or 100% homology to SEQ ID NO: 4; and a CDRH3 comprising at least or about 95%, 97%, 99%, or 100% homology to SEQ ID NO: 7. In some instances, the antibody or immunoglobulin sequence comprises CDRH1 comprising at least a portion having at least or about 3, 4, 5, 6, 7, 8, 9, 10, 12, 14, 16, or more than 16 amino acids of SEQ ID NO: 1; a CDRH2 comprising at least a portion having at least or about 3, 4, 5, 6, 7, 8, 9, 10, 12, 14, 16, or more than 16 amino acids of SEQ ID NO: 4; and a CDRH3 comprising at least a portion having at least or about 3, 4, 5, 6, 7, 8, 9, 10, 12, 14, 16, or more than 16 amino acids of SEQ ID NO: 7.

In some embodiments, the CD3 antibody or immunoglobulin sequence comprises a CDRH1 comprising at least or about 70%, 80%, 85%, 90%, 91%, 92%, 93%, 94%, 95%, 96%, 97%, 98%, 99%, or 100% sequence identity to SEQ ID NO: 2; a CDRH2 comprising at least or about 70%, 80%, 85%, 90%, 91%, 92%, 93%, 94%, 95%, 96%, 97%, 98%, 99%, or 100% sequence identity to SEQ ID NO: 5; and a CDRH3 comprising at least or about 70%, 80%, 85%, 90%, 91%, 92%, 93%, 94%, 95%, 96%, 97%, 98%, 99%, or 100% sequence identity to SEQ NO: 8. In some instances, the antibody or immunoglobulin sequence comprises CDRH1 comprising at least or about 95%, 97%, 99%, or 100% homology to SEQ ID NO: 2; a CDRH2 comprising at least or about 95%, 97%, 99%, or 100% homology to SEQ ID NO: 5; and a CDRH3 comprising at least or about 95%, 97%, 99%, or 100% homology to SEQ ID NO: 8. In some instances, the antibody or immunoglobulin sequence comprises CDRH1 comprising at least a portion having at least or about 3, 4, 5, 6, 7, 8, 9, 10, 12, 14, 16, or more than 16 amino acids of SEQ ID NO: 2; a CDRH2 comprising at least a portion having at least or about 3, 4, 5, 6, 7, 8, 9, 10, 12, 14, 16, or more than 16 amino acids of SEQ ID NO: 5; and a CDRH3 comprising at least a portion having at least or about 3, 4, 5, 6, 7, 8, 9, 10, 12, 14, 16, or more than 16 amino acids of SEQ ID NO: 8.

In some embodiments, the CD3 antibody or immunoglobulin sequence comprises a CDRH1 comprising at least or about 70%, 80%, 85%, 90%, 91%, 92%, 93%, 94%, 95%, 96%, 97%, 98%, 99%, or 100% sequence identity to SEQ ID NO: 3; a CDRH2 comprising at least or about 70%, 80%, 85%, 90%, 91%, 92%, 93%, 94%, 95%, 96%, 97%, 98%, 99%, or 100% sequence identity to SEQ ID NO: 6; and a CDRH3 comprising at least or about 70%, 80%, 85%, 90%, 91%, 92%, 93%, 94%, 95%, 96%, 97%, 98%, 99%, or 100% sequence identity to SEQ ID NO: 9. In some instances, the antibody or immunoglobulin sequence comprises CDRH1 comprising at least or about 95%, 97%, 99%, or 100% homology to SEQ ID NO: 3; a CDRH2 comprising at least or about 95%, 97%, 99%, or 100% homology to SEQ ID NO: 6; and a CDRH3 comprising at least or about 95%, 97%, 99%, or 100% homology to SEQ ID NO: 9. In some instances, the antibody or immunoglobulin sequence comprises CDRH1 comprising at least a portion having at least or about 3, 4, 5, 6, 7, 8, 9, 10, 12, 14, 16, or more than 16 amino acids of SEQ ID NO: 3; a CDRH2 comprising at least a portion having at least or about 3, 4, 5, 6, 7, 8, 9, 10, 12, 14, 16, or more than 16 amino acids of SEQ ID NO: 6; and a CDRH3 comprising at least a portion having at least or about 3, 4, 5, 6, 7, 8, 9, 10, 12, 14, 16, or more than 16 amino acids of SEQ ID NO: 9.

In some embodiments, the CD3 antibody or immunoglobulin sequence comprises a CDRL1 comprising at least or about 70%, 80%, 85%, 90%, 91%, 92%, 93%, 94%, 95%, 96%, 97%, 98%, 99%, or 100% sequence identity to SEQ ID NO: 12; a CDRL2 comprising at least or about 70%, 80%, 85%, 90%, 91%, 92%, 93%, 94%, 95%, 96%, 97%, 98%, 99%, or 100% sequence identity to SEQ ID NO: 15; and a CDRL3 comprising at least or about 70%, 80%, 85%, 90%, 91%, 92%, 93%, 94%, 95%, 96%, 97%, 98%, 99%, or 100% sequence identity to SEQ ID NO: 18. In some instances, the antibody or immunoglobulin sequence comprises CDRL1 comprising at least or about 95%, 97%, 99%, or 100% homology to SEQ ID NO: 12; a CDRL2 comprising at least or about 95%, 97%, 99%, or 100% homology to SEQ ID NO: 15; and a CDRL3 comprising at least or about 95%, 97%, 99%, or 100% homology to SEQ ID NO: 18. In some instances, the antibody or immunoglobulin sequence comprises CDRL1 comprising at least a portion having at least or about 3, 4, 5, 6, 7, 8, 9, 10, 12, 14, 16, or more than 16 amino acids of SEQ ID NO: 12; a CDRL2 comprising at least a portion having at least or about 3, 4, 5, 6, 7, 8, 9, 10, 12, 14, 16, or more than 16 amino acids of SEQ ID NO: 15; and a CDRL3 comprising at least a portion having at least or about 3, 4, 5, 6, 7, 8, 9, 10, 12, 14, 16, or more than 16 amino acids of SEQ ID NO: 18.

In some embodiments, the CD3 antibody or immunoglobulin sequence comprises a CDRL1 comprising at least or about 70%, 80%, 85%, 90%, 91%, 92%, 93%, 94%, 95%, 96%, 97%, 98%, 99%, or 100% sequence identity to SEQ ID NO: 13; a CDRL2 comprising at least or about 70%, 80%, 85%, 90%, 91%, 92%, 93%, 94%, 95%, 96%, 97%, 98%, 99%, or 100% sequence identity to SEQ ID NO: 16; and a CDRL3 comprising at least or about 70%, 80%, 85%, 90%, 91%, 92%, 93%, 94%, 95%, 96%, 97%, 98%, 99%, or 100% sequence identity to SEQ ID NO: 19. In some instances, the antibody or immunoglobulin sequence comprises CDRL1 comprising at least or about 95%, 97%, 99%, or 100% homology to SEQ ID NO: 13; a CDRL2 comprising at least or about 95%, 97%, 99%, or 100% homology to SEQ ID NO: 16; and a CDRL3 comprising at least or about 95%, 97%, 99%, or 100% homology to SEQ ID NO: 19. In some instances, the antibody or immunoglobulin sequence comprises CDRL1 comprising at least a portion having at least or about 3, 4, 5, 6, 7, 8, 9, 10, 12, 14, 16, or more than 16 amino acids of SEQ ID NO: 13; a CDRL2 comprising at least a portion having at least or about 3, 4, 5, 6, 7, 8, 9, 10, 12, 14, 16, or more than 16 amino acids of SEQ ID NO: 16; and a CDRL3 comprising at least a portion having at least or about 3, 4, 5, 6, 7, 8, 9, 10, 12, 14, 16; or more than 16 amino acids of SEQ ID NO: 19.

In some embodiments, the CD3 antibody or immunoglobulin sequence comprises a CDRL1 comprising at least or about 70%, 80%, 85%, 90%, 91%, 92%, 93%, 94%, 95%, 96%, 97%, 98%, 99%, or 100% sequence identity to SEQ ID NO: 14; a CDRL2 comprising at least or about 70%, 80%, 85%, 90%, 91%, 92%, 93%, 94%, 95%, 96%, 97%, 98%, 99%, or 100% sequence identity to SEQ ID NO: 17; and a CDRL3 comprising at least or about 70%, 80%, 85%, 90%, 91%, 92%, 93%, 94%, 95%, 96%, 97%, 98%, 99%, or 100% sequence identity to SEQ ID NO: 20. In some instances, the antibody or immunoglobulin sequence comprises CDRL1 comprising at least or about 95%, 97%, 99%, or 100% homology to SEQ ID NO: 14; a CDRL2 comprising at least or about 95%, 97%, 99%, or 100% homology to SEQ ID NO: 17; and a CDRL3 comprising at least or about 95%, 97%, 99%, or 100% homology to SEQ ID NO: 20. In some instances, the antibody or immunoglobulin sequence comprises CDRL1 comprising at least a portion having at least or about 3, 4, 5, 6, 7, 8, 9, 10, 12, 14, 16, or more than 16 amino acids of SEQ ID NO: 14; a CDRL2 comprising at least a portion having at least or about 3, 4, 5, 6, 7, 8, 9, 10, 12, 14, 16, or more than 16 amino acids of SEQ ID NO: 17; and a CDRL3 comprising at least a portion having at least or about 3, 4, 5, 6, 7, 8, 9, 10, 12, 14, 16, or more than 16 amino acids of SEQ ID NO: 20.

In some embodiments, the antibody or immunoglobulin sequence comprises a CDRH1 comprising at least or about 70%, 80%, 85%, 90%, 91%, 92%, 93%, 94%, 95%, 96%, 97%, 98%, 99%, or 100% sequence identity to SEQ ID NO: 1; a CDRH2 comprising at least or about 70%, 80%, 85%, 90%, 91%, 92%, 93%, 94%, 95%, 96%, 97%, 98%, 99%, or 100% sequence identity to SEQ ID NO: 4; a CDRH3 comprising at least or about 70%, 80%, 85%, 90%, 91%, 92%, 93%, 94%, 95%, 96%, 97%, 98%, 99%, or 100% sequence identity to SEQ ID NO: 7, a CDRL1 comprising at least or about 70%, 80%, 85%, 90%, 91%, 92%, 93%, 94%, 95%, 96%, 97%, 98%, 99%, or 100% sequence identity to SEQ ID NO: 12; a CDRL2 comprising at least or about 70%, 80%, 85%, 90%, 91%, 92%, 93%, 94%, 95%, 96%, 97%, 98%, 99%, or 100% sequence identity to SEQ ID NO: 15; and a CDRL3 comprising at least or about 70%, 80%, 85%, 90%, 91%, 92%, 93%, 94%, 95%, 96%, 97%, 98%, 99%, or 100% sequence identity to SEQ ID NO: 18. In some instances, the antibody or immunoglobulin sequence comprises CDRH1 comprising at least or about 95%, 97%, 99%, or 100% homology to SEQ ID NO: 1; a CDRH2 comprising at least or about 95%, 97%, 99%, or 100% homology to SEQ ID NO: 4; a CDRH3 comprising at least or about 95%, 97%, 99%, or 100% homology to SEQ ID NO: 7; a CDRL1 comprising at least or about 95%, 97%, 99%, or 100% homology to SEQ ID NO: 12; a CDRL2 comprising at least or about 95%, 97%, 99%, or 100% homology to SEQ ID NO: 15; and a CDRL3 comprising at least or about 95%, 97%, 99%, or 100% homology to SEQ ID NO: 18. In some instances, the antibody or immunoglobulin sequence comprises CDRH1 comprising at least a portion having at least or about 3, 4, 5, 6, 7, 8, 9, 10, 12, 14, 16, or more than 16 amino acids of SEQ ID NO: 1; a CDRH2 comprising at least a portion having at least or about 3, 4, 5, 6, 7, 8, 9, 10, 12, 14, 16, or more than 16 amino acids of SEQ ID NO: 4; a CDRH3 comprising at least a portion having at least or about 3, 4, 5, 6, 8, 9, 10, 12, 14, 16, or more than 16 amino acids of SEQ ID NO: 7; a CDRL1 comprising at least a portion having at least or about 3, 4, 5, 6, 7, 8, 9, 10, 12, 14, 16, or more than 16 amino acids of SEQ ID NO: 12; a CDRL2 comprising at least a portion having at least or about 3, 4, 5, 6, 7, 8, 9, 10, 12, 14, 16, or more than 16 amino acids of SEQ ID NO: 15; and a CDRL3 comprising at least a portion having at least or about 3, 4, 5, 6, 7, 8, 9, 10, 12, 14, 16, or more than 16 amino acids of SEQ ID NO: 18.

In some embodiments, the antibody or immunoglobulin sequence comprises a CDRH1 comprising at least or about 70%, 80%, 85%, 90%, 91%, 92%, 93%, 94%, 95%, 96%, 97%, 98%, 99%, or 100% sequence identity to SEQ ID NO: 2; a CDRH2 comprising at least or about 70%, 80%, 85%, 90%, 91%, 92%, 93%, 94%, 95%, 96%, 97%, 98%, 99%, or 100% sequence identity to SEQ ID NO: 5; a CDRH3 comprising at least or about 70%, 80%, 85%, 90%, 91%, 92%, 93%, 94%, 95%, 96%, 97%, 98%, 99%, or 100% sequence identity to SEQ ID NO: 8, a CDRL1 comprising at least or about 70%, 80%, 85%, 90%, 91%, 92%, 93%, 94%, 95%, 96%, 97%, 98%, 99%, or 100% sequence identity to SEQ ID NO: 13; a CDRL2 comprising at least or about 70%, 80%, 85%, 90%, 91%, 92%, 93%, 94%, 95%, 96%, 97%, 98%, 99%, or 100% sequence identity to SEQ ID NO: 16; and a CDRL3 comprising at least or about 70%, 80%, 85%, 90%, 91%, 92%, 93%, 94%, 95%, 96%, 97%, 98%, 99%, or 100% sequence identity to SEQ ID NO: 19. In some instances, the antibody or immunoglobulin sequence comprises CDRH1 comprising at least or about 95%, 97%, 99%, or 100% homology to SEQ ID NO: 2; a CDRH2 comprising at least or about 95%, 97%, 99%, or 100% homology to SEQ ID NO: 5; a CDRH3 comprising at least or about 95%, 97%, 99%, or 100% homology to SEQ ID NO: 8; a CDRL1 comprising at least or about 95%, 97%, 99%, or 100% homology to SEQ ID NO: 13; a CDRL2 comprising at least or about 95%, 97%, 99%, or 100% homology to SEQ ID NO: 16; and a CDRL3 comprising at least or about 95%, 97%, 99%, or 100% homology to SEQ ID NO: 19. In some instances, the antibody or immunoglobulin sequence comprises CDRH1 comprising at least a portion having at least or about 3, 4, 5, 6, 7, 8, 9, 10, 12, 14, 16, or more than 16 amino acids of SEQ ID NO: 2; a CDRH2 comprising at least a portion having at least or about 3, 4, 5, 6, 7, 8, 9, 10, 12, 14, 16, or more than 16 amino acids of SEQ ID NO: 5; a CDRH3 comprising at least a portion having at least or about 3, 4, 5, 6, 7, 8, 9, 10, 12, 14, 16, or more than 16 amino acids of SEQ ID NO: 8; a CDRL1 comprising at least a portion having at least or about 3, 4, 5, 6, 7, 8, 9, 10, 12, 14, 16, or more than 16 amino acids of SEQ ID NO: 13; a CDRL2 comprising at least a portion having at least or about 3, 4, 5, 6, 7, 8, 9, 10, 12, 14, 16, or more than 16 amino acids of SEQ ID NO: 16; and a CDRL3 comprising at least a portion having at least or about 3, 4, 5, 6, 7, 8, 9, 10, 12, 14, 16, or more than 16 amino acids of SEQ ID NO: 19.

In some embodiments, the antibody or immunoglobulin sequence comprises a CDRH1 comprising at least or about 70%, 80%, 85%, 90%, 91%, 92%, 93%, 94%, 95%, 96%, 97%, 98%, 99%, or 100% sequence identity to SEQ ID NO: 3; a CDRH2 comprising at least or about 70%, 80%, 85%, 90%, 91%, 92%, 93%, 94%, 95%, 96%, 97%, 98%, 99%, or 100% sequence identity to SEQ ID NO: 6; a CDRH3 comprising at least or about 70%, 80%, 85%, 90%, 91%, 92%, 93%, 94%, 95%, 96%, 97%, 98%, 99%, or 100% sequence identity to SEQ ID NO: 9, a CDRL1 comprising at least or about 70%, 80%, 85%, 90%, 91%, 92%, 93%, 94%, 95%, 96%, 97%, 98%, 99%, or 100% sequence identity to SEQ ID NO: 14; a CDRL2 comprising at least or about 70%, 80%, 85%, 90%, 91%, 92%, 93%, 94%, 95%, 96%, 97%, 98%, 99%, or 100% sequence identity to SEQ ID NO: 17; and a CDRL3 comprising at least or about 70%, 80%, 85%, 90%, 91%, 92%, 93%, 94%, 95%, 96%, 97%, 98%, 99%, or 100% sequence identity to SEQ ID NO: 20. In some instances, the antibody or immunoglobulin sequence comprises CDRH1 comprising at least or about 95%, 97%, 99%, or 100% homology to SEQ ID NO: 3; a CDRH2 comprising at least or about 95%, 97%, 99%, or 100% homology to SEQ ID NO: 6; a CDRH3 comprising at least or about 95%, 97%, 99%, or 100% homology to SEQ ID NO: 9; a CDRL1 comprising at least or about 95%, 97%, 99%, or 100% homology to SEQ ID NO: 14; a CDRL2 comprising at least or about 95%, 97%, 99%, or 100% homology to SEQ ID NO: 17; and a CDRL3 comprising at least or about 95%, 97%, 99%, or 100% homology to SEQ ID NO: 20. In some instances, the antibody or immunoglobulin sequence comprises CDRH1 comprising at least a portion having at least or about 3, 4, 5, 6, 7, 8, 9, 10, 12, 14, 16, or more than 16 amino acids of SEQ ID NO: 3; a CDRH2 comprising at least a portion having at least or about 3, 4, 5, 6, 7, 8, 9, 10, 12, 14, 16, or more than 16 amino acids of SEQ ID NO: 6; a CDRH3 comprising at least a portion having at least or about 3, 4, 5, 6, 7, 8, 9, 10, 12, 14, 16, or more than 16 amino acids of SEQ ID NO: 9; a CDRL1 comprising at least a portion having at least or about 3, 4, 5, 6, 7, 8, 9, 10, 12, 14, 16, or more than 16 amino acids of SEQ ID NO: 14; a CDRL2 comprising at least a portion having at least or about 3, 4, 5, 6, 7, 8, 9, 10, 12, 14, 16, or more than 16 amino acids of SEQ ID NO: 17; and a CDRL3 comprising at least a portion having at least or about 3, 4, 5, 6, 7, 8, 9, 10, 12, 14, 16, or more than 16 amino acids of SEQ ID NO: 20.

In some instances, the CD3 antibody or immunoglobulin sequence comprises a heavy chain variable domain comprising at least or about 70%, 80%, 85%, 90%, 91%, 92%, 93%, 94%, 95%, 96%, 97%, 98%, 99%, or 100% sequence identity to any one of SEQ ID NOs: 21-32. In some instances, the CD3 antibody or immunoglobulin sequence comprises a heavy chain variable domain comprising at least or about 95% sequence identity to any one of SEQ ID NOs: 21-32. In some instances, the CD3 antibody or immunoglobulin sequence comprises a heavy chain variable domain comprising at least or about 97% sequence identity to any one of SEQ ID NOs: 21-32. In some instances, the CD3 antibody or immunoglobulin sequence comprises a heavy chain variable domain comprising at least or about 99% sequence identity to any one of SEQ ID NOs: 21-32. In some instances, the CD3 antibody or immunoglobulin sequence comprises a heavy chain variable domain comprising at least or about 100% sequence identity to any one of SEQ ID NOs: 21-32. In some instances, the CD3 antibody or immunoglobulin sequence comprises a heavy chain variable domain comprising at least a portion having at least or about 1, 2, 3, 4, 5, 6, 7, 8, 9, 10, 12, 14, 16, 18, 20, 30, 40, 50, 60, 70, 80, 90, 100, 110, 120, 130, 140, 150, or more than 150 amino acids of any one of SEQ ID NOs: 21-32.

In some instances, the CD3 antibody or immunoglobulin sequence comprises a heavy chain variable domain comprising at least or about 70%, 80%, 85%, 90%, 91%, 92%, 93%, 94%, 95%, 96%, 97%, 98%, 99%, or 100% sequence identity to any one of SEQ ID NOs: 25-32. In some instances, the CD3 antibody or immunoglobulin sequence comprises a heavy chain variable domain comprising at least or about 95% sequence identity to any one of SEQ ID NOs: 25-32. In some instances, the CD3 antibody or immunoglobulin sequence comprises a heavy chain variable domain comprising at least or about 97% sequence identity to any one of SEQ ID NOs: 25-32. In some instances, the CD3 antibody or immunoglobulin sequence comprises a heavy chain variable domain comprising at least or about 99% sequence identity to any one of SEQ ID NOs: 25-32. In some instances, the CD3 antibody or immunoglobulin sequence comprises a heavy chain variable domain comprising at least or about 100% sequence identity to any one of SEQ ID NOs: 25-32. In some instances, the CD3 antibody or immunoglobulin sequence comprises a heavy chain variable domain comprising at least a portion having at least or about 1, 2, 3, 4, 5, 6, 7, 8, 9, 10, 12, 14, 16, 18, 20, 30, 40, 50, 60, 70, 80, 90, 100, 110, 120, 130, 140, 150, or more than 150 amino acids of any one of SEQ ID NOs: 25-32.

In some instances, the CD3 antibody or immunoglobulin sequence comprises a light chain variable domain comprising at least or about 70%, 80%, 85%, 90%, 91%, 92%, 93%, 94%, 95%, 96%, 97%, 98%, 99%, or 100% sequence identity to any one of SEQ ID NOs: 33-36. In some instances, the CD3 antibody or immunoglobulin sequence comprises a light chain variable domain comprising at least or about 95% sequence identity to any one of SEQ ID NOs: 33-36. In some instances, the CD3 antibody or immunoglobulin sequence comprises a light chain variable domain comprising at least or about 97% sequence identity to any one of SEQ ID NOs: 33-36. In some instances, the CD3 antibody or immunoglobulin sequence comprises a light chain variable domain comprising at least or about 99% sequence identity to any one of SEQ ID NOs: 33-36. In some instances, the CD3 antibody or immunoglobulin sequence comprises a light chain variable domain comprising at least or about 100% sequence identity to any one of SEQ ID NOs: 33-36. In some instances, the CD3 antibody or immunoglobulin sequence comprises a light chain variable domain comprising at least a portion having at least or about 1, 2, 3, 4, 5, 6, 7, 8, 9, 10, 12, 14, 16, 18, 20, 30, 40, 50, 60, 70, 80, 90, 100, 110, 120, 130, 140, 150, or more than 150 amino acids of any one of SEQ ID NOs: 33-36.

Variant Libraries

Codon Variation

Variant nucleic acid libraries described herein may comprise a plurality of nucleic acids, wherein each nucleic acid encodes for a variant codon sequence compared to a reference nucleic acid sequence. In some instances, each nucleic acid of a first nucleic acid population contains a variant at a single variant site. In some instances, the first nucleic acid population contains a plurality of variants at a single variant site such that the first nucleic acid population contains more than one variant at the same variant site. The first nucleic acid population may comprise nucleic acids collectively encoding multiple codon variants at the same variant site. The first nucleic acid population may comprise nucleic acids collectively encoding up to 19 or more codons at the same position. The first nucleic acid population may comprise nucleic acids collectively encoding up to 60 variant triplets at the same position, or the first nucleic acid population may comprise nucleic acids collectively encoding up to 61 different triplets of codons at the same position. Each variant may encode for a codon that results in a different amino acid during translation. Table 1 provides a listing of each codon possible (and the representative amino acid) for a variant site.

TABLE 1

List of codons and amino adds

| Amino Acids | One Letter code | Three letter code | Codons | | | | | |
|---|---|---|---|---|---|---|---|---|
| Alanine | A | Ala | GCA | GCC | GCG | GCT | | |
| Cysteine | C | Cys | TGC | TGT | | | | |
| Aspartic acid | D | Asp | GAC | GAT | | | | |
| Glutamic acid | E | Glu | GAA | GAG | | | | |
| Phenylalanine | F | Phe | TTC | TIT | | | | |
| Glycine | G | Gly | GGA | GGC | GGG | GGT | | |
| Histidine | H | His | CAC | CAT | | | | |
| Isoleucine | I | Iso | ATA | ATC | ATT | | | |
| Lysine | K | Lys | AAA | AAG | | | | |
| Leucine | L | Leu | TTA | TTG | CTA | CTC | CTG | CTT |
| Methionine | M | Met | ATG | | | | | |
| Asparagine | N | Asn | AAC | AAT | | | | |
| Proline | P | Pro | CCA | CCC | CCG | CCT | | |
| Glutamine | Q | Gln | CAA | CAG | | | | |
| Arginine | R | Arg | AGA | AGG | CGA | CGC | CGG | CGT |
| Serine | S | Ser | AGC | AGT | TCA | TCC | TCG | TCT |
| Threonine | T | Thr | ACA | ACC | ACG | ACT | | |
| Valine | V | Val | GTA | GTC | GTG | GTT | | |
| Tryptophan | W | Trp | TGG | | | | | |
| Tyrosine | Y | Tyr | TAC | TAT | | | | |

A nucleic acid population may comprise varied nucleic acids collectively encoding up to 20 codon variations at multiple positions. In such cases, each nucleic acid in the population comprises variation for codons at more than one position in the same nucleic acid. In some instances, each nucleic acid in the population comprises variation for codons at 1, 2, 3, 4, 5, 6, 7, 8, 9, 10, 11, 12, 13, 14, 15, 16, 17, 18, 19, 20 or more codons in a single nucleic acid. In some instances, each variant long nucleic acid comprises variation for codons at 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 or more codons in a single long nucleic acid. In some instances, the variant nucleic acid population comprises variation for codons at 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 or more codons in a single nucleic acid. In some instances, the variant nucleic acid population comprises variation for codons in at least about 10, 20, 30, 40, 50, 60, 70, 80, 90, 100 or more codons in a single long nucleic acid.

Highly Parallel Nucleic Acid Synthesis

Provided herein is a platform approach utilizing miniaturization, parallelization, and vertical integration of the end-to-end process from polynucleotide synthesis to gene assembly within nanowells on silicon to create a revolutionary synthesis platform. Devices described herein provide, with the same footprint as a 96-well plate, a silicon synthesis platform is capable of increasing throughput by a factor of up to 1,000 or more compared to traditional synthesis methods, with production of up to approximately 1,000,000 or more polynucleotides, or 10,000 or more genes in a single highly-parallelized run.

With the advent of next-generation sequencing, high resolution genomic data has become an important factor for studies that delve into the biological roles of various genes in both normal biology and disease pathogenesis. At the core of this research is the central dogma of molecular biology and the concept of "residue-by-residue transfer of sequential information." Genomic information encoded in the DNA is transcribed into a message that is then translated into the protein that is the active product within a given biological pathway.

Another exciting area of study is on the discovery, development and manufacturing of therapeutic molecules focused on a highly-specific cellular target. High diversity DNA sequence libraries are at the core of development pipelines for targeted therapeutics. Gene mutants are used to express proteins in a design, build, and test protein engineering cycle that ideally culminates in an optimized gene for high expression of a protein with high affinity for its therapeutic target. As an example, consider the binding pocket of a receptor. The ability to test all sequence permutations of all residues within the binding pocket simultaneously will allow for a thorough exploration, increasing chances of success. Saturation mutagenesis, in which a researcher attempts to generate all possible mutations at a specific site within the receptor, represents one approach to this development challenge. Though costly and time and labor-intensive, it enables each variant to be introduced into each position. In contrast, combinatorial mutagenesis, where a few selected positions or short stretch of DNA may be modified extensively, generates an incomplete repertoire of variants with biased representation.

To accelerate the drug development pipeline, a library with the desired variants available at the intended frequency in the right position available for testing in other words, a precision library, enables reduced costs as well as turn-around time for screening. Provided herein are methods for synthesizing nucleic acid synthetic variant libraries which provide for precise introduction of each intended variant at the desired frequency. To the end user, this translates to the ability to not only thoroughly sample sequence space but also be able to query these hypotheses in an efficient manner, reducing cost and screening time. Genome-wide editing can elucidate important pathways, libraries where each variant and sequence permutation can be tested for optimal functionality, and thousands of genes can be used to reconstruct entire pathways and genomes to re-engineer biological systems for drug discovery.

In a first example, a drug itself can be optimized using methods described herein. For example, to improve a specified function of an antibody, a variant polynucleotide library encoding for a portion of the antibody is designed and synthesized. A variant nucleic acid library for the antibody can then be generated by processes described herein (e.g., PCR mutagenesis followed by insertion into a vector). The antibody is then expressed in a production cell line and screened for enhanced activity. Example screens include examining modulation in binding affinity to an antigen, stability, or effector function (e.g., ADCC, complement, or apoptosis). Exemplary regions to optimize the antibody include, without limitation, the Fc region. Fab region, variable region of the Fab region, constant region of the Fab region, variable domain of the heavy chain or light chain ($V_H$ or $V_L$), and specific complementarity-determining regions (CDRs) of $V_H$ or $V_L$.

Nucleic acid libraries synthesized by methods described herein may be expressed in various cells associated with a disease state. Cells associated with a disease state include cell lines, tissue samples, primary cells from a subject, cultured cells expanded from a subject, or cells in a model system. Exemplary model systems include, without limitation, plant and animal models of a disease state.

To identify a variant molecule associated with prevention, reduction or treatment of a disease state, a variant nucleic acid library described herein is expressed in a cell associated with a disease state, or one in which a cell a disease state can be induced. In some instances, an agent is used to induce a disease state in cells. Exemplary tools for disease state induction include, without limitation, a Cre/Lox recombination system, LPS inflammation induction, and streptozotocin to induce hypoglycemia. The cells associated with a disease state may be cells from a model system or cultured cells, as well as cells from a subject having a particular disease condition. Exemplary disease conditions include a bacterial, fungal, viral, autoimmune, or proliferative disorder (e.g., cancer). In some instances, the variant nucleic acid library is expressed in the model system, cell line, or primary cells derived from a subject, and screened for changes in at least one cellular activity. Exemplary cellular activities include, without limitation, proliferation, cycle progression, cell death, adhesion, migration, reproduction, cell signaling, energy production, oxygen utilization, metabolic activity, and aging, response to free radical damage, or any combination thereof.

Substrates

Devices used as a surface for polynucleotide synthesis may be in the form of substrates which include, without limitation, homogenous array surfaces, patterned array surfaces, channels, beads, gels, and the like. Provided herein are substrates comprising a plurality of clusters, wherein each cluster comprises a plurality of loci that support the attachment and synthesis of polynucleotides. In some instances, substrates comprise a homogenous array surface. For example, the homogenous array surface is a homogenous plate. The term "locus" as used herein refers to a discrete region on a structure which provides support for polynucleotides encoding for a single predetermined sequence to extend from the surface. In some instances, a locus is on a two dimensional surface, e.g., a substantially planar surface. In some instances, a locus is on a three-dimensional surface, e.g., a well, microwell, channel, or post. In some instances, a surface of a locus comprises a material that is actively functionalized to attach to at least one nucleotide for polynucleotide synthesis, or preferably, a population of identical nucleotides for synthesis of a population of polynucleotides. In some instances, polynucleotide refers to a population of polynucleotides encoding for the same nucleic acid sequence. In some cases, a surface of a substrate is inclusive of one or a plurality of surfaces of a substrate. The average error rates for polynucleotides synthesized within a library described here using the systems and methods provided are often less than 1 in 1000, less than about 1 in 2000, less than about 1 in 3000 or less often without error correction.

Provided herein are surfaces that support the parallel synthesis of a plurality of polynucleotides having different predetermined sequences at addressable locations on a common support. In some instances, a substrate provides support for the synthesis of more than 50, 100, 200, 400, 600, 800, 1000, 1200, 1400, 1600, 1800, 2,000; 5,000; 10,000; 20,000; 50,000; 100,000; 200,000; 300,000; 400,000; 500,000; 600,000; 700,000; 800,000; 900,000; 1,000,000; 1,200,000; 1,400,000; 1,600,000; 1,800,000; 2,000,000; 2,500,000; 3,000,000; 3,500,000; 4,000,000; 4,500,000; 5,000,000; 10,000,000 or more non-identical polynucleotides. In some cases, the surfaces provide support for the synthesis of more than 50, 100, 200, 400, 600, 800, 1000, 1200, 1400, 1600, 1800, 2,000; 5,000; 10,000; 20,000; 50,000; 100,000; 200,000; 300,000; 400,000; 500,000; 600,000; 700,000; 800,000; 900,000; 1,000,000; 1,200,000; 1,400,000; 1,600,000; 1,800,000; 2,000,000; 2,500,000; 3,000,000; 3,500,000; 4,000,000; 4,500,000; 5,000,000; 10,000,000 or more polynucleotides encoding for distinct sequences. In some instances, at least a portion of the polynucleotides have an identical sequence or are configured to be synthesized with an identical sequence. In some instances, the substrate provides a surface environment for the growth of polynucleotides having at least 80, 90, 100, 120, 150, 175, 200, 225, 250, 275, 300, 325, 350, 375, 400, 425, 450, 475, 500 bases or more.

Provided herein are methods for polynucleotide synthesis on distinct loci of a substrate, wherein each locus supports the synthesis of a population of polynucleotides. In some cases, each locus supports the synthesis of a population of polynucleotides having a different sequence than a population of polynucleotides grown on another locus. In some instances, each polynucleotide sequence is synthesized with 1, 2, 3, 4, 5, 6, 7, 8, 9 or more redundancy across different loci within the same cluster of loci on a surface for polynucleotide synthesis. In some instances, the loci of a substrate are located within a plurality of clusters. In some instances, a substrate comprises at least 10, 500, 1000, 2000, 3000, 4000, 5000, 6000, 7000, 8000, 9000, 10000, 11000, 12000, 13000, 14000, 15000, 20000, 30000, 40000, 50000 or more clusters. In some instances, a substrate comprises more than 2,000; 5,000; 10,000; 100,000; 200,000; 300,000; 400,000; 500,000; 600,000; 700,000; 800,000; 900,000; 1,000,000; 1,100,000; 1,200,000; 1,300,000; 1,400,000; 1,500,000; 1,600,000; 1,700,000; 1,800,000; 1,900,000; 2,000,000; 300,000; 400,000; 500,000; 600,000; 700,000; 800,000; 900,000; 1,000,000; 1,200,000; 1,400,000; 1,600, 000; 1,800,000; 2,000,000; 2,500,000; 3,000,000; 3,500, 000; 4,000,000; 4,500,000; 5,000,000; or 10,000,000 or more distinct loci. In some instances, a substrate comprises about 10,000 distinct loci. The amount of loci within a single cluster is varied in different instances. In some cases, each cluster includes 1, 2, 3, 4, 5, 6, 7, 8, 9, 10, 20, 30, 40, 50, 60, 70, 80, 90, 100, 120, 130, 150, 200, 300, 400, 500 or more loci. In some instances, each cluster includes about 50-500 loci. In some instances, each cluster includes about 100-200 loci. In some instances, each cluster includes about 100-150 loci. In some instances, each cluster includes about 109, 121, 130 or 137 loci. In some instances, each cluster includes about 19, 20, 61, 64 or more loci. Alternatively or in combination, polynucleotide synthesis occurs on a homogenous array surface.

In some instances, the number of distinct polynucleotides synthesized on a substrate is dependent on the number of distinct loci available in the substrate. In some instances, the density of loci within a cluster or surface of a substrate is at least or about 1, 10, 25, 50, 65, 75, 100, 130, 150, 175, 200, 300, 400, 500, 1,000 or more loci per $mm^2$. In some cases, a substrate comprises 10-500, 25-400, 50-500, 100-500, 150-500, 10-250, 50-250, 10-200, or 50-200 $mm^2$. In some instances, the distance between the centers of two adjacent loci within a cluster or surface is from about 10-500, from about 10-200, or from about 10-100 um. In some instances, the distance between two centers of adjacent loci is greater than about 10, 20, 30, 40, 50, 60, 70, 80, 90 or 100 um. In some instances, the distance between the centers of two adjacent loci is less than about 200, 150, 100, 80, 70, 60, 50, 40, 30, 20 or 10 um. In some instances, each locus has a width of about 0.5, 1, 2, 3, 4, 5, 6, 7, 8, 9, 10, 20, 30, 40, 50, 60, 70, 80, 90 or 100 um. In some cases, each locus has a width of about 0.5-100, 0.5-50, 10-75, or 0.5-50 um.

In some instances, the density of clusters within a substrate is at least or about 1 cluster per 100 $mm^2$, 1 cluster per 10 $mm^2$, 1 cluster per 5 $mm^2$, 1 cluster per 4 $mm^2$, 1 cluster per 3 $mm^2$, 1 cluster per 2 $mm^2$, 1 cluster per 1 $mm^2$, 2 clusters per 1 mm², 3 clusters per 1 mm², 4 clusters per mm², 5 clusters per 1 mm², 10 clusters per 1 mm², 50 clusters per 1 mm² or more. In some instances, a substrate comprises from about 1 cluster per 10 mm² to about 10 clusters per 1 mm². In some instances, the distance between the centers of two adjacent clusters is at least or about 50, 100, 200, 500, 1000, 2000, or 5000 um. In some cases, the distance between the centers of two adjacent clusters is between about 50-100, 50-200, 50-300, 50-500, and 100-2000 um. In some cases, the distance between the centers of two adjacent clusters is between about 0.05-50, 0.05-10, 0.05-5, 0.05-4, 0.05-3, 0.05-2, 0.1-10, 0.2-10, 0.3-10, 0,4-10, 0.5-10, 0.5-5, or 0.5-2 mm. In some cases, each cluster has a cross section of about 0.5 to about 2, about 0.5 to about 1, or about 1 to about 2 mm. In some cases, each cluster has a cross section of about 0.5, 0.6, 0.7, 0.8, 0.9, 1, 1.1, 1.2, 1.3, 1.4, 1.5, 1.6, 1.7, 1.8, 1.9 or 2 mm. In some cases, each cluster has an interior cross section of about 0.5, 0.6, 0.7, 0.8, 0.9, 1, 1.1, 1.15, 1.2, 1.3, 1.4, 1.5, 1.6, 1.7, 1.8, 1.9 or 2 mm.

In some instances, a substrate is about the size of a standard 96 well plate, for example between about 100 and about 200 mm by between about 50 and about 150 mm. In some instances, a substrate has a diameter less than or equal to about 1000, 500, 450, 400, 300, 250, 200, 150, 100 or 50 mm. In some instances, the diameter of a substrate is between about 25-1000, 25-800, 25-600, 25-500, 25-400, 25-300, or 25-200 mm. In some instances, a substrate has a planar surface area of at least about 100; 200; 500; 1,000; 2,000; 5,000; 10,000; 12,000; 15,000; 20,000; 30,000; 40,000; 50,000 mm² or more. In some instances, the thickness of a substrate is between about 50-2000, 50-1000, 100-1000, 200-1000, or 250-1000 mm.

Surface Materials

Substrates, devices, and reactors provided herein are fabricated from any variety of materials suitable for the methods, compositions, and systems described herein. In certain instances, substrate materials are fabricated to exhibit a low level of nucleotide binding. In some instances, substrate materials are modified to generate distinct surfaces that exhibit a high level of nucleotide binding. In some instances, substrate materials are transparent to visible and/or IV light. In some instances, substrate materials are sufficiently conductive, e.g., are able to form uniform electric fields across all or a portion of a substrate. In some instances, conductive materials are connected to an electric ground. In some instances, the substrate is heat conductive or insulated. In some instances, the materials are chemical resistant and heat resistant to support chemical or biochemical reactions, for example polynucleotide synthesis reaction processes. In some instances, a substrate comprises flexible materials. For flexible materials, materials can include, without limitation: nylon, both modified and unmodified, nitrocellulose, polypropylene, and the like. In some instances, a substrate comprises rigid materials. For rigid materials, materials can include, without limitation: glass; fuse silica; silicon, plastics (for example polytetraflouroethylene, polypropylene, polystyrene, polycarbonate, and blends thereof, and the like); metals (for example, gold, platinum, and the like). The substrate, solid support or reactors can be fabricated from a material selected from the group consisting of silicon, polystyrene, agarose, dextran, cellulosic polymers, polyacrylamides, polydimethylsiloxane (PDMS), and glass. The substrates/solid supports or the microstructures, reactors therein may be manufactured with a combination of materials listed herein or any other suitable material known in the art.

Surface Architecture

Provided herein are substrates for the methods, compositions, and systems described herein, wherein the substrates have a surface architecture suitable for the methods, compositions, and systems described herein. In some instances, a substrate comprises raised and/or lowered features. One benefit of having such features is an increase in surface area to support polynucleotide synthesis. In some instances, a substrate having raised and/or lowered features is referred to as a three-dimensional substrate. In some cases, a three-dimensional substrate comprises one or more channels. In some cases, one or more loci comprise a channel. In some cases, the channels are accessible to reagent deposition via a deposition device such as a material deposition device. In some cases, reagents and/or fluids collect in a larger well in fluid communication one or more channels. For example, a substrate comprises a plurality of channels corresponding to a plurality of loci with a cluster, and the plurality of channels are in fluid communication with one well of the cluster. In some methods, a library of polynucleotides is synthesized in a plurality of loci of a cluster.

Provided herein are substrates for the methods, compositions, and systems described herein, wherein the substrates are configured for polynucleotide synthesis. In some instances, the structure is configured to allow for controlled flow and mass transfer paths for polynucleotide synthesis on a surface, in some instances, the configuration of a substrate allows for the controlled and even distribution of mass transfer paths, chemical exposure times, anchor wash efficacy during polynucleotide synthesis. In some instances, the configuration of a substrate allows for increased sweep efficiency, for example by providing sufficient volume for a growing polynucleotide such that the excluded volume by the growing polynucleotide does not take up more than 50, 45, 40, 35, 30, 25, 20, 15, 14, 13, 12, 11, 10, 9, 8, 7, 6, 5, 4, 3, 2, 1%, or less of the initially available volume that is available or suitable for growing the polynucleotide. In some instances, a three-dimensional structure allows for managed flow of fluid to allow for the rapid exchange of chemical exposure.

Provided herein are substrates for the methods, compositions, and systems described herein, wherein the substrates comprise structures suitable for the methods, compositions, and systems described herein. In some instances, segregation is achieved by physical structure. In some instances, segregation is achieved by differential functionalization of the surface generating active and passive regions for polynucleotide synthesis. In some instances, differential functionalization is achieved by alternating the hydrophobicity across the substrate surface, thereby creating water contact angle effects that cause beading or wetting of the deposited reagents. Employing larger structures can decrease splashing and cross-contamination of distinct polynucleotide synthesis locations with reagents of the neighboring spots. In some cases, a device, such as a material deposition device, is used to deposit reagents to distinct polynucleotide synthesis locations. Substrates having three-dimensional features are configured in a manner that allows for the synthesis of a large number of polynucleotides (e.g., more than about 10,000) with a low error rate (e.g., less than about 1:500, 1:1000, 1:1500, 1:2,000, 1:3,000, 1:5,000, or 1:10,000). In some cases, a substrate comprises features with a density of about or greater than about 1, 5, 10, 20, 30, 40, 50, 60, 70, 80, 100, 110, 120, 130, 140, 150, 160, 170, 180, 190, 200, 300, 400 or 500 features per mm².

A well of a substrate may have the same or different width, height, and/or volume as another well of the substrate. A channel of a substrate may have the same or different width, height, and/or volume as another channel of the substrate. In some instances, the diameter of a cluster or the diameter of a well comprising a cluster, or both, is between about 0.05-50, 0.05-10, 0.05-5, 0.05-4, 0.05-3, 0.05-2, 0.05-1, 0.05-0.5, 0.05-0.1, 0.1-10, 0.2-10, 0.3-10, 0.4-10, 0.5-10, 0.5-5, or 0.5-2 mm. In some instances, the diameter of a cluster or well or both is less than or about 5, 4, 3, 2, 1, 0.5, 0.1, 0.09, 0.08, 0.07, 0.06, or 0.05 mm. In some instances, the diameter of a cluster or well or both is between about 1.0 and 1.3 mm. In some instances, the diameter of a cluster or well, or both is about 1.150 mm. In some instances, the diameter of a cluster or well, or both is about 0.08 mm. The diameter of a cluster refers to clusters within a two-dimensional or three-dimensional substrate.

In some instances, the height of a well is from about 20-1000, 50-1000, 100-1000, 200-1000, 300-1000, 400-1000, or 500-1000 um. In some cases, the height of a well is less than about 1000, 900, 800, 700, or 600 um.

In some instances, a substrate comprises a plurality of channels corresponding to a plurality of loci within a cluster, wherein the height or depth of a channel is 5-500, 5-400, 5-300, 5-200, 5-100, 5-50, or 10-50 um. In some cases, the height of a channel is less than 100, 80, 60, 40, or 20 um.

In some instances, the diameter of a channel, locus (e.g., in a substantially planar substrate) or both channel and locus (e.g., in a three-dimensional substrate wherein a locus corresponds to a channel) is from about 1-1000, 1-500, 1-200, 1-100, 5-100, or 10-100 um, for example, about 90, 80, 70, 60, 50, 40, 30, 20 or 10 um. In some instances, the diameter of a channel, locus, or both channel and locus is less than about 100, 90, 80, 70, 60, 50, 40, 30, 20 or 10 um. In some instances, the distance between the center of two adjacent channels, loci, or channels and loci is from about 1-500, 1-200, 1-100, 5-200, 5-100, 5-50, or 5-30, for example, about 20 um.

Surface Modifications

Provided herein are methods for polynucleotide synthesis on a surface, wherein the surface comprises various surface modifications. In some instances, the surface modifications are employed for the chemical and/or physical alteration of a surface by an additive or subtractive process to change one or more chemical and/or physical properties of a substrate surface or a selected site or region of a substrate surface. For example, surface modifications include, without limitation (1) changing the wetting properties of a surface, (2) functionalizing a surface, i.e., providing, modifying or substituting surface functional groups, (3) defunctionalizing a surface, i.e., removing surface functional groups, (4) otherwise altering the chemical composition of a surface, e.g., through etching, (5) increasing or decreasing surface roughness, (6) providing a coating on a surface, e.g., a coating that exhibits wetting properties that are different from the wetting properties of the surface, and/or (7) depositing particulates on a surface.

In some cases, the addition of a chemical layer on top of a surface (referred to as adhesion promoter) facilitates structured patterning of loci on a surface of a substrate. Exemplary surfaces for application of adhesion promotion include, without limitation, glass, silicon, silicon dioxide and silicon nitride. In some cases, the adhesion promoter is a chemical with a high surface energy. In some instances, a second chemical layer is deposited on a surface of a substrate. In some cases, the second chemical layer has a low surface energy. In some cases, surface energy of a chemical layer coated on a surface supports localization of droplets on the surface. Depending on the patterning arrangement selected, the proximity of loci and/or area of fluid contact at the loci are alterable.

In some instances, a substrate surface, or resolved loci, onto which nucleic acids or other moieties are deposited, e.g., for polynucleotide synthesis, are smooth or substantially planar (e.g., two-dimensional) or have irregularities, such as raised or lowered features (e.g., three-dimensional features). In some instances, a substrate surface is modified with one or more different layers of compounds. Such modification layers of interest include, without limitation, inorganic and organic layers such as metals, metal oxides, polymers, small organic molecules and the like.

In some instances, resolved loci of a substrate are functionalized with one or more moieties that increase and/or decrease surface energy. In some cases, a moiety is chemically inert. In some cases, a moiety is configured to support a desired chemical reaction, for example, one or more processes in a polynucleotide synthesis reaction. The surface energy, or hydrophobicity, of a surface is a factor for determining the affinity of a nucleotide to attach onto the surface. In some instances, a method for substrate functionalization comprises: (a) providing a substrate having a surface that comprises silicon dioxide; and (b) silanizing the surface using, a suitable silanizing agent described herein or otherwise known in the art, for example, an organofunctional alkoxysilane molecule. Methods and functionalizing agents are described in U.S. Pat. No. 5,474,796, which is herein incorporated by reference in its entirety.

In some instances, a substrate surface is functionalized by contact with a derivatizing composition that contains a mixture of silanes, under reaction conditions effective to couple the silanes to the substrate surface, typically via reactive hydrophilic moieties present on the substrate surface. Silanization generally covers a surface through self-assembly with organofunctional alkoxysilane molecules. A variety of siloxane functionalizing reagents can further be used as currently known in the art, e.g., for lowering or increasing surface energy. The organofunctional alkoxysilanes are classified according to their organic functions.

Polynucleotide Synthesis

Methods of the current disclosure for polynucleotide synthesis may include processes involving phosphoramidite chemistry. In some instances, polynucleotide synthesis comprises coupling a base with phosphoramidite. Polynucleotide synthesis may comprise coupling a base by deposition of phosphoramidite under coupling conditions, wherein the same base is optionally deposited with phosphoramidite more than once, i.e., double coupling. Polynucleotide synthesis may comprise capping of unreacted sites. In some instances, capping is optional. Polynucleotide synthesis may also comprise oxidation or an oxidation step or oxidation steps. Polynucleotide synthesis may comprise deblocking, detritylation, and sulfurization. In some instances, polynucleotide synthesis comprises either oxidation or sulfurization. In some instances, between one or each step during a polynucleotide synthesis reaction, the device is washed, for example, using tetrazole or acetonitrile. Time frames for any one step in a phosphoramidite synthesis method may be less than about 2 min, 1 min, 50 sec, 40 sec, 30 sec, 20 sec and 10 sec.

Polynucleotide synthesis using a phosphoramidite method may comprise a subsequent addition of a phosphoramidite building block (e.g., nucleoside phosphoramidite) to a growing polynucleotide chain for the formation of a phosphite triester linkage. Phosphoramidite polynucleotide synthesis proceeds in the 3' to 5' direction. Phosphoramidite polynucleotide synthesis allows for the controlled addition of one nucleotide to a growing nucleic acid chain per synthesis cycle. In some instances, each synthesis cycle comprises a coupling step. Phosphoramidite coupling involves the formation of a phosphite triester linkage between an activated nucleoside phosphoramidite and a nucleoside bound to the substrate, for example, via a linker. In some instances, the nucleoside phosphoramidite is provided to the device activated. In some instances, the nucleoside phosphoramidite is provided to the device with an activator. In some instances, nucleoside phosphoramidites are provided to the device in a 1.5, 2, 3, 4, 5, 6, 7, 8, 9, 10, 11, 12, 13, 14, 15, 16, 17, 18, 19, 20, 25, 30, 35, 40, 50, 60, 70, 80, 90, 100-fold excess or more over the substrate-bound nucleosides. In some instances, the addition of nucleoside phosphoramidite is performed in an anhydrous environment, for example, in anhydrous acetonitrile. Following addition of a nucleoside phosphoramidite, the device is optionally washed. In some instances, the coupling step is repealed one or more additional times, optionally with a wash step between nucleoside phosphoramidite additions to the substrate. In some instances, a polynucleotide synthesis method used herein comprises 1, 2, 3 or more sequential coupling steps. Prior to coupling, in many cases, the nucleoside bound to the device is de-protected by removal of a protecting group, where the protecting group functions to prevent polymerization. A common protecting group is 4,4'-dimethoxytrityl (DMT).

Following coupling, phosphoramidite polynucleotide synthesis methods optionally comprise a capping step. In a capping step, the growing polynucleotide is treated with a capping agent. A capping step is useful to block unreacted substrate-bound 5'-OH groups after coupling from further chain elongation, preventing the formation of polynucleotides with internal base deletions. Further, phosphoramidites activated with 1H-tetrazole may react, to a small extent, with the O6 position of guanosine. Without being bound by theory, upon oxidation with $I_2$/water, this side product, possibly via O6-N7 migration, may undergo depurination. The apurinic sites may end up being cleaved in the course of the final deprotection of the polynucleotide thus reducing the yield of the full-length product. The O6 modifications may be removed by treatment with the capping reagent prior to oxidation with $I_2$/water. In some instances, inclusion of a capping step during polynucleotide synthesis decreases the error rate as compared to synthesis without capping. As an example, the capping step comprises treating the substrate-bound polynucleotide with a mixture of acetic anhydride and 1-methylimidazole. Following a capping step, the device is optionally washed.

In some instances, following addition of a nucleoside phosphoramidite, and optionally after capping and one or more wash steps, the device bound growing nucleic acid is oxidized. The oxidation step comprises the phosphite triester is oxidized into a tetracoordinated phosphate triester, a protected precursor of the naturally occurring phosphate diester internucleoside linkage. In some instances, oxidation of the growing polynudeotide is achieved by treatment with iodine and water, optionally in the presence of a weak base (e.g., pyridine, lutidine, collidine). Oxidation may be carried out under anhydrous conditions using, e.g. tert-Butyl hydroperoxide or (1S)-(+)-(10-camphorsulfonyl)-oxaziridine (CSO). In some methods, a capping step is performed following oxidation. A second capping step allows for device drying, as residual water from oxidation that may persist can inhibit subsequent coupling. Following oxidation, the device and growing polynucleotide is optionally washed. In some instances, the step of oxidation is substituted with a sulfurization step to obtain polynucleotide phosphorothioates, wherein any capping steps can be performed after the sulfurization. Many reagents are capable of the efficient sulfur transfer, including but not limited to 3-(Dimethylaminomethylidene)amino)-3H-1,2,4-dithiazole-3-thione, DDTT, 3H-1,2-benzodithiol-3-one 1,1-dioxide, also known as Beaucage reagent, and N,N,N'N'-Tetraethylthiuram disulfide (TETD).

In order for a subsequent cycle of nucleoside incorporation to occur through coupling, the protected 5' end of the device bound growing polynucleotide is removed so that the primary hydroxyl group is reactive with a next nucleoside phosphoramidite. In some instances, the protecting group is DMT and deblocking occurs with trichloroacetic acid in dichloromethane. Conducting detritylation for an extended time or with stronger than recommended solutions of acids may lead to increased depurination of solid support-bound polynucleotide and thus reduces the yield of the desired full-length product. Methods and compositions of the disclosure described herein provide for controlled deblocking conditions limiting undesired depurination reactions. In some instances, the device hound polynucleotide is washed after deblocking. In some instances, efficient washing after deblocking contributes to synthesized polynucleotides having a low error rate.

Methods for the synthesis of polynucleotides typically involve an iterating sequence of the following steps: application of a protected monomer to an actively functionalized surface (e.g., locus) to link with either the activated surface, a linker or with a previously deprotected monomer; deprotection of the applied monomer so that it is reactive with a subsequently applied protected monomer; and application of another protected monomer for linking. One or more intermediate steps include oxidation or sulfurization. In some instances, one or more wash steps precede or follow one or all of the steps.

Methods for phosphoramidite-based polynucleotide synthesis comprise a series of chemical steps. In some instances, one or more steps of a synthesis method involve reagent cycling, where one or more steps of the method comprise application to the device of a reagent useful for the step. For example, reagents are cycled by a series of liquid deposition and vacuum drying steps. For substrates comprising three-dimensional features such as wells, microwells, channels and the like, reagents are optionally passed through one or more regions of the device via the wells and/or channels.

Methods and systems described herein relate to polynucleotide synthesis devices for the synthesis of polynucleotides. The synthesis may be in parallel. For example, at least or about at least 2, 3, 4, 5, 6, 7, 8, 9, 10, 11, 12, 13, 14, 15, 16, 17, 18, 19, 20, 21, 22, 23, 24, 25, 30, 35, 40, 45, 50, 100, 150, 200, 250, 300, 350, 400, 450, 500, 550, 600, 650, 700, 750, 800, 850, 900, 1000, 10000, 50000, 75000, 100000 or more polynucleotides can be synthesized in parallel. The total number polynucleotides that may be synthesized in parallel may be from 2-100000, 3-50000, 4-10000, 5-1000, 6-900, 7-850, 8-800, 9-750, 10-700, 11-650, 12-600, 13-550, 14-500, 15-450, 16-400, 17-350, 18-300, 19-250, 20-200, 21-150,22-100, 23-50, 24-45, 25-40, 30-35. Those of skill in the art appreciate that the total number of polynucleotides synthesized in parallel may fall within any range bound by any of these values, for example 25-100. The total number of polynucleotides synthesized in parallel may fall within any range defined by any of the values serving as endpoints of the range. Total molar mass of polynucleotides synthesized within the device or the molar mass of each of the polynucleotides may be at least or at least about 10, 20, 30, 40, 50, 100, 250, 500, 750, 1000, 2000, 3000, 4000, 5000, 6000, 7000, 8000, 9000, 10000, 25000, 50000, 75000, 100000 picomoles, or more. The length of each of the polynucleotides or average length of the polynucleotides within the device may be at least or about at least 10, 15, 20, 25, 30, 35, 40, 45, 50, 100, 150, 200, 300, 400, 500 nucleotides, or more. The length of each of the polynucleotides or average length of the polynucleotides within the device may be almost or about at most 500, 400, 300, 200, 150, 100, 50, 45, 35, 30, 25, 20, 19, 18, 17, 16, 15, 14, 13, 12, 11, 10 nucleotides, or less. The length of each of the polynucleotides or average length of the polynucleotides within the device may fall from 10-500, 9-400, 11-300, 12-200, 13-150, 14-100, 15-50, 16-45, 17-40, 18-35, 19-25. Those of skill in the art appreciate that the length of each of the polynucleotides or average length of the polynucleotides within the device may fall within any range bound by any of these values, for example 100-300. The length of each of the polynucleotides or average length of the polynucleotides within the device may fall within any range defined by any of the values serving as endpoints of the range.

Methods for polynucleotide synthesis on a surface provided herein allow for synthesis at a fast rate. As an example, at least 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, 55, 60, 70, 80, 90, 100, 125, 150, 175, 200 nucleotides per hour, or more are synthesized. Nucleotides include adenine, guanine, thymine, cytosine, uridine building blocks, or analogs/modified versions thereof. In some instances, libraries of polynucleotides are synthesized in parallel on substrate. For example, a device comprising about or at least about 100; 1,000; 10,000; 30,000; 75,000; 100,000; 1,000,000; 2,000,000; 3,000,000; 4,000,000; or 5,000,000 resolved loci is able to support the synthesis of at least the same number of distinct polynucleotides, wherein polynucleotide encoding a distinct sequence is synthesized on a resolved locus. In some instances, a library of polynucleotides is synthesized on a device with low error rates described herein in less than about three months, two months, one month, three weeks, 15, 14, 13, 12, 11, 10, 9, 8, 7, 6, 5, 4, 3, 2 days, 24 hours or less. In some instances, larger nucleic acids assembled from a polynucleotide library synthesized with low error rate using the substrates and methods described herein are prepared in less than about three months, two months, one month, three weeks, 15, 14, 13, 12, 11, 10, 9, 8, 7, 6, 5, 4, 3, 2 days, 24 hours or less.

In some instances, methods described herein provide for generation of a library of nucleic acids comprising variant nucleic acids differing at a plurality of codon sites. In some instances, a nucleic acid may have 1 site, 2 sites, 3 sites, 4 sites, 5 sites, 6 sites, 7 sites, 8 sites, 9 sites, 10 sites, 11 sites, 12 sites, 13 sites, 14 sites, 15 sites, 16 sites, 17 sites 18 sites, 19 sites, 20 sites, 30 sites, 40 sites, 50 sites, or more of variant codon sites.

In some instances, the one or more sites of variant codon sites may be adjacent. In some instances, the one or more sites of variant codon sites may not be adjacent and separated by 1, 2, 3, 4, 5, 6, 7, 8, 9, 10, or more codons.

In some instances, a nucleic acid may comprise multiple sites of variant codon sites, wherein all the variant codon sites are adjacent to one another, forming a stretch of variant codon sites. In some instances, a nucleic acid may comprise multiple sites of variant codon sites, wherein none the variant codon sites are adjacent to one another. In some instances, a nucleic acid may comprise multiple sites of variant codon sites, wherein some the variant codon sites are adjacent to one another, forming a stretch of variant codon sites, and some of the variant codon sites are not adjacent to one another.

Referring to the Figures, FIG. 1 illustrates an exemplary process workflow for synthesis of nucleic acids (e.g., genes) from shorter nucleic acids. The workflow is divided generally into phases: (1) de novo synthesis of a single stranded nucleic acid library, (2) joining nucleic acids to form larger fragments, (3) error correction, (4) quality control, and (5) shipment. Prior to de novo synthesis, an intended nucleic acid sequence or group of nucleic acid sequences is preselected. For example, a group of genes is preselected for generation.

Once large nucleic acids for generation are selected, a predetermined library of nucleic acids is designed for de novo synthesis. Various suitable methods are known for generating high density polynucleotide arrays. In the workflow example, a device surface layer is provided. In the example, chemistry of the surface is altered in order to improve the polynucleotide synthesis process. Areas of low surface energy are generated to repel liquid while areas of high surface energy are generated to attract liquids. The surface itself may be in the form of a planar surface or contain variations in shape, such as protrusions or microwells which increase surface area. In the workflow example, high surface energy molecules selected serve a dual function of supporting DNA chemistry, as disclosed in International Patent Application Publication WO/2015/021080, which is herein incorporated by reference in its entirety.

In situ preparation of polynucleotide arrays is generated on a solid support and utilizes single nucleotide extension process to extend multiple oligomers in parallel. A deposition device, such as a material deposition device, is designed to release reagents in a step wise fashion such that multiple polynucleotides extend, in parallel, one residue at a time to generate oligomers with a predetermined nucleic acid sequence 102. In some instances, polynucleotides are cleaved from the surface at this stage. Cleavage includes gas cleavage, e.g., with ammonia or methylamine.

The generated polynucleotide libraries are placed in a reaction chamber. In this exemplary workflow, the reaction chamber (also referred to as "nanoreactor") is a silicon coated well, containing PCR reagents and lowered onto the polynucleotide library 103. Prior to or after the sealing 104 of the polynucleondes, a reagent is added to release the polynucleotides from the substrate. In the exemplary workflow, the polynucleotides are released subsequent to sealing of the nanoreactor 105. Once released, fragments of single stranded polynucleotides hybridize in order to span an entire long range sequence of DNA. Partial hybridization 105 is possible because each synthesized polynucleotide is designed to have a small portion overlapping with at least one other polynucleotide in the pool.

After hybridization, a PCA reaction is commenced. During the polymerase cycles, the polynucleotides anneal to complementary fragments and gaps are filled in by a polymerase. Each cycle increases the length of various fragments randomly depending on which polynucleotides find each other. Complementarily amongst the fragments allows for forming a complete large span of double stranded DNA 106.

After PCA is complete, the nanoreactor is separated from the device 107 and positioned for interaction with a device having primers for PCR 108. After sealing, the nanoreactor is subject to PCR 109 and the larger nucleic acids are amplified. After PCR 110, the nanochamber is opened 111, error correction reagents are added 112, the chamber is sealed 113 and an error correction reaction occurs to remove mismatched base pairs and/or strands with poor complementarity from the double stranded PCR amplification products 114. The nanoreactor is opened and separated 115. Error corrected product is next subject to additional processing steps, such as PCR and molecular bar coding, and then packaged 122 for shipment 123.

In some instances, quality control measures are taken. After error correction, quality control steps include for example interaction with a wafer having sequencing primers for amplification of the error corrected product 116, sealing the wafer to a chamber containing error corrected amplification product 117, and performing an additional round of amplification 118. The nanoreactor is opened 119 and the products are pooled 120 and sequenced 121. After an acceptable quality control determination is made, the packaged product 122 is approved for shipment 123.

In some instances, a nucleic acid generated by a workflow such as that in FIG. 1 is subject to mutagenesis using overlapping primers disclosed herein. In some instances, a library of primers are generated by in situ preparation on a solid support and utilize single nucleotide extension process to extend multiple oligomers in parallel. A deposition device, such as a material deposition device, is designed to release reagents in a step wise fashion such that multiple polynucleotides extend, in parallel, one residue at a time to generate oligomers with a predetermined nucleic acid sequence 102.

Computer Systems

Any of the systems described herein, may be operably linked to a computer and may be automated through a computer either locally or remotely. In various instances, the methods and systems of the disclosure may further comprise software programs on computer systems and use thereof. Accordingly, computerized control for the synchronization of the dispense/vacuum/refill functions such as orchestrating and synchronizing the material deposition device movement, dispense action and vacuum actuation are within the bounds of the disclosure. The computer systems may be programmed to interface between the user specified base sequence and the position of a material deposition device to deliver the correct reagents to specified regions of the substrate.

Figure 2:
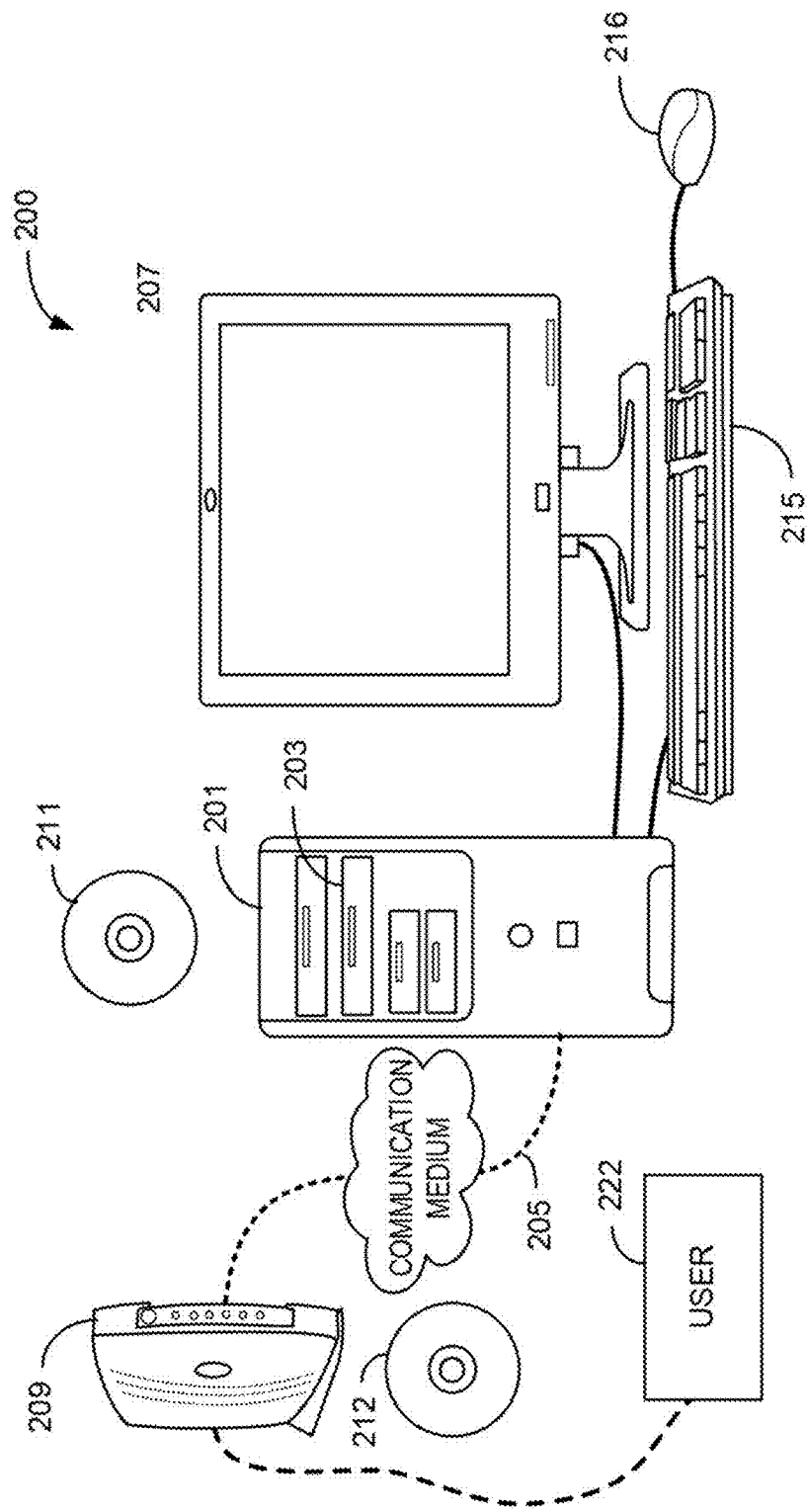
FIG. 2 illustrates an example of a computer system.

The computer system 200 illustrated in FIG. 2 may be understood as a logical apparatus that can read instructions from media 211 and/or a network port 205, which can optionally be connected to server 209 having fixed media 212. The system, such as shown in FIG. 2 can include a CPU 201, disk drives 203, optional input devices such as keyboard 215 and/or mouse 216 and optional monitor 207. Data communication can be achieved through the indicated communication medium to a server at a local or a remote location. The communication medium can include any means of transmitting and/or receiving data. For example, the communication medium can be a network connection, a wireless connection or an internet connection. Such a connection can provide for communication over the World Wide Web. It is envisioned that data relating to the present disclosure can be transmitted over such networks or connections for reception and/or review by a party 222 as illustrated in FIG. 2.

Figure 3:
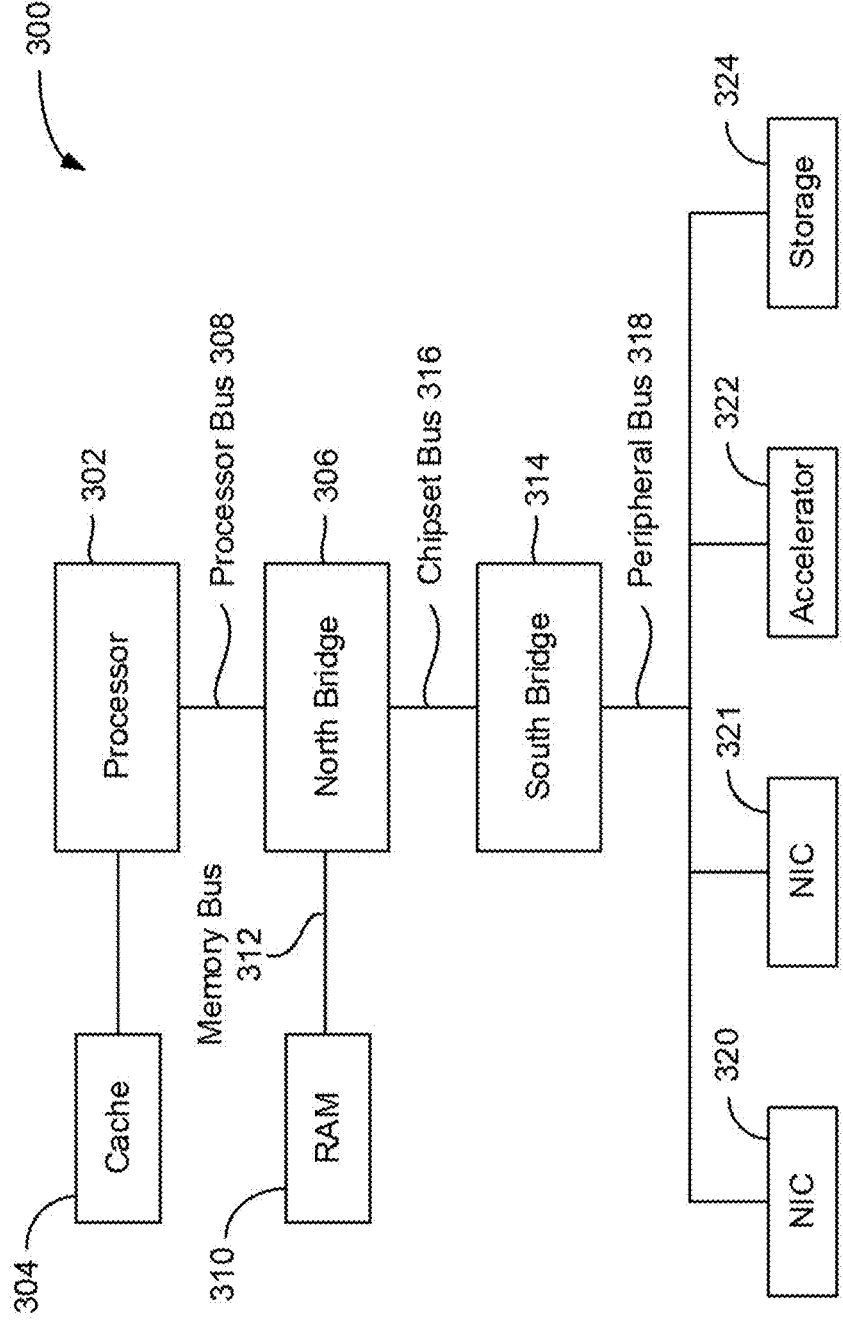
FIG. 3 is a block diagram illustrating an architecture of a computer system.

As illustrated in FIG. 3, a high speed cache 304 can be connected to, or incorporated in, the processor 302 to provide a high speed memory for instructions or data that have been recently, or are frequently, used by processor 302. The processor 302 is connected to a north bridge 306 by a processor bus 308. The north bridge 306 is connected to random access memory (RAM) 310 by a memory bus 312 and manages access to the RAM 310 by the processor 302. The north bridge 306 is also connected to a south bridge 314 by a chipset bus 316. The south bridge 314 is, in turn, connected to a peripheral bus 318. The peripheral bus can be, for example, PCI, PCI-X, PCI Express, or other peripheral bus. The north bridge and south bridge are often referred to as a processor chipset and manage data transfer between the processor, RAM, and peripheral components on the peripheral bus 318. In some alternative architectures, the functionality of the north bridge can be incorporated into the processor instead of using a separate north bridge chip. In some instances, system 300 can include an accelerator card 322 attached to the peripheral bus 318. The accelerator can include field programmable gate arrays (FPGAs) or other hardware for accelerating certain processing. For example, an accelerator can be used for adaptive data restructuring or to evaluate algebraic expressions used in extended set processing.

Software and data are stored in external storage 324 and can be loaded into RAM 310 and/or cache 304 for use by the processor. The system 300 includes an operating system for managing system resources; non-limiting examples of operating systems include: Linux™, Windows™, MACOS™, BlackBerry OS™, iOS™, and other functionally-equivalent operating systems, as well as application software running on top of the operating system for managing data storage and optimization in accordance with example instances of the present disclosure. In this example, system 300 also includes network interface cards (NICs) 320 and 3 connected to the peripheral bus for providing network interfaces to external storage, such as Network Attached Storage (NAS) and other computer systems that can be used for distributed parallel processing.

Figure 4:
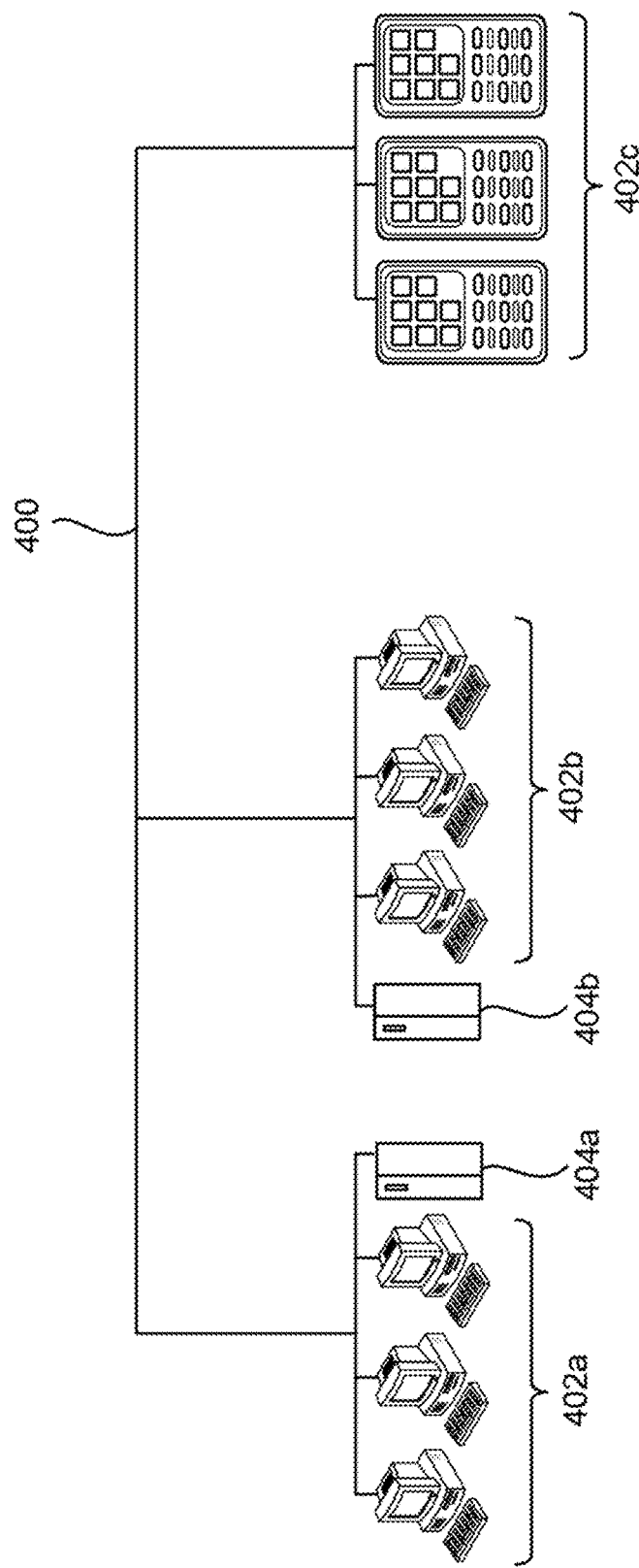
FIG. 4 is a diagram demonstrating a network configured to incorporate a plurality of computer systems, a plurality of cell phones and personal data assistants, and Network Attached Storage (NAS).

FIG. 4 is a diagram showing a network 400 with a plurality of computer systems 402a, and 402b, a plurality of cell phones and personal data assistants 402c, and Network Attached Storage (NAS) 404a, and 404b. In example instances, systems 402a, 402b, and 402c can manage data storage and optimize data access for data stored in Network Attached Storage (NAS) 404a and 404b. A mathematical model can be used for the data and be evaluated using distributed parallel processing across computer systems 402a, and 402b, and cell phone and personal data assistant systems 402c. Computer systems 402a, and 402b, and cell phone and personal data assistant systems 402c can also provide parallel processing for adaptive data restructuring of the data stored in Network Attached Storage (NAS) 404a and 404b. FIG. 4 illustrates an example only, and a wide variety of other computer architectures and systems can be used in conjunction with the various instances of the present disclosure. For example, a blade server can be used to provide parallel processing. Processor blades can be connected through a back plane to provide parallel processing. Storage can also be connected to the back plane or as Network Attached Storage (NAS) through a separate network interface. In some example instances, processors can maintain separate memory spaces and transmit data through network interfaces, back plane or other connectors for parallel processing by other processors. In other instances, some or all of the processors can use a shared virtual address memory space.

Figure 5:
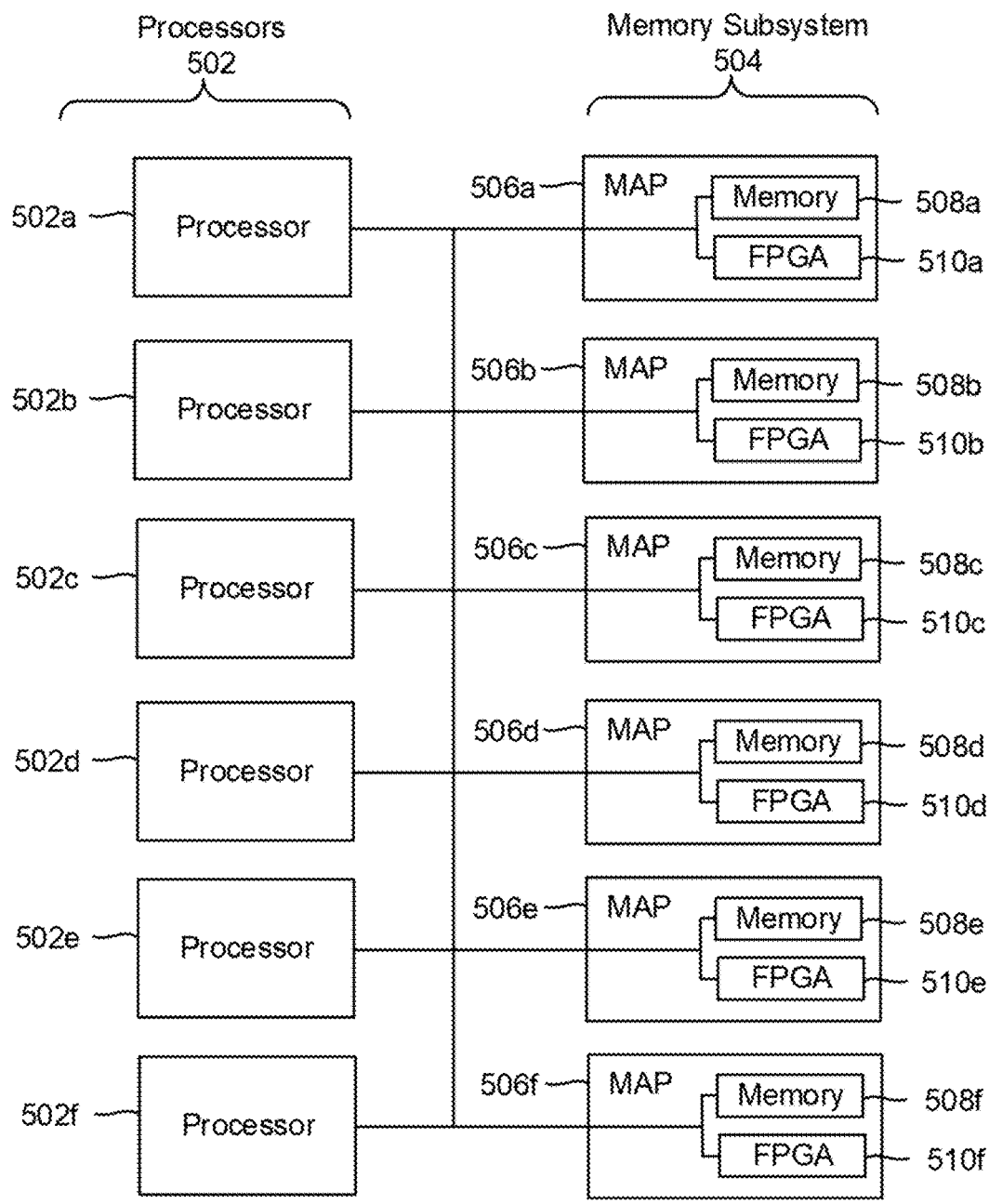
FIG. 5 is a block diagram of a multiprocessor computer system using a shared virtual address memory space.

FIG. 5 is a block diagram of a multiprocessor computer system 500 using a shared virtual address memory space in accordance with an example instance. The system includes a plurality of processors 502a-f that can access a shared memory subsystem 504. The system incorporates a plurality of programmable hardware memory algorithm processors (MAPs) 506a-f in the memory subsystem 504. Each MAP 506a-f can comprise a memory 508a-f and one or more field programmable gate arrays (FPGAs) 510a-f. The MAP provides a configurable functional unit and particular algorithms or portions of algorithms can be provided to the FPGAs 510a-f for processing in close coordination with a respective processor. For example, the MAPs can be used to evaluate algebraic expressions regarding the data model and to perform adaptive data restructuring in example instances. In this example, each MAP is globally accessible by all of the processors for these purposes. In one configuration, each MAP can use Direct Memory Access (DMA) to access an associated memory 508a-f, allowing it to execute tasks independently of, and asynchronously from the respective microprocessor 502a-f. In this configuration, a MAP can feed results directly to another MAP for pipelining and parallel execution of algorithms.

The above computer architectures and systems are examples only, and a wide variety of other computer, cell phone, and personal data assistant architectures and systems can be used in connection with example instances, including systems using any combination of general processors, co-processors, FPGAs and other programmable logic devices, system on chips (SOCs), application specific integrated circuits (ASICs), and other processing and logic elements. In some instances, all or part of the computer system can be implemented in software or hardware. Any variety of data storage media can be used in connection with example instances, including random access memory, hard drives, flash memory, tape drives, disk arrays, Network Attached Storage (NAS) and other local or distributed data storage devices and systems.

In example instances, the computer system can be implemented using software modules executing on any of the above or other computer architectures and systems. In other instances, the functions of the system can be implemented partially or completely in firmware, programmable logic devices such as field programmable gate arrays (FPGAs) as referenced in FIG. 3, system on chips (SOCs), application specific integrated circuits (ASICs), or other processing and logic elements. For example, the Set Processor and Optimizer can be implemented with hardware acceleration through the use of a hardware accelerator card, such as accelerator card 322 illustrated in FIG. 3.

The following examples are set forth to illustrate more clearly the principle and practice of embodiments disclosed herein to those skilled in the art and are not to be construed as limiting the scope of any claimed embodiments. Unless otherwise stated, all parts and percentages are on a weight basis.

EXAMPLES

The following examples are given for the purpose of illustrating various embodiments of the disclosure and are not meant to limit the present disclosure in any fashion. The present examples, along with the methods described herein are presently representative of preferred embodiments, are exemplary, and are not intended as limitations on the scope of the disclosure. Changes therein and other uses which are encompassed within the spirit of the disclosure as defined by the scope of the claims will occur to those skilled in the art.

Example 1: Functionalization of a Device Surface

A device was functionalized to support the attachment and synthesis of a library of polynucleotides. The device surface was first wet cleaned using a piranha solution comprising 90% $H_2SO_4$ and 10% $H_2O_2$ for 20 minutes. The device was rinsed in several beakers with DI water, held under a DI water gooseneck faucet for 5 min, and dried with $N_2$. The device was subsequently soaked in $NH_4OH$ (1:100; 3 mL:300 mL) for 5 min, rinsed with DI water using a handgun, soaked in three successive beakers with DI water for 1 min each, and then rinsed again with DI water using the handgun. The device was then plasma cleaned by exposing the device surface to $O_2$. A SAMCO PC-300 instrument was used to plasma etch $O_2$ at 250 watts for 1 min in downstream mode.

The cleaned device surface was actively functionalized with a solution comprising N-(3-triethoxysilylpropyl-4-hydroxybutyramide using a YES-1224P vapor deposition oven system with the following parameters: 0.5 to 1 torr, 60 min, 70° C., 135° C. vaporizer. The device surface was resist coated using a Brewer Sciencer™ 200X spin coater. SPR™ 3612 photoresist was spin coated on the device at 2500 rpm for 40 sec. The device was pre-baked for 30 min at 90° C. on a Brewer hot plate. The device was subjected to photolithography using a Karl Suss MA6 mask aligner instrument. The device was exposed for 2.2 sec and developed for 1 min. in MSF 26A. Remaining developer was rinsed with the handgun and the device soaked in water for 5 min. The device was baked for 30 min at 100° C. in the oven, followed by visual inspection for lithography defects using a Nikon L200. A descum process was used to remove residual resist using the SAMCO PC-300 instrument to $O_2$ plasma etch at 250 watts for 1 mm.

The device surface was passively functionalized with a 100 μL solution of perfluorooctyltrichlorosilane mixed with 10 μL light mineral oil. The device was placed in a chamber, pumped for 10 min, and then the valve was closed to the pump and left to stand for 10 min. The chamber was vented to air. The device was resist stripped by performing two soaks for 5 min in 500 mL NMP at 70° C. with ultrasonication at maximum power (9 on Crest system). The device was then soaked for 5 min in 500 mL isopropanol at room temperature with ultrasonication at maximum power. The device was dipped in 300 mL of 200 proof ethanol and blown dry with $N_2$. The functionalized surface was activated to serve as a support for polynucleotide synthesis.

Example 2: Synthesis of a 50-mer Sequence on an Oligonucleotide Synthesis Device A two dimensional oligonucleotide synthesis device was assembled into a flowcell, which was connected to a flowcell (Applied Biosystems (ABI394 DNA Synthesizer"). The two-dimensional oligonucleotide synthesis device was uniformly functionalized with N-(3-TRIEFHOXYSILYLPROPYL)-4-HYDROXYBUTYRAMIDE (Gelest) was used to synthesize an exemplary polynucleotide of 50 bp ("50-mer polynucleotide") using polynucleotide synthesis methods described herein.

The sequence of the 50-mer was as described below: 5'AGACAATCAACCATYIGGGGTGGACAGCCTTGAC CICTAGACTTCGGCAT##TTTTTIT TTT3' (SEQ ID NO: 46), where #denotes Thymidine-succinyl hexamide CED phosphoramidite (CLP-2244 from ChemGenes), which is a cleavable linker enabling the release of oligos from the surface during deprotection.

The synthesis was done using standard DNA synthesis chemistry (coupling, capping, oxidation, and deblocking) according to the protocol in Table 2 and an ABI synthesizer.

TABLE 2

Synthesis protocols

| General DNA Synthesis | Table 2 | |
|---|---|---|
| Process Name | Process Step | Time (sec) |
| WASH (Acetonitrile Wash Flow) | Acetonitrile System Flush | 4 |
| | Acetonitrile to Flowcell | 23 |
| | N2 System Flush | 4 |
| | Acetonitrile System Flush | 4 |
| DNA BASE ADDITION (Phosphoramidite + Activator Flow) | Activator Manifold Flush | 2 |
| | Activator to Flowcell | 6 |
| | Activator + Phosphoramidite to Flowcell | 6 |
| | Activator to Flowcell | 0.5 |
| | Activator + Phosphoramidite to Flowcell | 5 |
| | Activator to Flowcell | 0.5 |
| | Activator + Phosphoramidite to Flowcell | 5 |
| | Activator to Flowcell | 0.5 |
| | Activator + Phosphoramidite to Flowcell | 5 |
| | Incubate for 25 sec | 25 |
| WASH (Acetonitrile Wash Flow) | Acetonitrile System Flush | 4 |
| | Acetonitrile to Flowcell | 15 |
| | N2 System Flush | 4 |
| | Acetonitrile System Flush | 4 |
| DNA BASE ADDITION (Phosphoramidite + Activator Flow) | Activator Manifold Flush | 2 |
| | Activator to Flowcell | 5 |
| | Activator + Phosphoramidite to Flowcell | 18 |
| | Incubate for 25 sec | 25 |
| WASH (Acetonitrile Wash Flow) | Acetonitrile System Flush | 4 |
| | Acetonitrile to Flowcell | 15 |
| | N2 System Flush | 4 |
| | Acetonitrile System Flush | 4 |
| CAPPING (CapA + B, 1:1, Flow) | CapA + B to Flowcell | 15 |
| WASH (Acetonitrile Wash Flow) | Acetonitrile System Flush | 4 |
| | Acetonitrile to Flowcell | 15 |
| | Acetonitrile System Flush | 4 |
| OXIDATION (Oxidizer Flow) | Oxidizer to Flowcell | 18 |
| WASH (Acetonitrile Wash Flow) | Acetonitrile System Flush | 4 |
| | N2 System Flush | 4 |
| | Acetonitrile System Flush | 4 |
| | Acetonitrile to Flowcell | 15 |
| | Acetonitrile System Flush | 4 |
| | Acetonitrile to Flowcell | 15 |
| | N2 System Flush | 4 |
| | Acetonitrile System Flush | 4 |
| | Acetonitrile to Flowcell | 23 |
| | N2 System Flush | 4 |
| | Acetonitrile System Flush | 4 |
| DEBLOCKING (Deblock Flow) | Deblock to Flowcell | 36 |
| WASH (Acetonitrile Wash Flow) | Acetonitrile System Flush | 4 |
| | N2 System Flush | 4 |
| | Acetonitrile System Flush | 4 |
| | Acetonitrile to Flowcell | 18 |
| | N2 System Flush | 4.13 |
| | Acetonitrile System Flush | 4.13 |
| | Acetonitrile to Flowcell | 15 |

The phosphoramidite/activator combination was delivered similar to the delivery of bulk reagents through the flowcell. No drying steps were performed as the environment stays "wet" with reagent the entire time.

The flow restrictor was removed from the ABI 394 synthesizer to enable faster flow. Without flow restrictor, flow rates for amidites (0.1M in ACN), Activator, (0.25M Benzoyithiotetrazole ("BTT"; 30-3070-xx from GlenResearch) in ACN), and Ox (0.02M 12 in 20% pyridine, 10% water, and 70% THF) were roughly ~100 uL/sec, for acetonitrile ("ACN") and capping reagents (1:1 mix of CapA and CapB, wherein CapA is acetic anhydride in THF/Pyridine and CapB is 16% 1-methylimidizole in THF), roughly ~200 uL/sec, and for Deblock (3% dichloroacetic acid in toluene), roughly ~300 uL/sec (compared to ~50 uL/sec for all reagents with flow restrictor). The time to completely push out Oxidizer was observed, the timing for chemical flow times was adjusted accordingly and an extra ACN wash was introduced between different chemicals. After polynucleotide synthesis, the chip was deprotected in gaseous ammonia overnight at 75 psi. Five drops of water were applied to the surface to recover polynucleotides. The recovered polynucleotides were then analyzed on a BioAnalyzer small RNA chip.

Example 3: Synthesis of a 100 Racer Sequence on an Oligonucleotide Synthesis Device The same process as described in Example 2 for the synthesis of the 50-mer sequence was used for the synthesis of a 100-mer polynucleotide ("100-mer polynucleotide"; 5' CGGGATCCTTATCGTCATCGTCGTACA-GATCCCGACCCATTTGCTGTCCACCAGTCATG CTAGCCATACCATGATGATGATGATGAGAACCC CGCAT##TTTTTTTTTT3' (SEQ ID NO: 47), where #denotes Thymidine-succinyl CED phosphoramidite (CLP-2244 from ChemGenes) on two different silicon chips, the first one uniformly functionalized with N-(3-TRIETHOX-YSILYLPROPYL)-4-HYDROXYBUTYRAMIDE and the second one functionalized with 5/95 mix of 11-acetoxyundecyltriethoxysilane and n-decyltriethoxysilane, and the polynucleotides extracted from the surface were analyzed on a BioAnalyzer instrument.

All ten samples from the two chips were further PCR amplified using a forward (5'ATGCGGGGTTCTCAT-CATC3') (SEQ ID NO: 48) and a reverse (5'CGGGATCCI-TATCGTCATCG3') (SEQ ID NO: 49) primer in a 50 uL PCR mix 5 uL NEB Q5 mastermix, 2.5 uL 10 uM Forward primer, 2.5 uL 10 uM Reverse primer, 1 uL polynucleotide extracted from the surface, and water up to 50 uL) using the following thermalcycling program:

98° C., 30 sec
98° C., 10 sec; 63° C., 10 sec; 72° C., 10 sec; repeat 12 cycles
72° C., 2 min The PCR products were also run on a BioAnalyzer, demonstrating sharp peaks at the 100-mer position. Next, the PCR amplified samples were cloned, and Sanger sequenced. Table 3 summarizes the results from the Sanger sequencing for samples taken from spots 1-5 from chip 1 and for samples taken from spots 6-10 from chip 2.

TABLE 3

Sequencing results

| Spot | Error rate | Cycle efficiency |
|---|---|---|
| 1 | 1/763 bp | 99.87% |
| 2 | 1/824 bp | 99.88% |
| 3 | 1/780 bp | 99.87% |
| 4 | 1/429 bp | 99.77% |
| 5 | 1/1525 bp | 99.93% |
| 6 | 1/1615 bp | 99.94% |
| 7 | 1/531 bp | 99.81% |
| 8 | 1/1769 bp | 99.94% |

TABLE 3-continued

Sequencing results

| Spot | Error rate | Cycle efficiency |
|---|---|---|
| 9 | 1/854 bp | 99.88% |
| 10 | 1/1451 bp | 99.93% |

Thus, the high quality and uniformity of the synthesized polynucleotides were repeated on two chips with different surface chemistries. Overall, 89% of the 100-mers that were sequenced were perfect sequences with no errors, corresponding to 233 out of 262.

Table 4 summarizes error characteristics for the sequences obtained from the polynucleotide samples from spots 1-10.

TABLE 4

Error characterstics

| | Sample ID/Spot no. | | | | | | | | | |
|---|---|---|---|---|---|---|---|---|---|---|
| | OSA_0 046/1 | OSA_0 047/2 | OSA_0 048/3 | OSA_0 049/4 | OSA_0 050/5 | OSA_0 051/6 | OSA_0 052/7 | OSA_0 053/8 | OSA_0 054/9 | OSA_00 55/10 |
| Total Sequences | 32 | 32 | 32 | 32 | 32 | 32 | 32 | 32 | 32 | 32 |
| Sequencing Quality | 25 of 28 | 27 of 27 | 26 of 30 | 21 of 23 | 25 of 26 | 29 of 30 | 27 of 31 | 29 of 31 | 28 of 29 | 25 of 28 |
| Oligo Quality | 23 of 25 | 25 of 27 | 22 of 26 | 18 of 21 | 24 of 25 | 25 of 29 | 22 of 27 | 28 of 29 | 26 of 28 | 20 of 25 |
| ROI Match Count | 2500 | 2698 | 2561 | 2122 | 2499 | 2666 | 2625 | 2899 | 2798 | 2348 |
| ROI Mutation | 2 | 2 | 1 | 3 | 1 | 0 | 2 | 1 | 2 | 1 |
| ROI Multi Base Deletion | 0 | 0 | 0 | 0 | 0 | 0 | 0 | 0 | 0 | 0 |
| ROI Small Insertion | 1 | 0 | 0 | 0 | 0 | 0 | 0 | 0 | 0 | 0 |
| ROI Single Base Deletion | 0 | 0 | 0 | 0 | 0 | 0 | 0 | 0 | 0 | 0 |
| Large Deletion Count | 0 | 0 | 1 | 0 | 0 | 1 | 1 | 0 | 0 | 0 |
| Mutation: G > A | 2 | 2 | 1 | 2 | 1 | 0 | 2 | 1 | 2 | 1 |
| Mutation: T > C | 0 | 0 | 0 | 1 | 0 | 0 | 0 | 0 | 0 | 0 |
| ROI Error Count | 3 | 2 | 2 | 3 | 1 | 1 | 3 | 1 | 2 | 1 |
| ROI Error Rate ROI MP | Err: ~1 in 834 | Err: ~1 in 1350 | Err: ~1 in 1282 | Err: ~1 in 708 | Err: ~1 in 2500 | Err: ~1 in 2667 | Err: ~1 in 876 | Err: ~1 in 2900 | Err: ~1 in 1400 | Err: ~1 in 2349 |
| Minus Primer Error Rate | Err: ~1 in 763 | Err: ~1 in 824 | Err: ~1 in 780 | Err: ~1 in 429 | Err: ~1 in 1525 | Err: ~1 in 1615 | Err: ~1 in 531 | Err: ~1 in 1769 | Err: ~1 in 854 | Err: ~1 in 1451 |

Example 4: VHH Libraries

Synthetic VHH libraries were developed. For the 'VHH Ratio' library with tailored CDR diversity, 2391 VHH sequences (iCAN database) were aligned using Clustal Omega to determine the consensus at each position and the framework was derived from the consensus at each position. The CDRs of all of the 2391 sequences were analyzed for position-specific variation, and this diversity was introduced in the library design. For the 'VHH Shuffle' library with shuffled CDR diversity, the iCAN database was scanned for unique CDRs in the nanobody sequences. 1239 unique CDR1's, 1600 unique CDR2's, and 1608 unique CDR3's were identified and the framework was derived from the consensus at each framework position amongst the 2391 sequences in the iCAN database. Each of the unique CDR's was individually synthesized and shuffled in the consensus framework to generate a library with theoretical diversity of 3.2×10^9, The library was then cloned in the phagemid vector using restriction enzyme digest. For the 'VHH hShuffle' library (a synthetic "human" VHH library with shuffled CDR diversity), the iCAN database was scanned for unique CDRs in the nanobody sequences, 1239 unique CDR1's, 1600 unique CDR2's, and 1608 unique CDR3's were identified and framework 1, 3, and 4 was derived from the human germline DP-47 framework. Framework 2 was derived from the consensus at each framework position amongst the 2391 sequences in the iCAN database. Each of the unique CDR's was individually synthesized and shuffled in the partially humanized framework using the NUGE tool to generate a library with theoretical diversity of 3.2×10^9. The library was then cloned in the phagemid vector using the NUGE tool.

Figure 6:
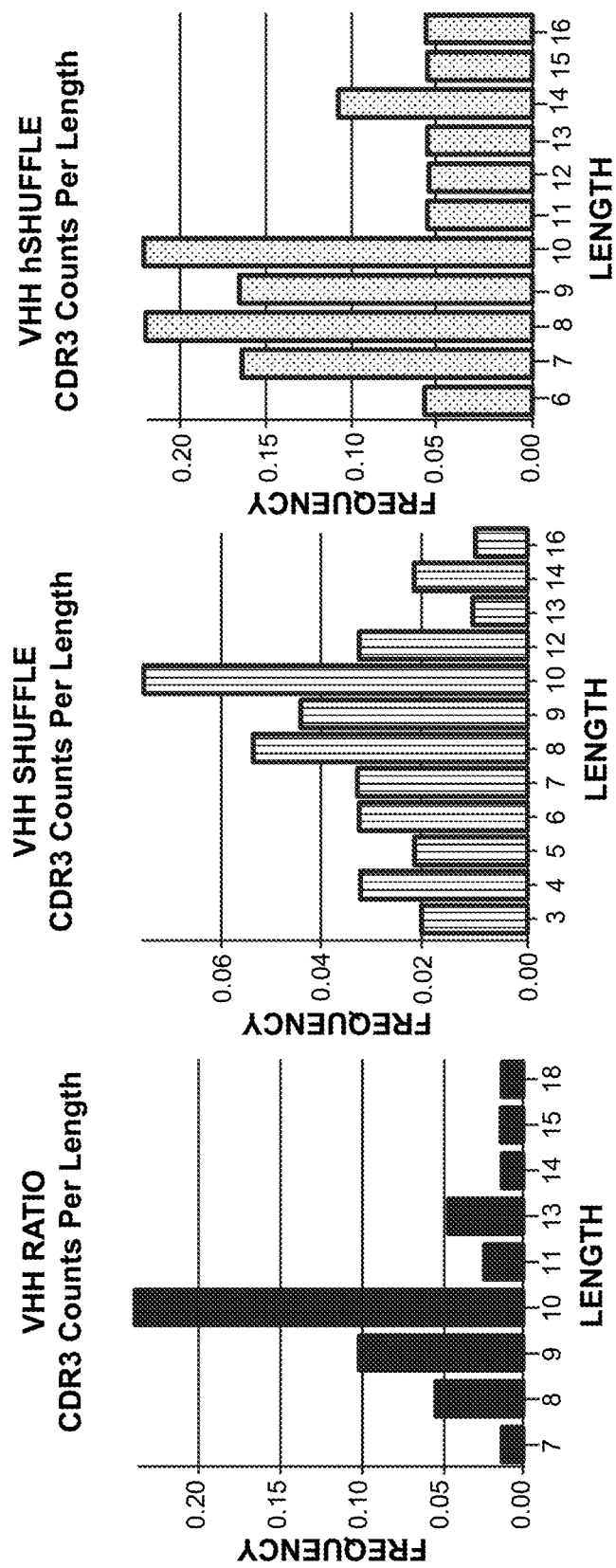
FIGS. 6A-6C depict graphs of CDR3 counts per length for 'VHH library' (FIG. 6A) 'VHH shuffle' library (FIG. 6B), and 'VHH hShuffle library' (FIG. 6C).

The Carterra™ SPR system was used to assess binding; affinity and affinity distribution for VHH-Fc variants. Table 5 provides specific values for the VHH-Fc clones for ELISA, Protein A (mg/ml), and $K_D$ (nM). FIG. 6 shows data of CDR3 counts per length for the 'VHH ratio' library, the 'VHH shuffle library,' and the 'VHH hShuffle library.'

TABLE 5

| Clone | ELISA | Library | ProA (mg/ml) | $K_D$ (nM) |
|---|---|---|---|---|
| 31-1 | 5.7 | VHH hShuffle | 0.29 | 12 |
| 31-6 | 9.6 | VHH hShuffle | 0.29 | 14 |
| 31-26 | 5.1 | VHH hShuffle | 0.31 | 19 |
| 30-30 | 8.0 | VHH Shuffle | 0.11 | 23 |
| 31-32 | 8.0 | VHH hShuffle | 0.25 | 27 |
| 29-10 | 5.0 | VHH Ratio | 0.19 | 32 |
| 29-7 | 7.3 | VHH Ratio | 0.28 | 41 |
| 30-43 | 13.5 | VHH Shuffle | 0.18 | 44 |
| 31-8 | 12.7 | VHH hShuffle | 0.29 | 45 |
| 31-56 | 11.7 | VHH hShuffle | 0.26 | 46 |
| 30-52 | 4.2 | VHH Shuffle | 0.22 | 49 |
| 31-47 | 8.8 | VHH hShuffle | 0.23 | 53 |
| 30-15 | 9.3 | VHH Shuffle | 0.26 | 55 |
| 30-54 | 5.5 | VHH Shuffle | 0.30 | 58 |
| 30-49 | 10.3 | VHH Shuffle | 0.26 | 62 |
| 29-22 | 3.4 | VHH Ratio | 0.27 | 65 |
| 29-30 | 9.2 | VHH Ratio | 0.28 | 65 |
| 31-35 | 5.7 | VHH hShuffle | 0.24 | 66 |
| 29-1 | 10.4 | VHH Ratio | 0.09 | 68 |
| 29-6 | 6.8 | VHH Ratio | 0.29 | 69 |
| 31-34 | 6.0 | VHH hShuffle | 0.32 | 70 |
| 29-12 | 6.2 | VHH Ratio | 0.23 | 70 |
| 30-1 | 5.4 | VHH Shuffle | 0.39 | 71 |
| 29-33 | 3.9 | VHH Ratio | 0.15 | 74 |
| 30-20 | 4.6 | VHH Shuffle | 0.19 | 74 |
| 31-20 | 6.6 | VHH hShuffle | 0.37 | 74 |
| 31-24 | 3.1 | VHH hShuffle | 0.15 | 75 |
| 30-14 | 9.9 | VHH Shuffle | 0.19 | 75 |
| 30-53 | 7.6 | VHH Shuffle | 0.24 | 78 |
| 31-39 | 9.9 | VHH hShuffle | 0.32 | 78 |
| 29-18 | 10.9 | VHH Ratio | 0.19 | 78 |
| 30-9 | 8.0 | VHH Shuffle | 0.40 | 79 |
| 29-34 | 8.6 | VHH Ratio | 0.21 | 80 |
| −29-27 | 8.6 | VHH Ratio | 0.18 | 82 |
| 29-20 | 5.9 | VHH Ratio | 0.26 | 83 |
| 30-55 | 6.0 | VHH Shuffle | 0.41 | 85 |
| 30-39 | 6.1 | VHH Shuffle | 0.07 | 88 |
| 31-15 | 6.2 | VHH hShuffle | 0.32 | 88 |
| 29-21 | 4.3 | VHH Ratio | 0.23 | 88 |
| 29-37 | 5.3 | VHH Ratio | 0.26 | 89 |
| 29-40 | 6.6 | VHH Ratio | 0.31 | 90 |
| 31-30 | 3.2 | VHH hShuffle | 0.33 | 93 |
| 31-10 | 12.3 | VHH hShuffle | 0.31 | 94 |
| 29-3 | 13.6 | VHH Ratio | 0.11 | 94 |
| 30-57 | 5.2 | VHH Shuffle | 0.24 | 95 |
| 29-31 | 4.4 | VHH Ratio | 0.18 | 96 |
| 31-27 | 8.1 | VHH hShuffle | 0.31 | 96 |
| 31-33 | 6.0 | VHH hShuffle | 0.32 | 96 |
| 30-40 | 7.1 | VHH Shuffle | 0.21 | 99 |
| 31-18 | 4.1 | VHH hShuffle | 0.36 | 99 |
| 30-5 | 9.3 | VHH Shuffle | 0.05 | 100 |

Example 5. Hyperimmune Immunoglobulin Library

Figure 7:
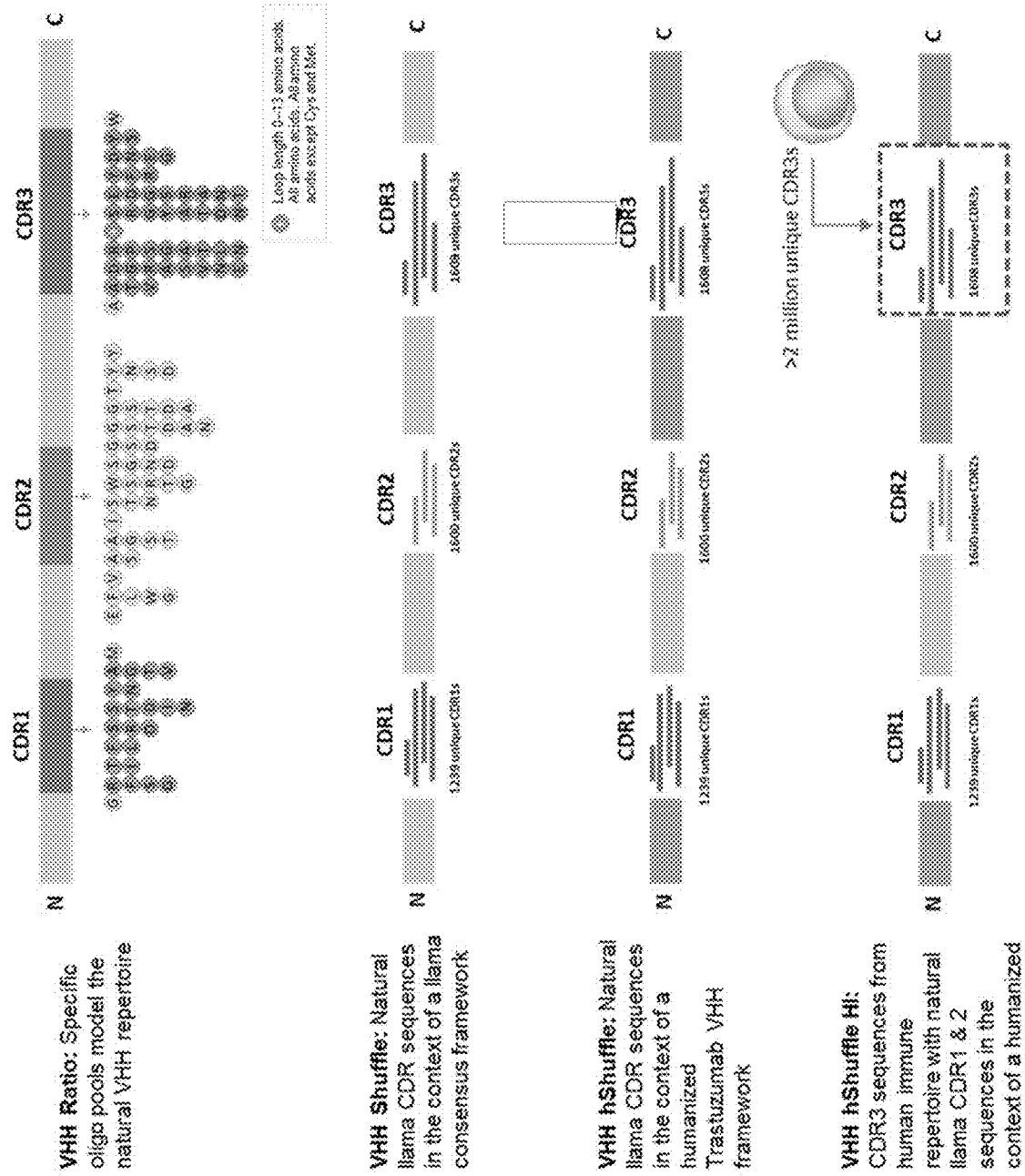
FIG. 7 depicts a schema of libraries generated herein. Figure discloses SEQ ID NO: 50.

A hyperimmune immunoglobulin (IgG) library was created using similar methods as described in Example 4. Briefly, the hyperimmune IgG library was generated from analysis of databases of human naïve and memory B-cell receptor sequences consisting of more than 37 million unique IgH sequences from each of 3 healthy donors. More than two million CDRH3 sequences were gathered from the analysis and individually constructed using methods similar to Examples 1-3. Any duplicate CDRH3's and potential liability motifs that frequently pose problems in development were removed during the library synthesis step. These CDRH3 sequence diversities were then combinatorially assembled and incorporated onto the DP47 human framework to construct a highly functional antibody Fab library with $1 \times 10^{10}$ size. A schematic of the design can be seen in FIGS. 7-8.

Figure 9A:
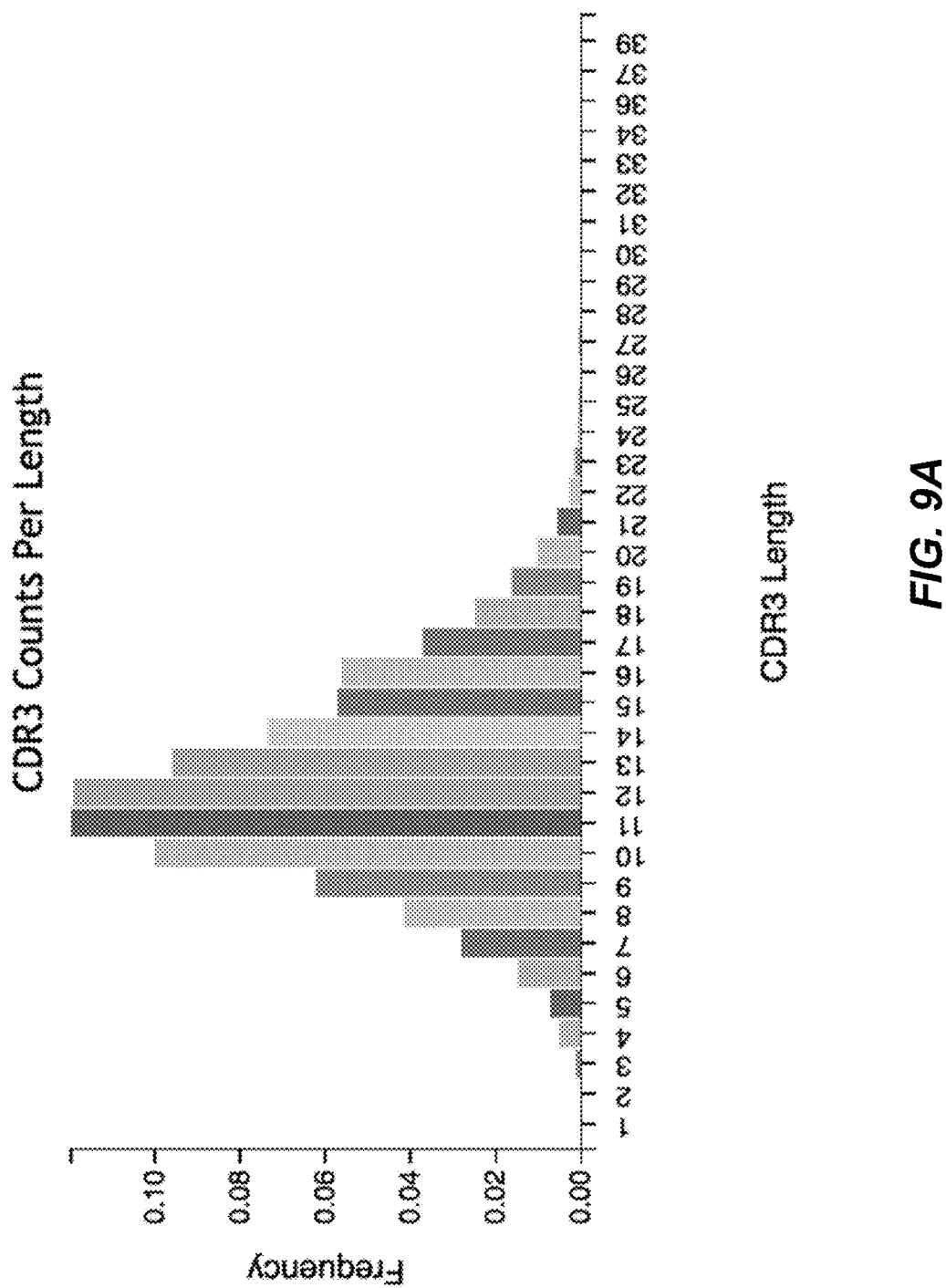
FIGS. 9A-9B depict heavy chain CDR length distribution of the hyperimmune libraries as assessed by next generation sequencing.
Figure 9B:
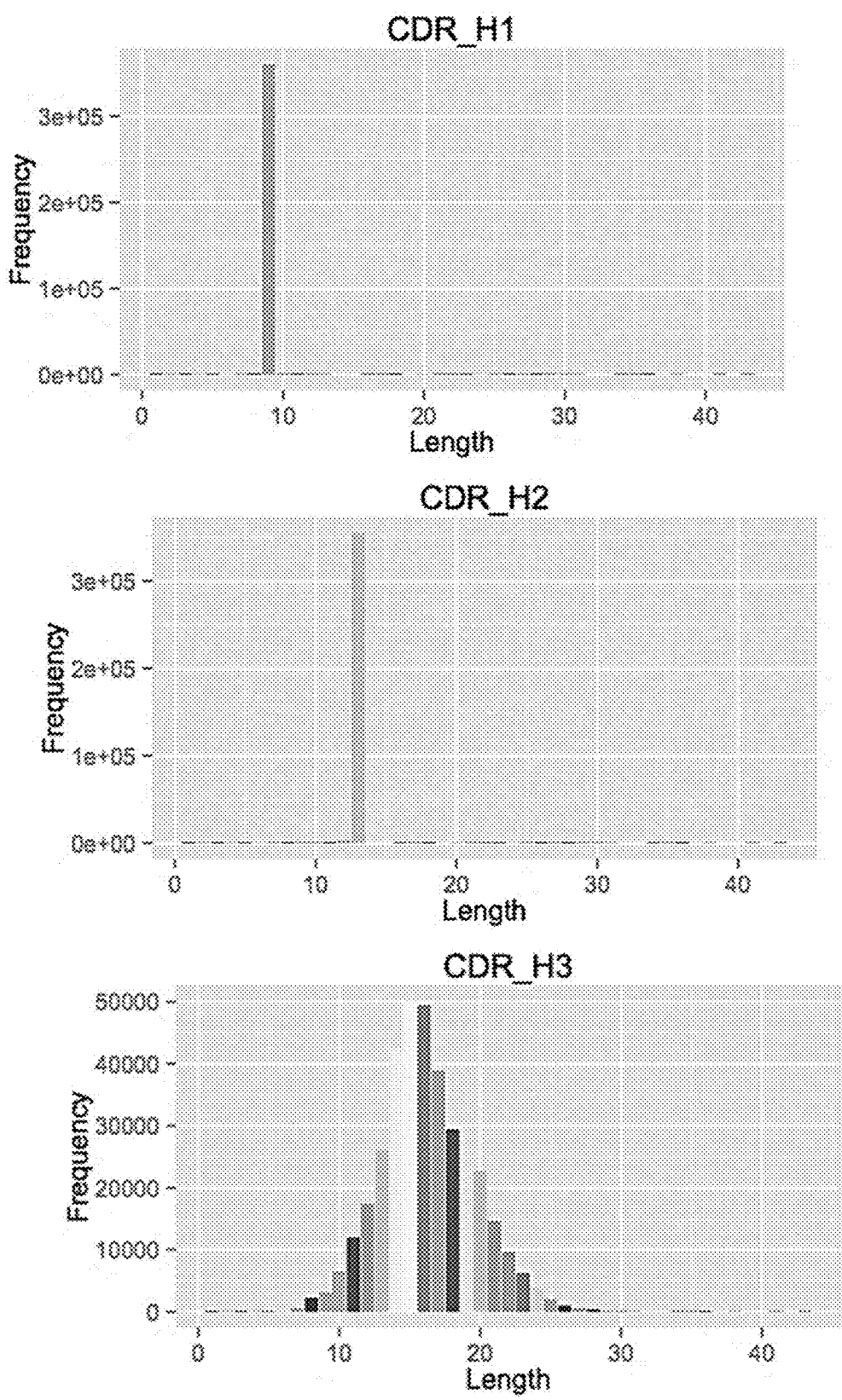
Figure 10:
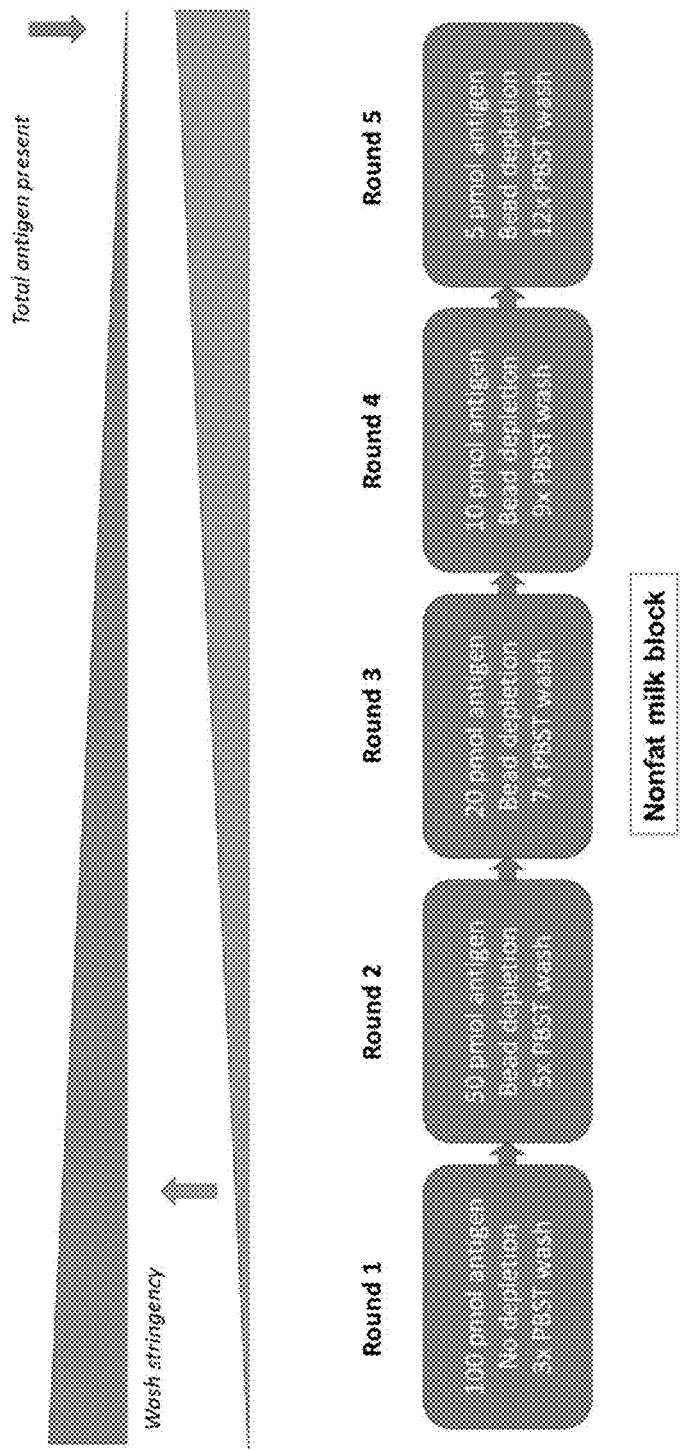
FIG. 10 depicts a schema of the workflow of selection of soluble protein targets.

The heavy chain CDR length distribution of the hyperimmune antibody libraries were assessed by next generation sequencing (NGS). The data of CDR length distribution is shown in FIGS. 9A-9B. Generally, selection of soluble protein targets undergo five rounds of selection involving a PBST wash three times in Round 1, a PBST wash five times in Round 2, a PBST wash seven times in Round 3, a PBST wash nine times in Round 4, and a PBST wash twelve times in Round 5. A non-fat milk block was used, See FIG. 10.

Identification of human CD3 epsilon (hCD3) and cyno CD3 epsilon (cCD3) immunoglobulins was performed. The details of the various rounds of selection are seen in Table 6.

TABLE 6

| Protein panning selection | | |
|---|---|---|
| Round | Washes | Concentration |
| Manual | | |
| 1 | 3 | 500 nM hCD3 and 500 nM cCD3 |
| 2 | 6 | 100 nM hCD3 |
| 3 | 9 | 50 nM hCD3 |
| 4 | 12 | 50 nM hCD3 |
| 5 | 12 | 10 nM hCD3 |
| Kingfisher (KF) | | |
| 1 | 2 | 500 nM hCD3 and 500 nM cCD3 |
| 2 | 4 | 100 nM hCD3 |
| 3 | 6 | 50 nM hCD3 |
| 4 | 8 | 50 nM hCD3 |
| 5 | 8 | 10 nM hCD3 |

Figure 11A:
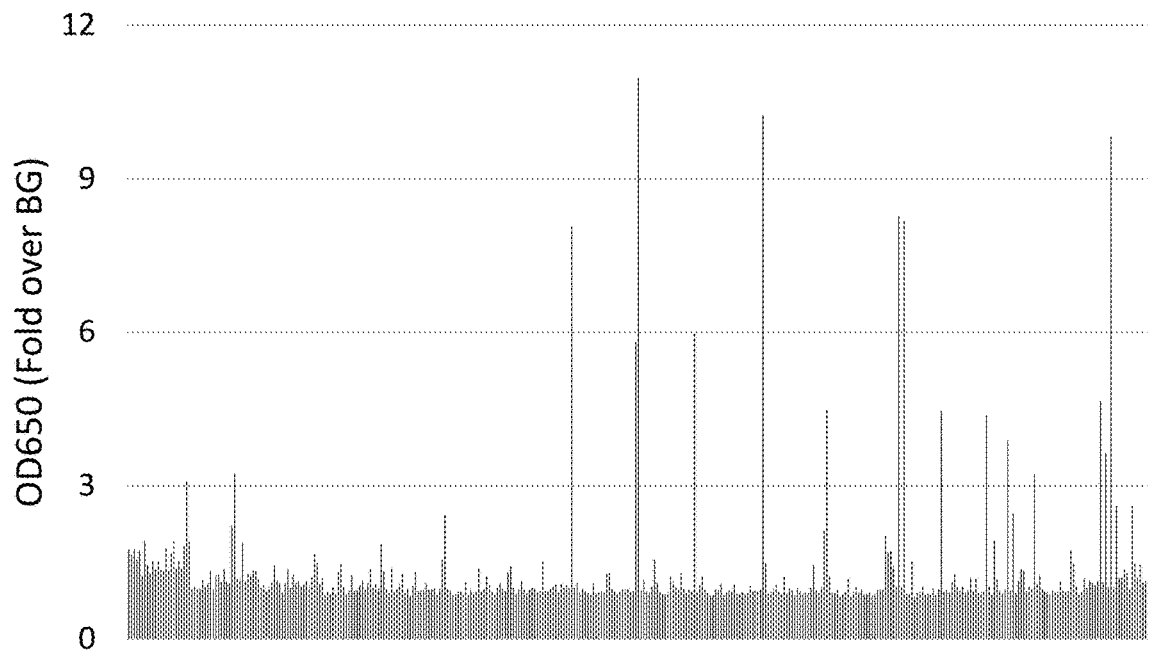
FIGS. 11A-11D depict graphs of data from human CD3 epsilon (hCD3) and cyno CD3 epsilon (cCD3) ELISA after Round 4 and Round 5 of panning.
Figure 11B:
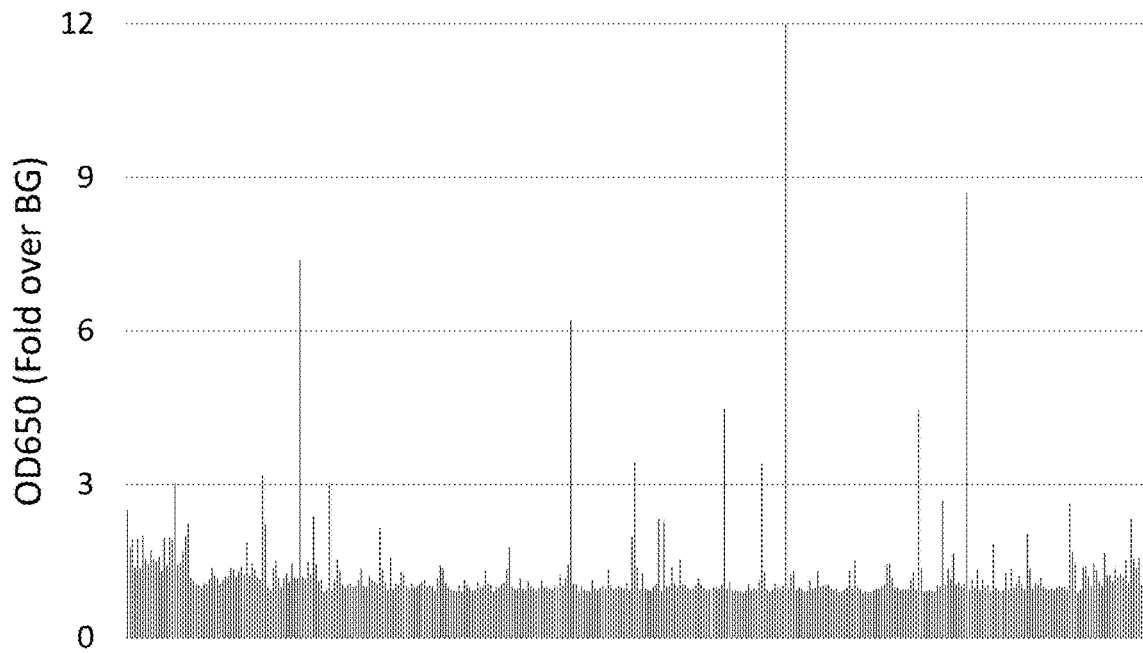
Figure 11C:
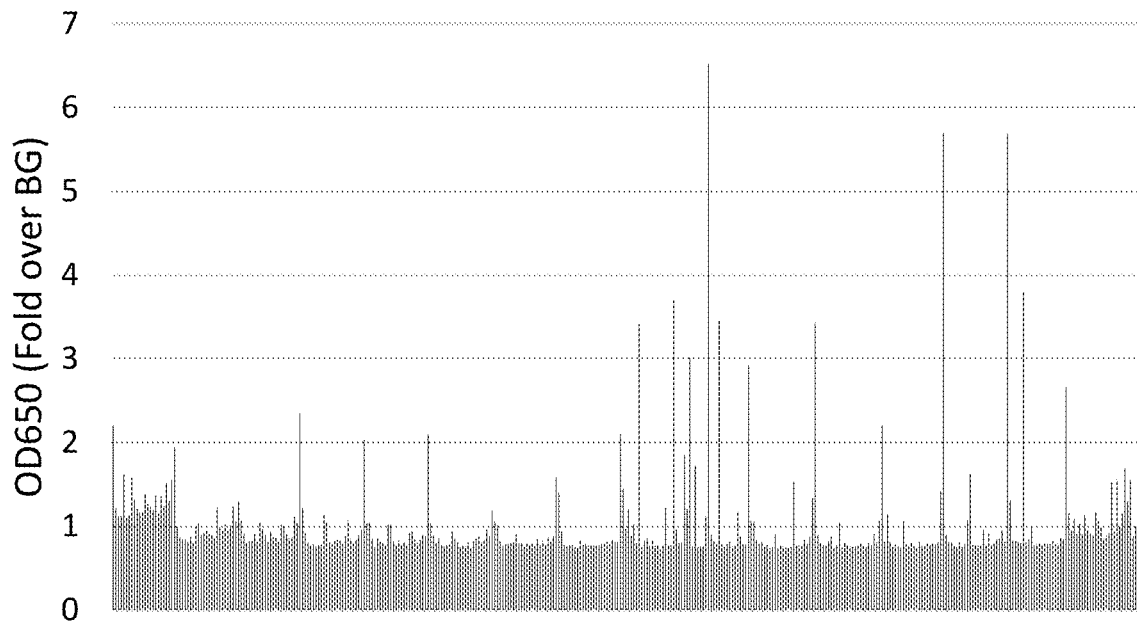
Figure 11D:
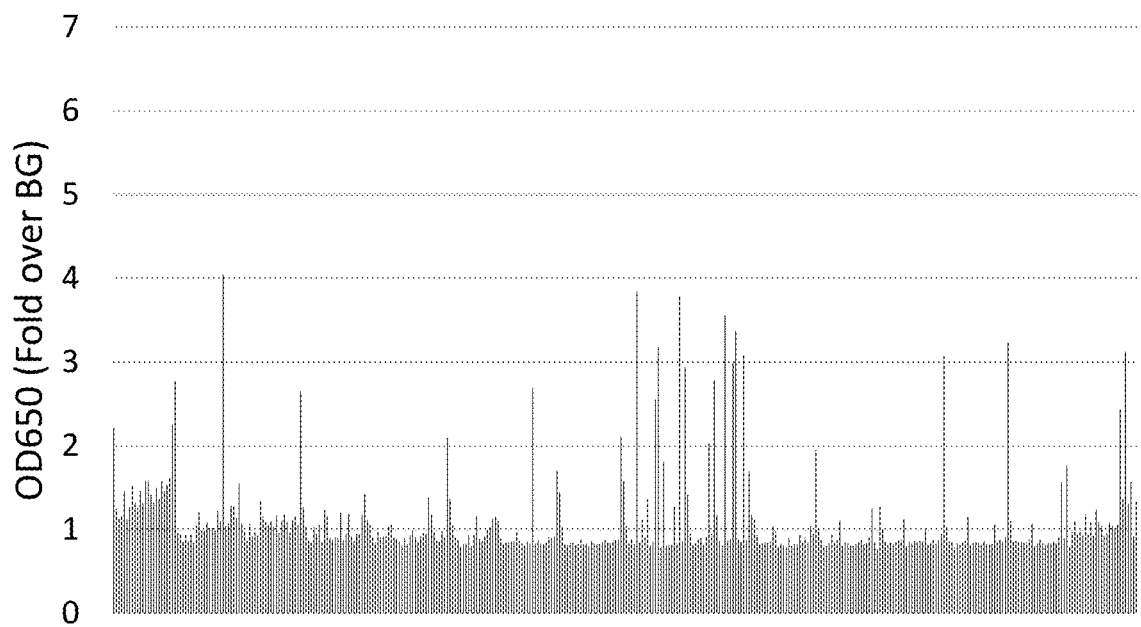
Figure 11E:
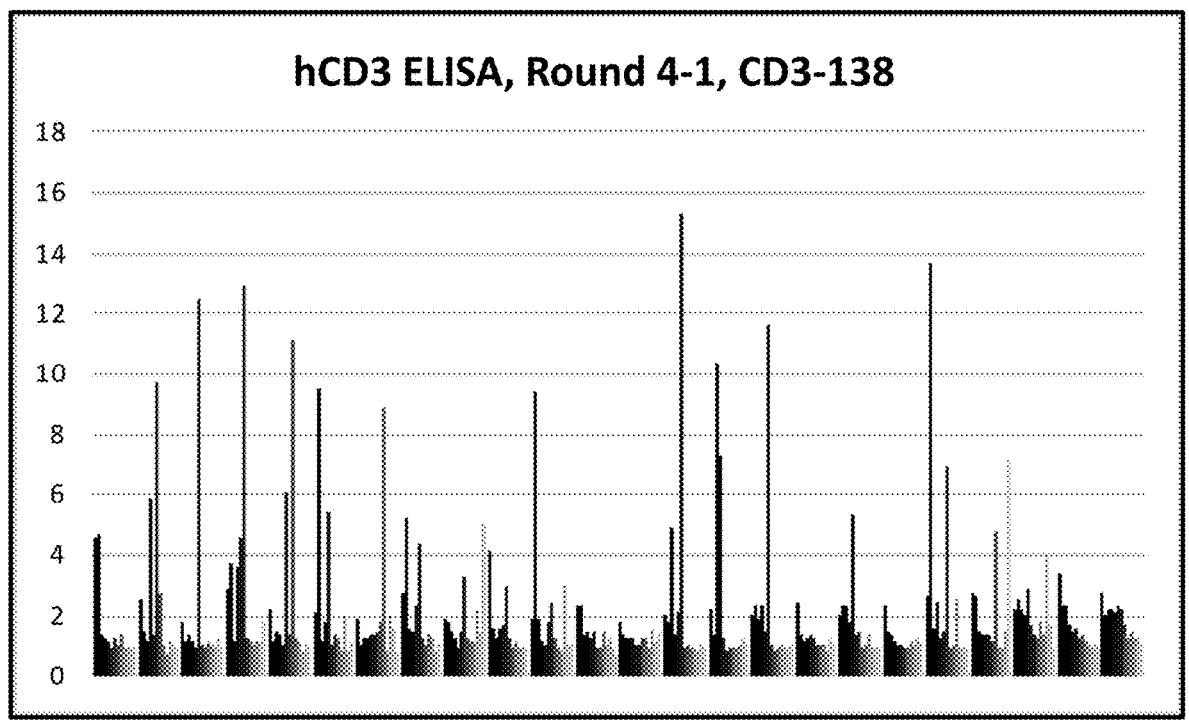
FIGS. 11E-11N depict graphs of cross-reactive human CD3 epsilon (hCD3) and cyno CD3 epsilon (cCD3) immunoglobulins.
Figure 11F:
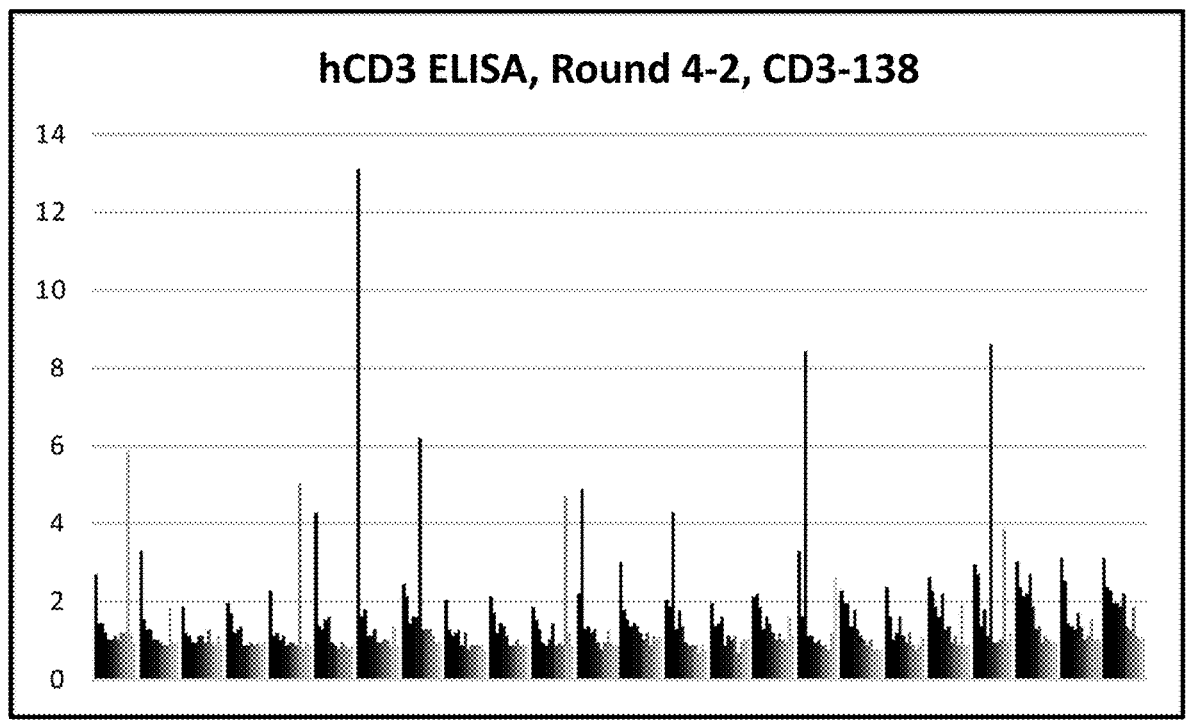
Figure 11G:
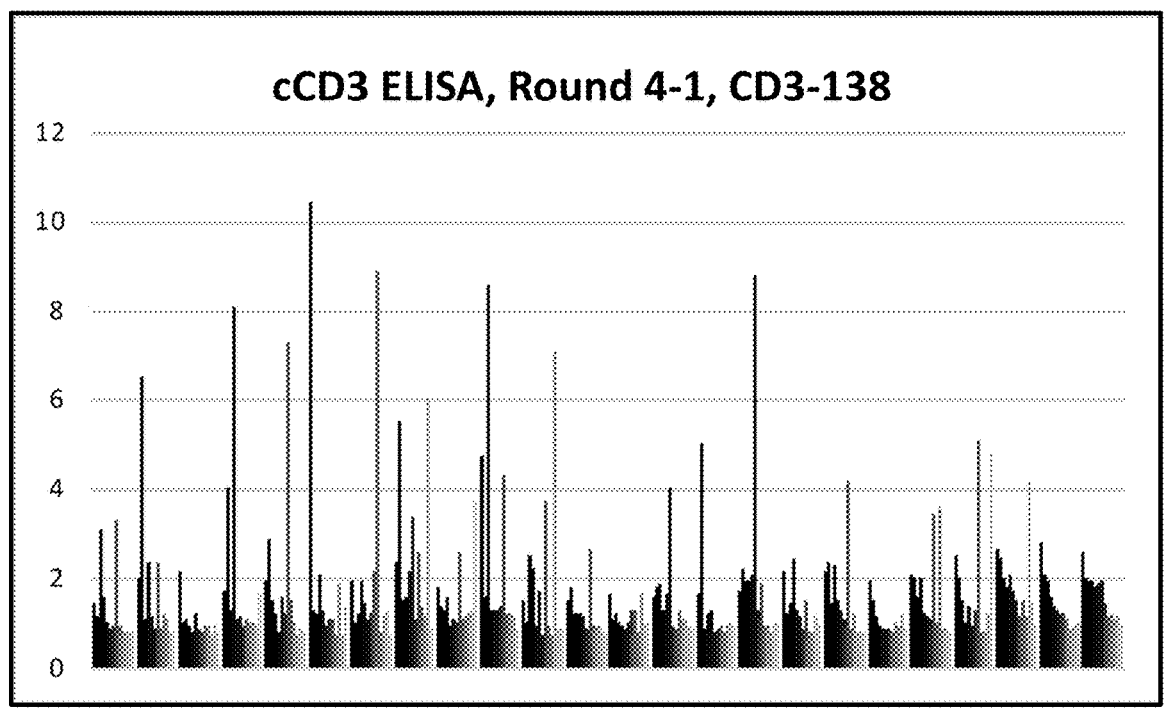
Figure 11H:
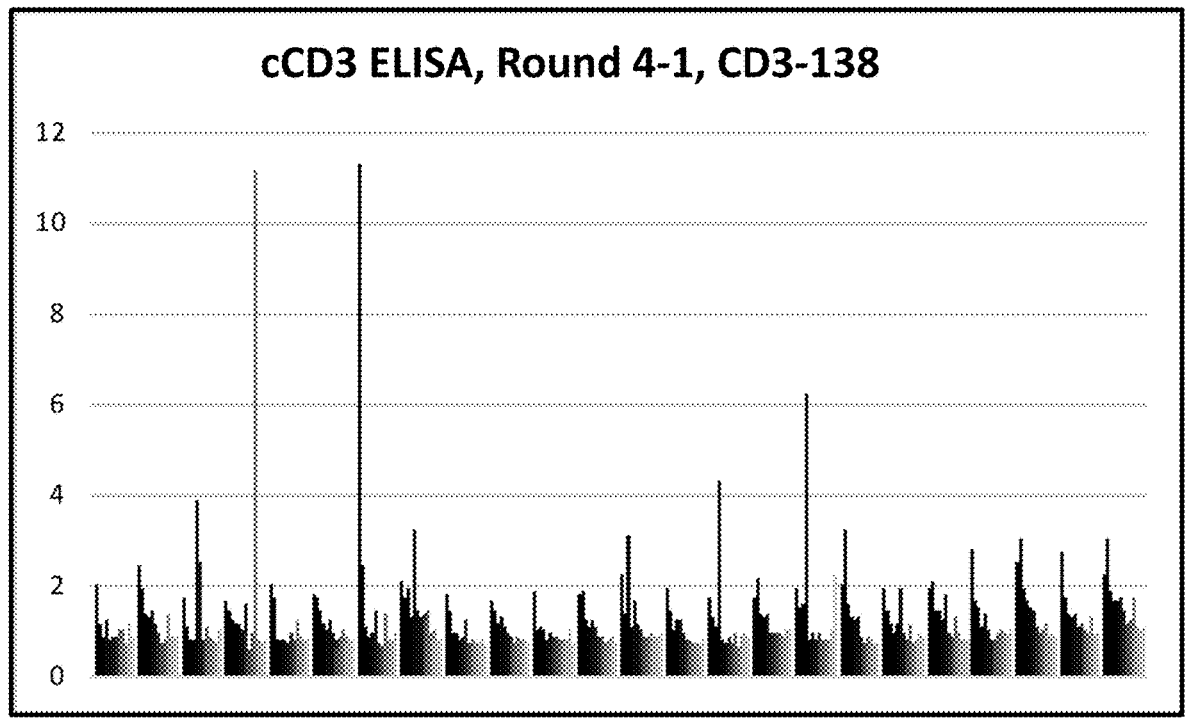
Figure 11I:
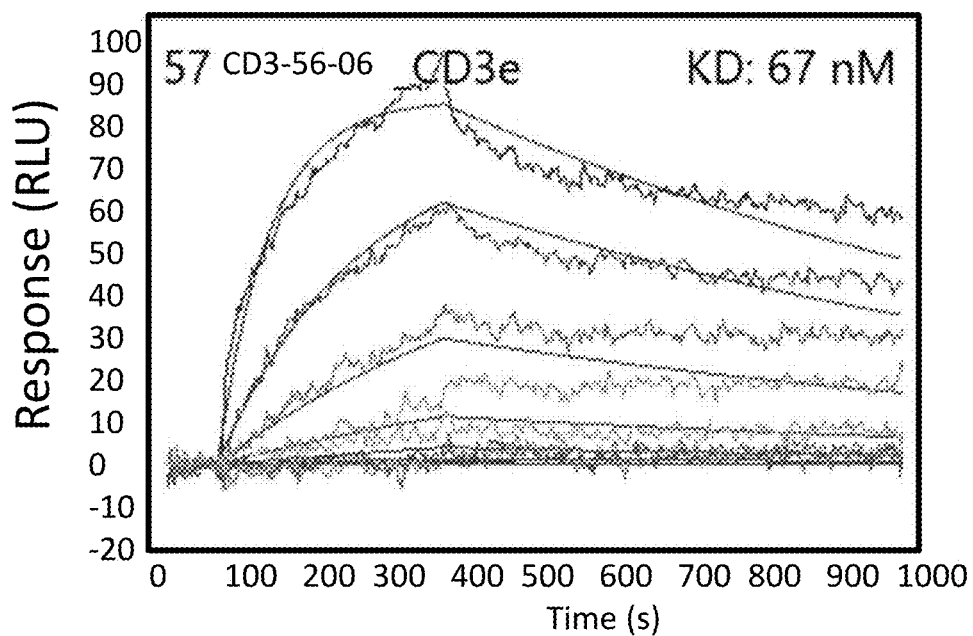
Figure 11J:
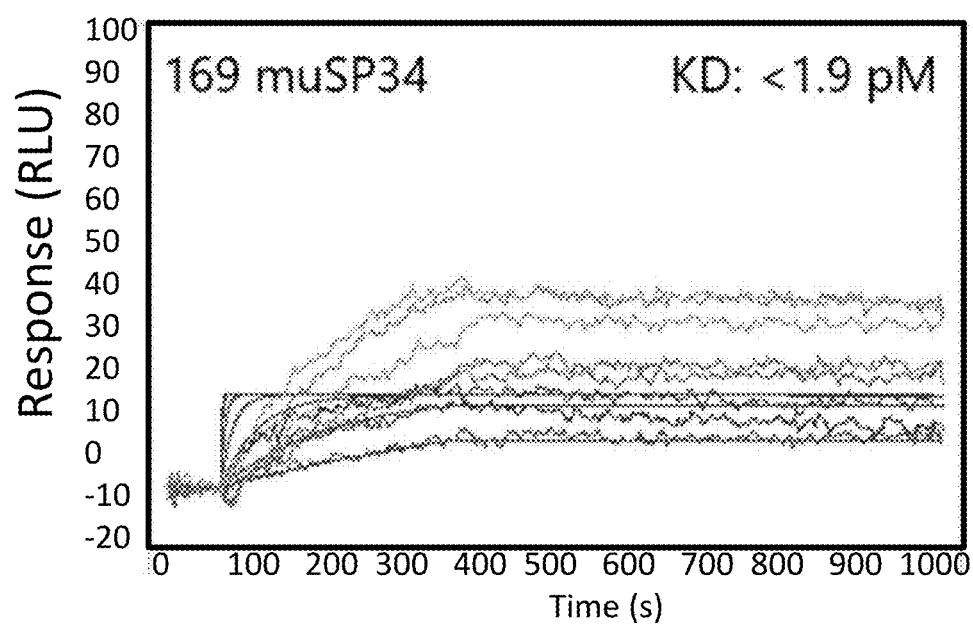
Figure 11K:
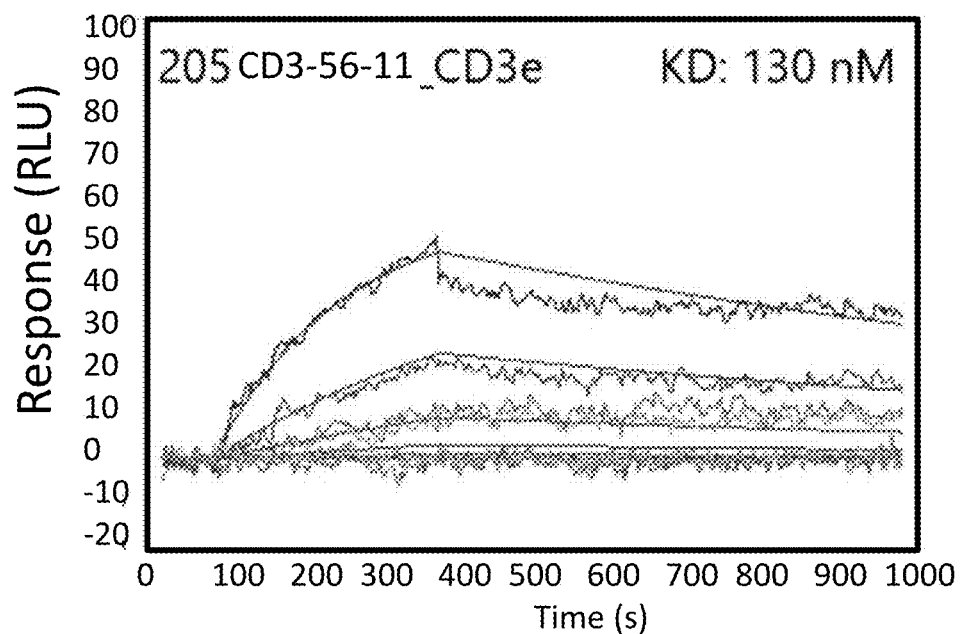
Figure 11L:
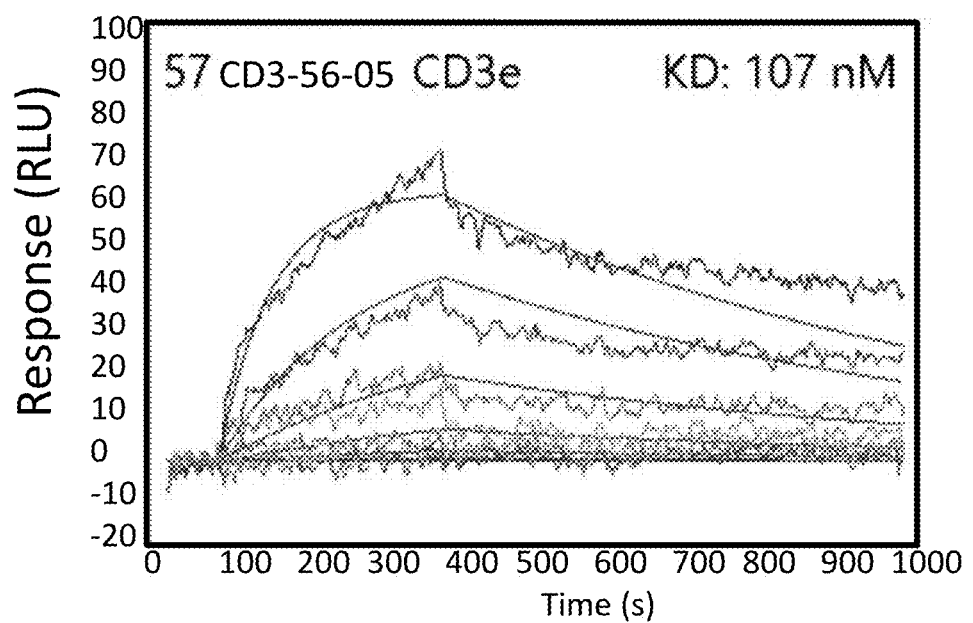
Figure 11M:
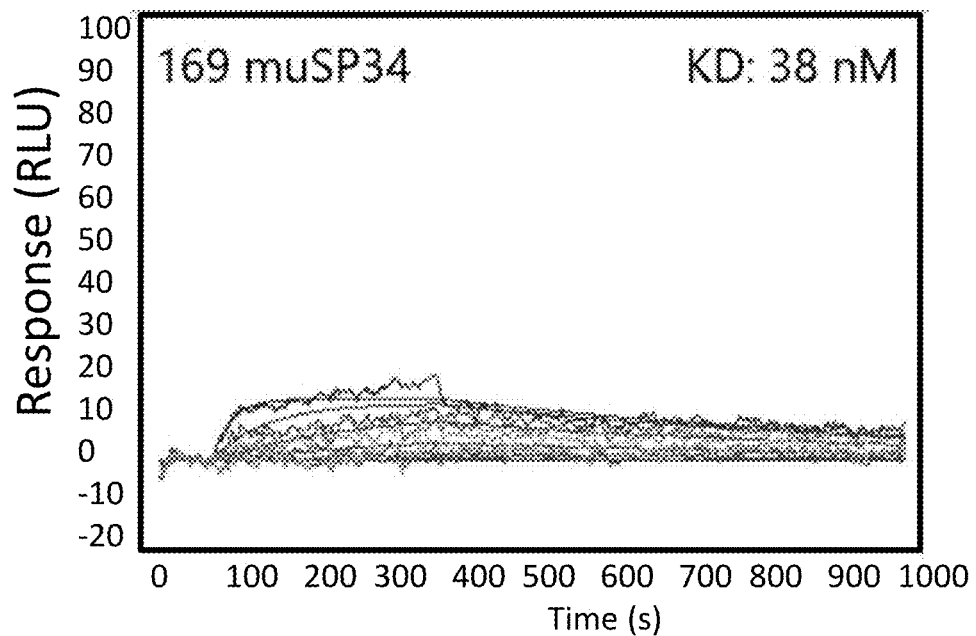
Figure 11N:
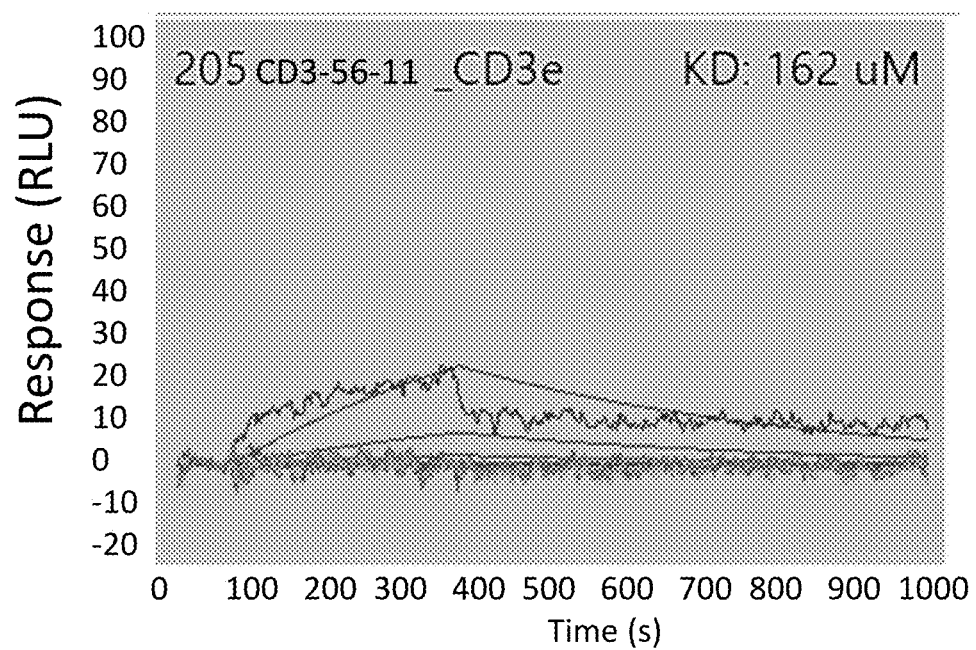
Figure 11O:
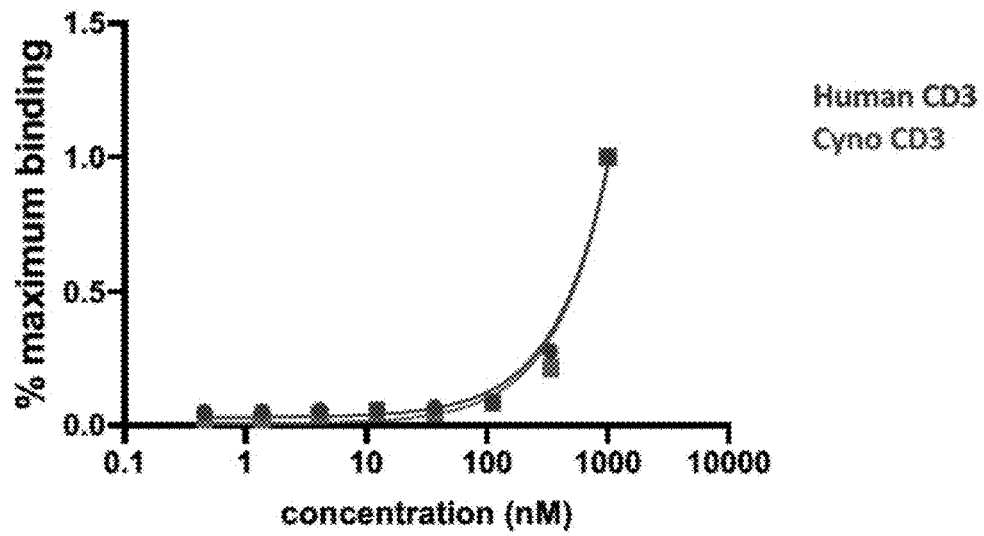
FIGS. 11O-11P depict graphs of CD3-138-6 and CD3-155-3 binding to CD3.
Figure 11P:
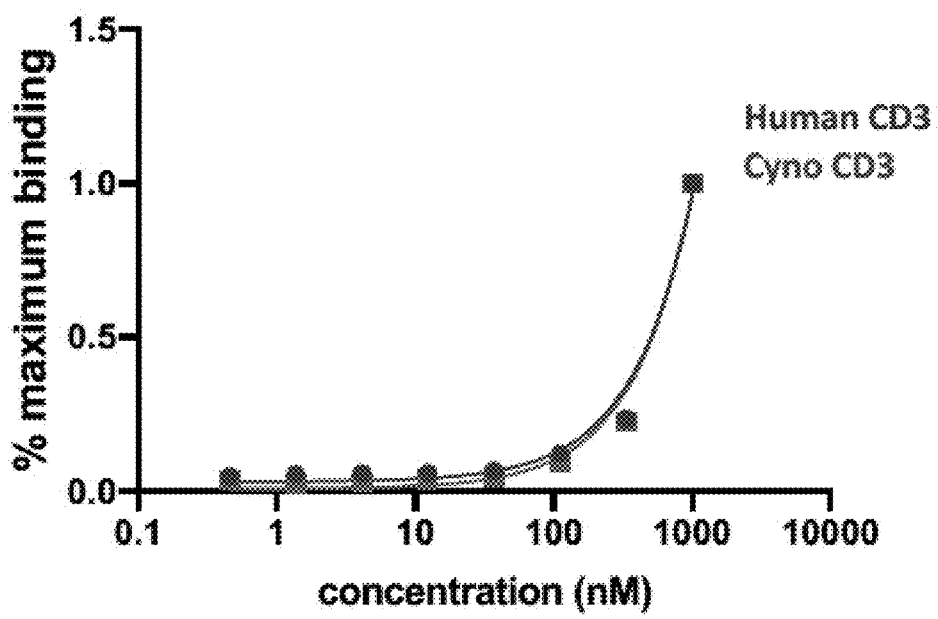
Figure 12A:
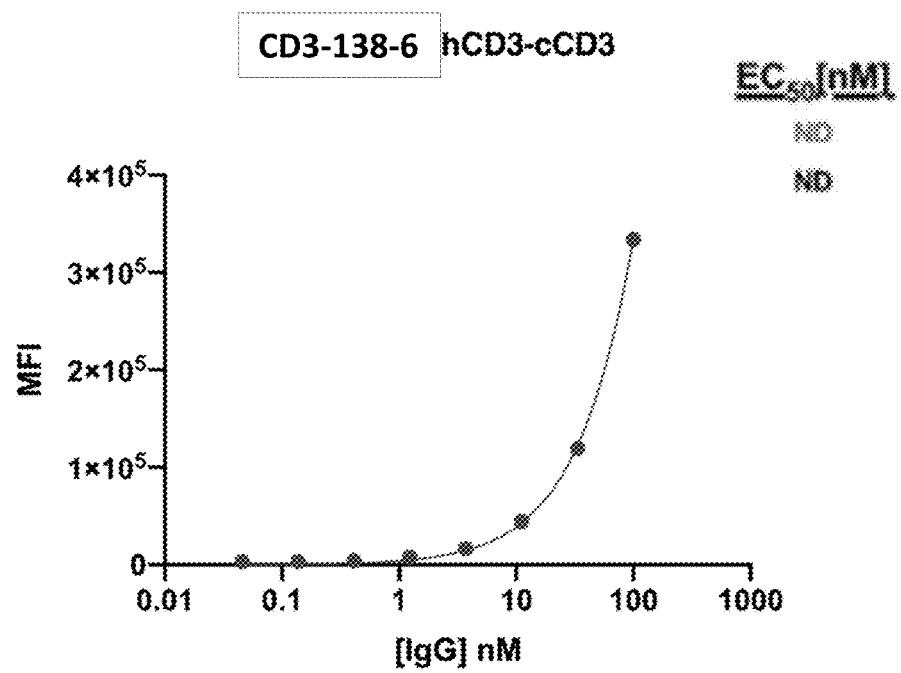
FIGS. 12A-12G depict graphs of titration of human CD3 on CD8+, CD3+, and CD3− T cells.
Figure 12B:
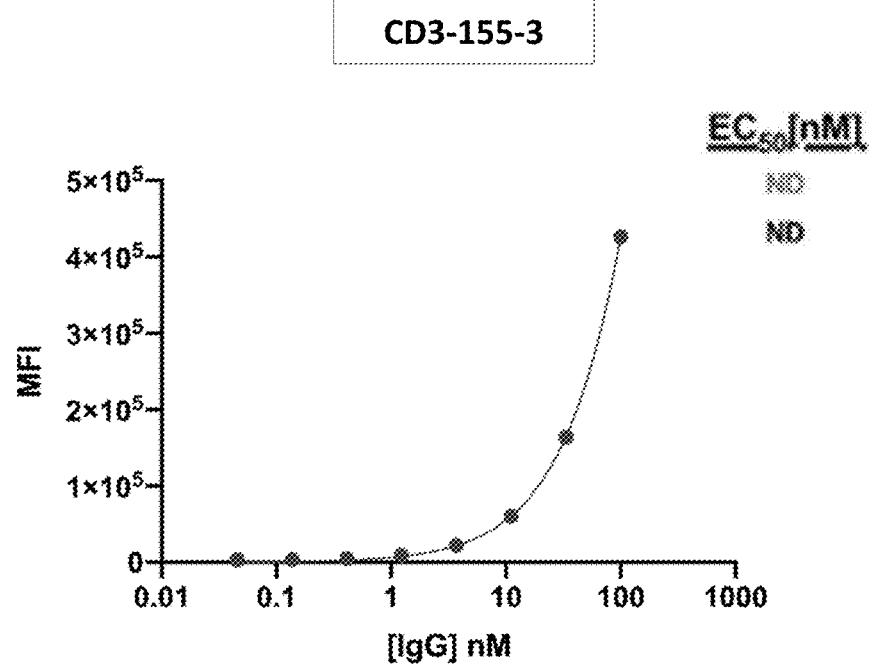
Figure 12C:
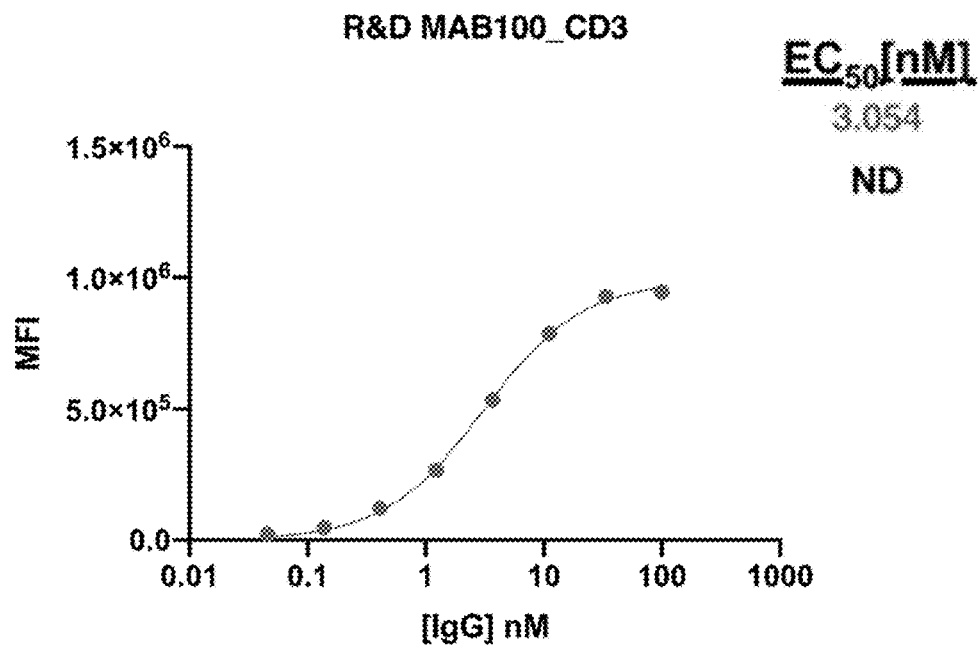
Figure 12D:
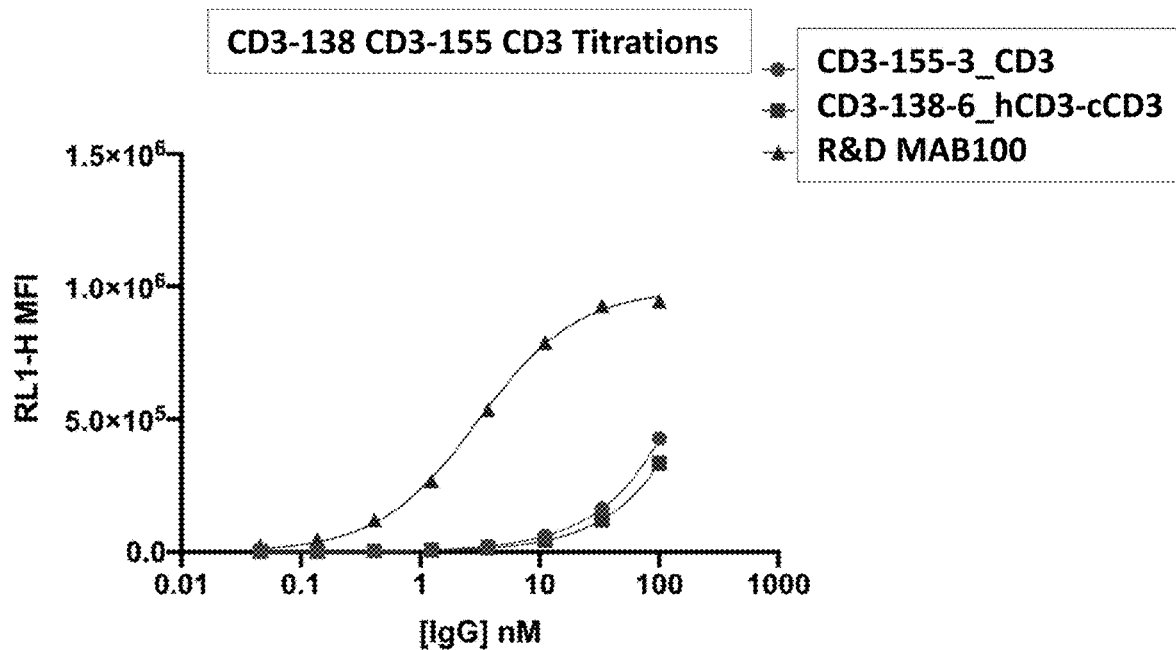
Figure 12E:
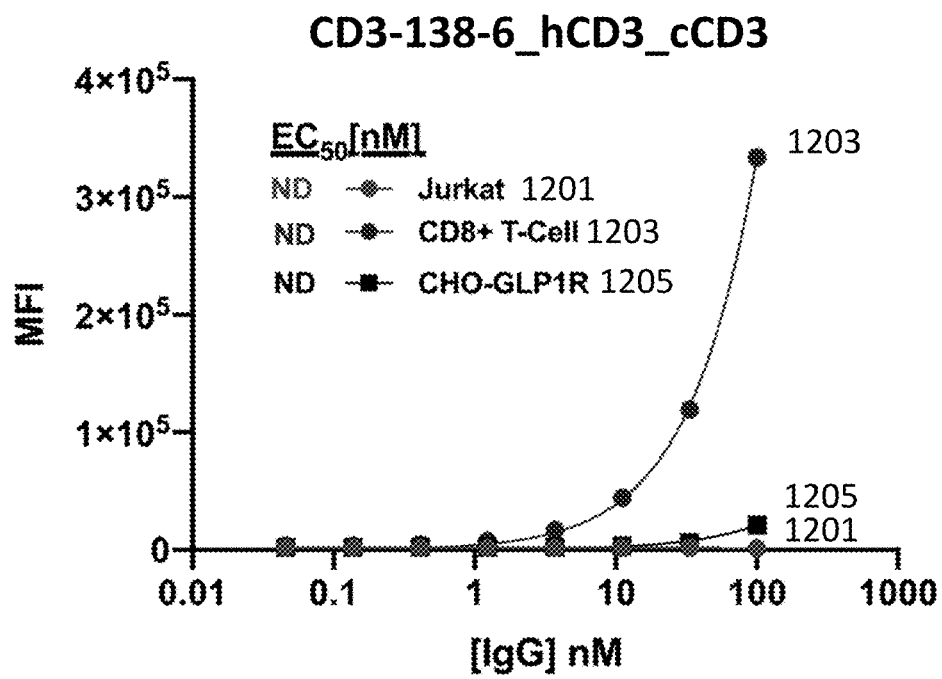
Figure 12F:
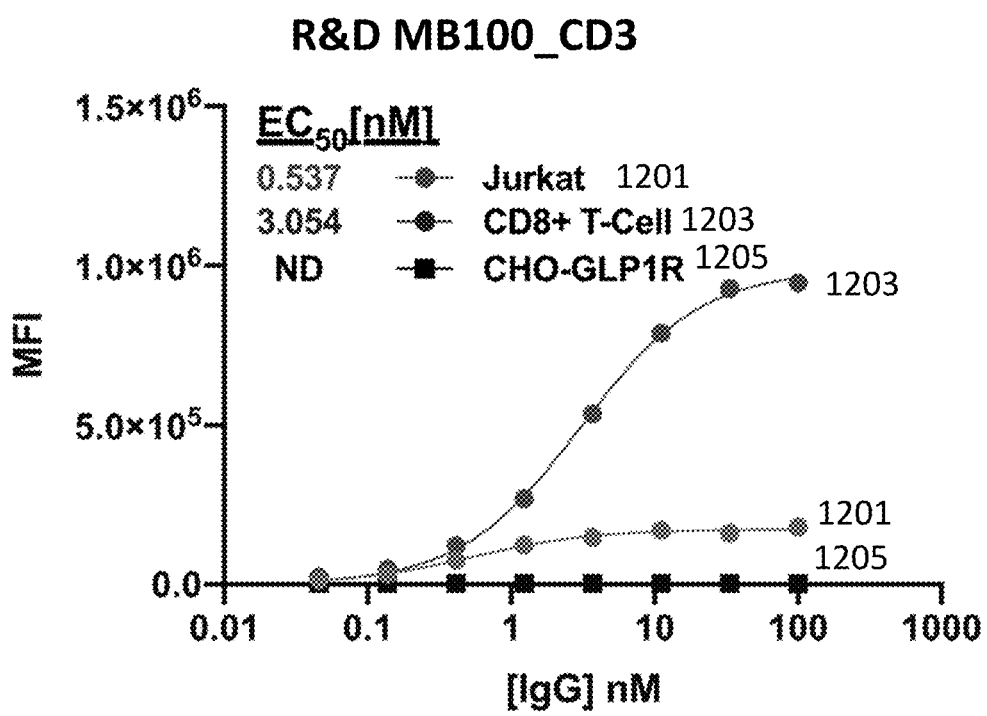
Figure 12G:
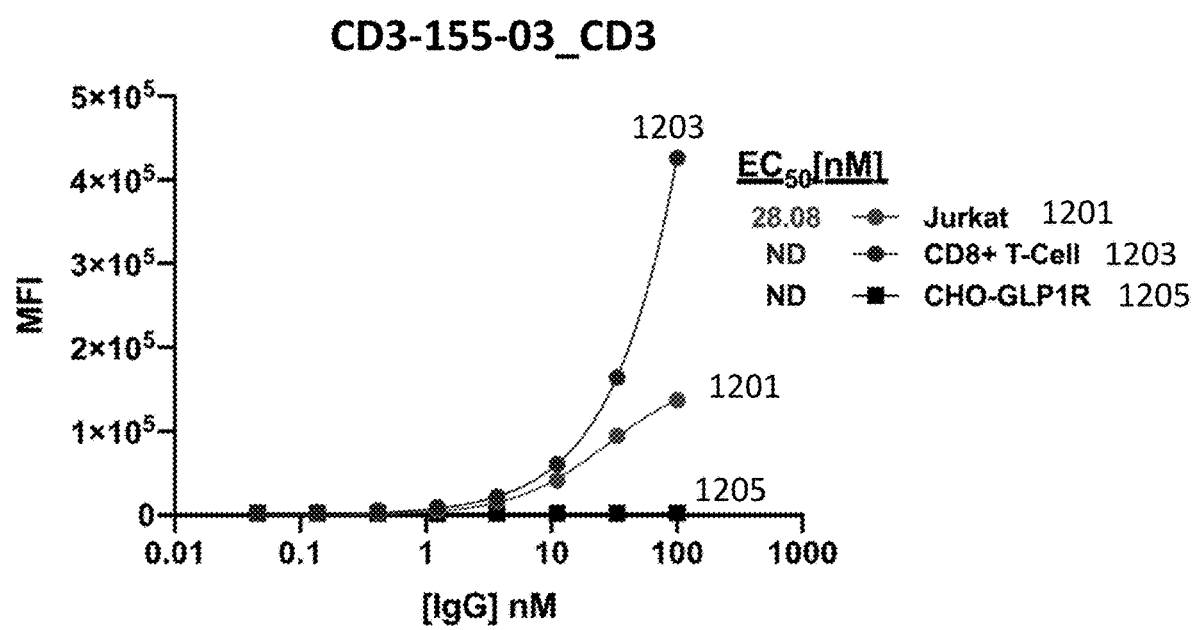
Figure 13A:
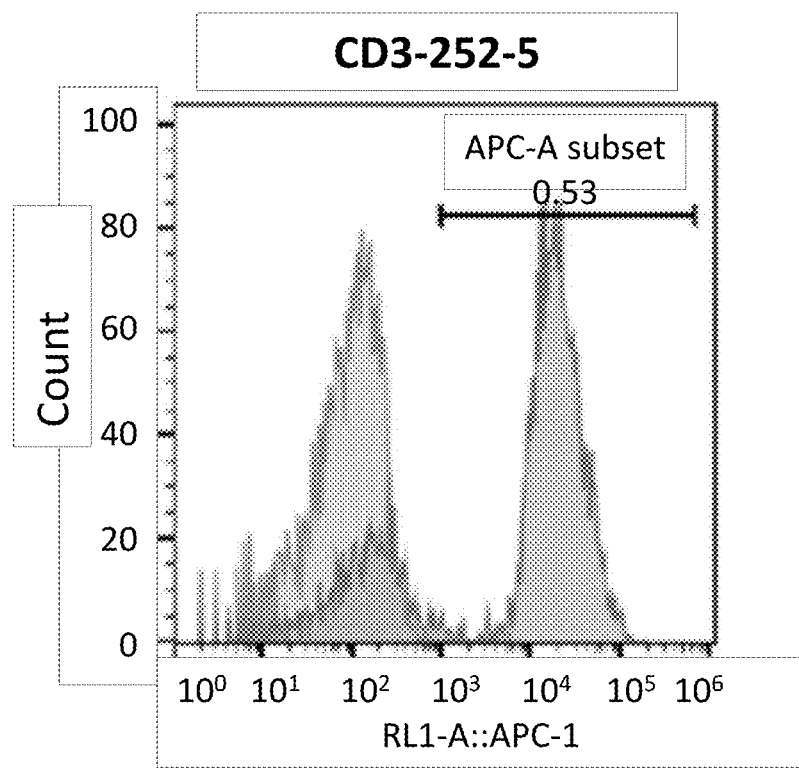
FIGS. 13A-13H depict flow cytometry graphs for CD3-252-5 (FIG. 13A), CD3-252-10 (FIG. 13B), CD3-252-17 (FIG. 13C), CD3-252-19 (FIG. 13D), CD3-252-22 (FIG. 13E), CD3-252-24 (FIG. 13F), CD3-252-29 (FIG. 13G), and CD3-252-31 (FIG. 13H).
Figure 13B:
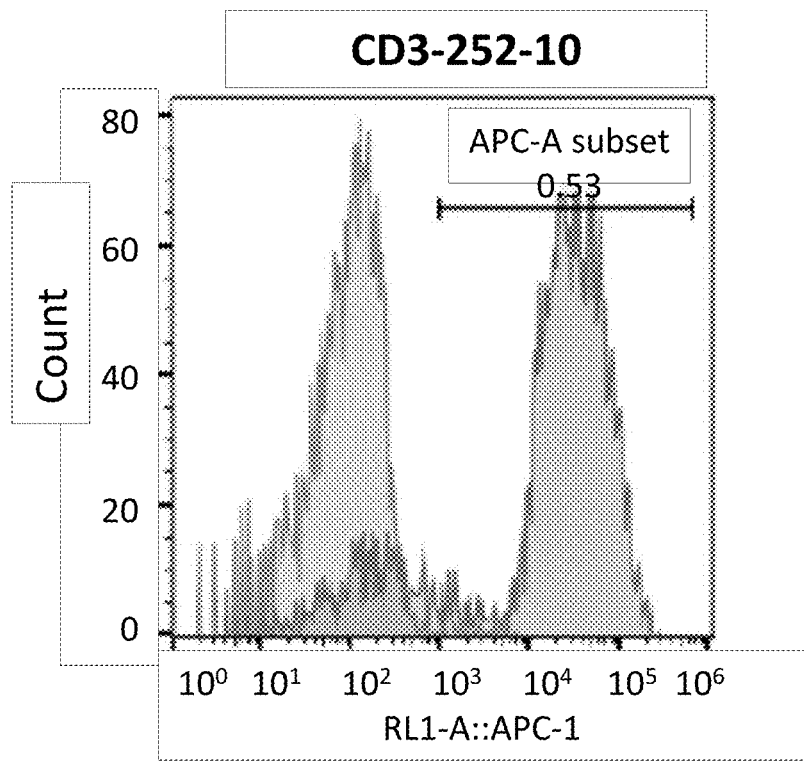
Figure 13C:
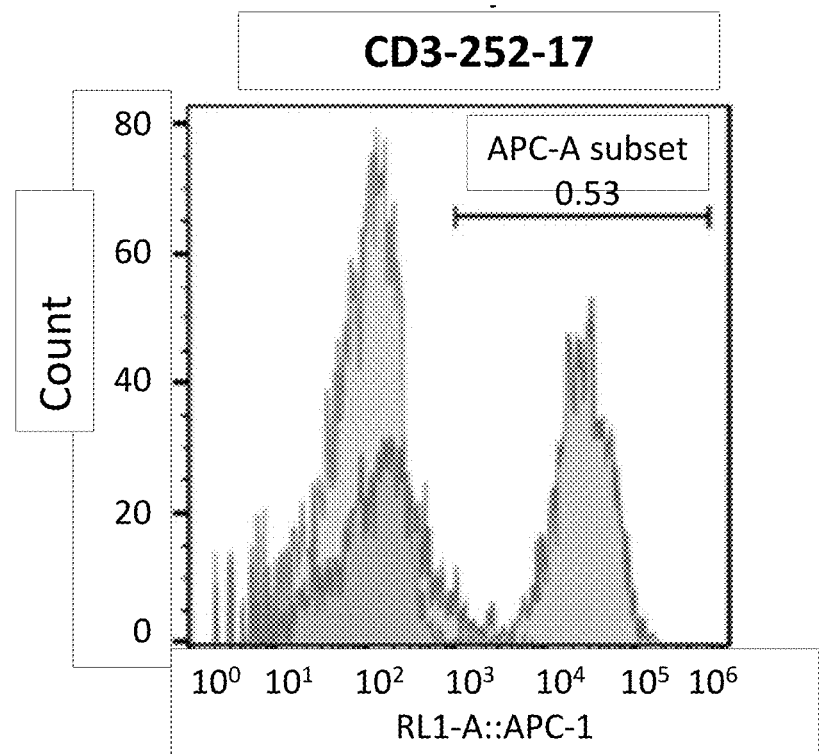
Figure 13D:
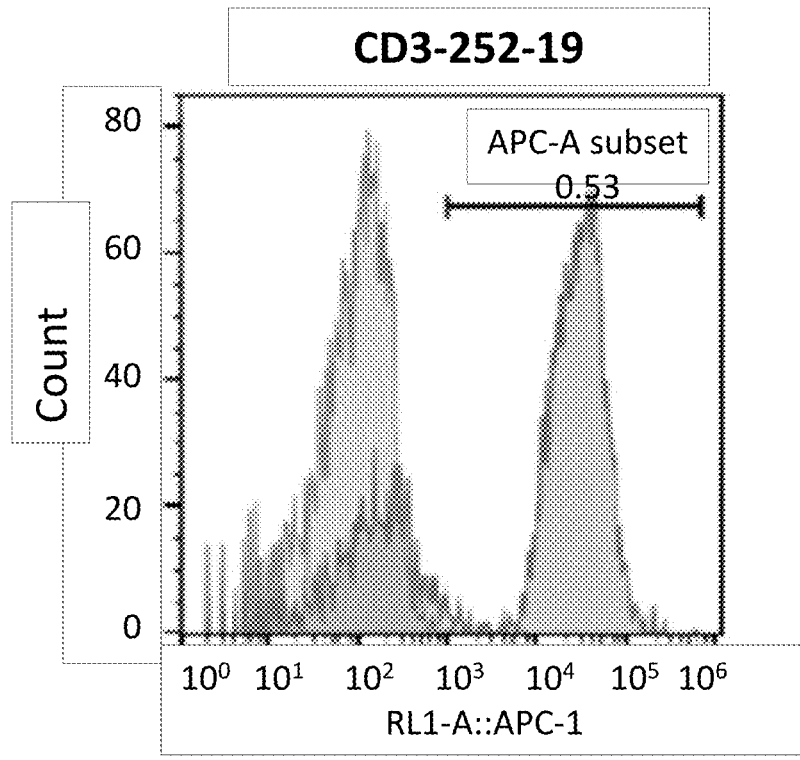
Figure 13E:
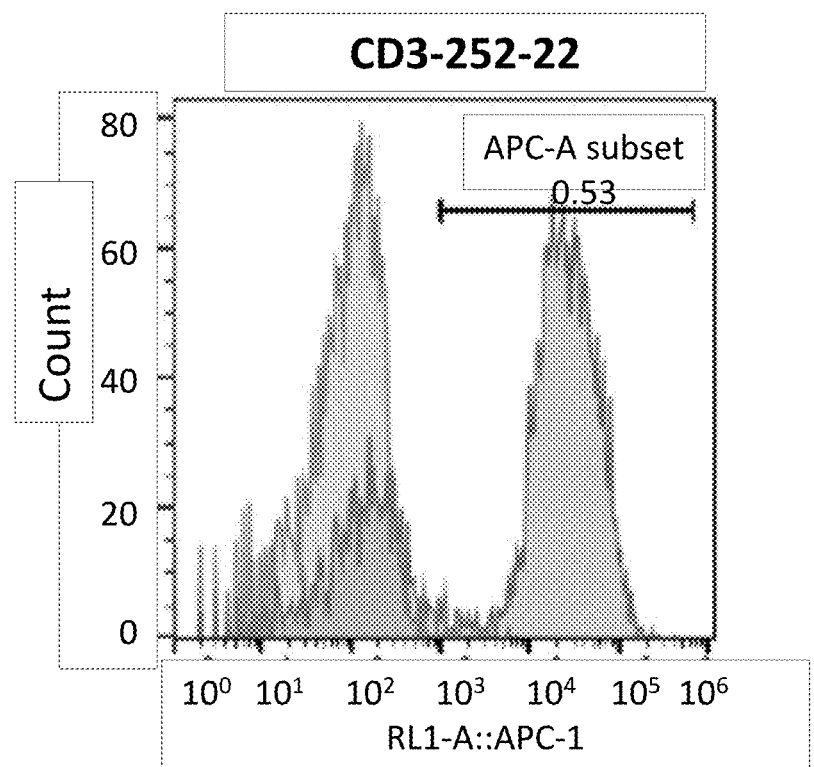
Figure 13F:
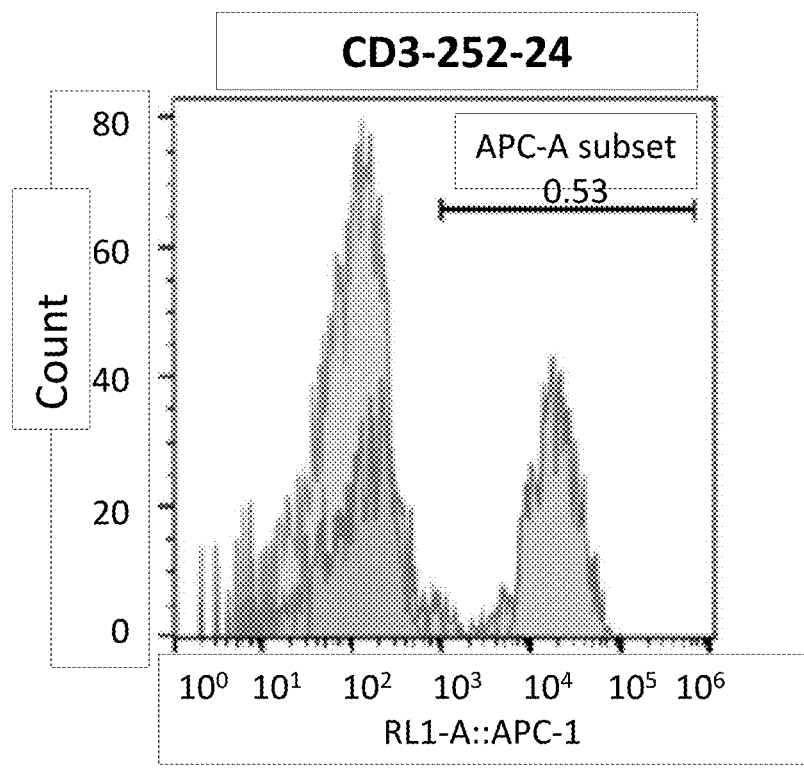
Figure 13G:
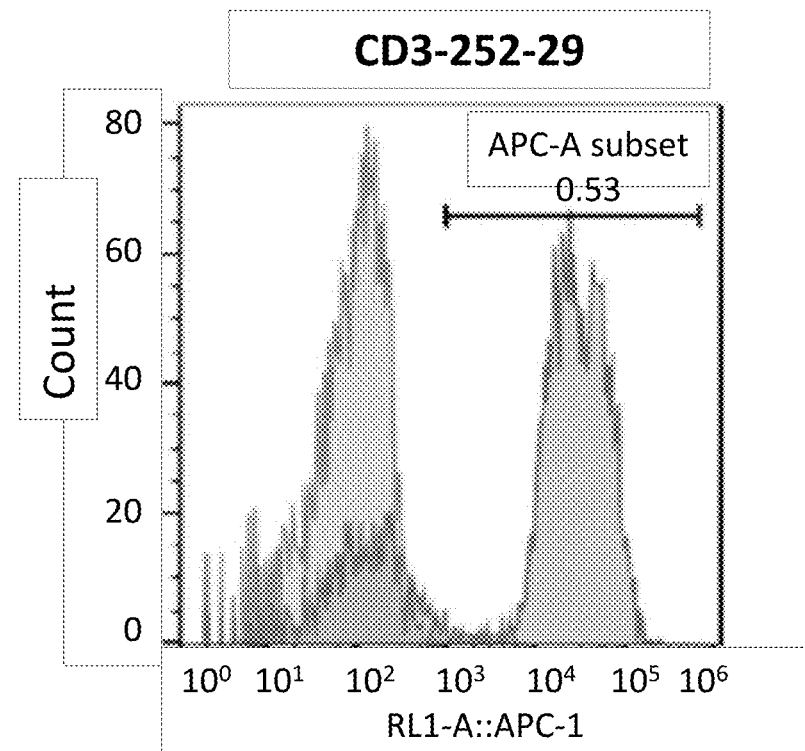
Figure 13H:
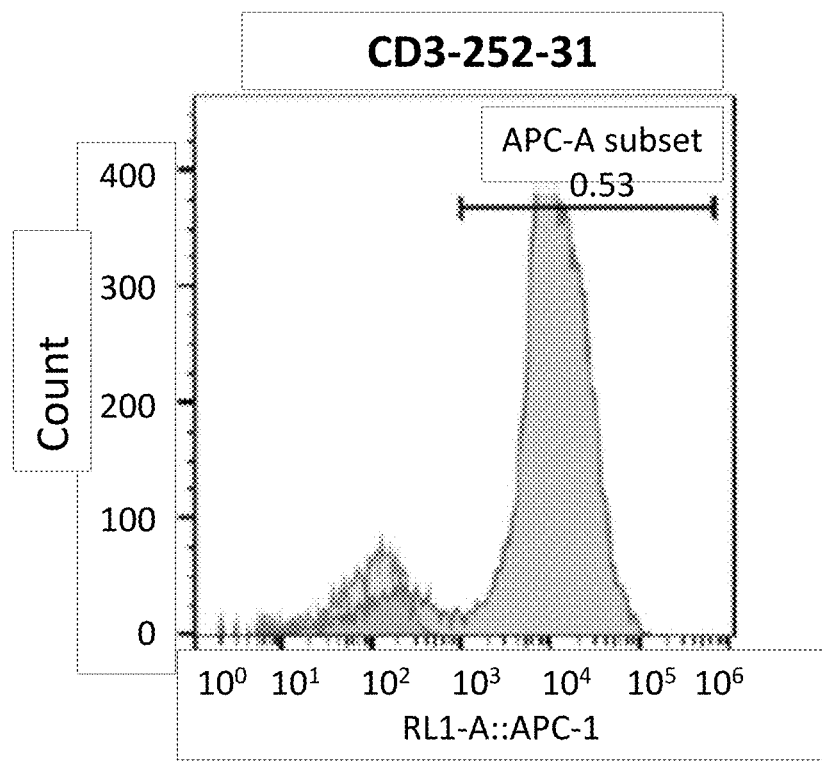

After various rounds of selection, CD3 epsilon (CD3ε) IgGs were analyzed. Data is seen in FIGS. 11A-11L and Tables 7-8. FIGS. 11A-11F show ELISA data from Round 4 and Round 5. FIGS. 11G-11L show data of cross-reactivity of human CD3 epsilon and cyno CD3 epsilon immunoglobulins. CD3-138-6 and CD3-155-3 binding data to CD3 is seen in FIGS. 11M-11N. FIGS. 12A-12G show graphs of titration of human CD3 on CD8+, CD3+, and CD3− T cells.

TABLE 7

| Protein panning data | | | | | | |
|---|---|---|---|---|---|---|
| Round | Target | Antigen | Washes | KF Washes | Titer | KF Titer |
| 1 | hCD3/cCD3 | 100 pmol | 3 | — | 2.40E+06 | — |
| 2 | hCD3 | 50 pmol | 5 | 4 | 1.20E+08 | 1.80E+06 |
| 3 | cCD3 | 20 pmol | 7 | 4 | 8.00E+06 | 2.40E+07 |
| 4 | hCD3 | 10 pmol | 9 | 5 | 1.00E+07 | 2.10E+06 |
| 5 | cCD3 | 10 pmol | 12 | 7 | 1.50E+07 | 1.00E+08 |

TABLE 8

| Round | Target | Antigen | Washes | Output Titer |
|---|---|---|---|---|
| 1 | hCD3 | 5 ug | 4 | 9.00E+04 |
| 2 | cCD3 | 5 ug | 5 | 1.40E+05 |
| 3 | hCD3 | 2.5 ug | 6 | 3.00E+06 |
| 4 | cCD3 | 2.5 ug | 7 | 4.00E+06 |
| 5 | hCD3 | 2.5 ug | 8 | 2.20E+07 |

Nineteen non-identical hCD3 epsilon and cyno CD3 epsilon immunoglobulins were identified including five that are human/cyno CD3 epsilon cross-reactive immunoglobulins. One of the human/cyno CD3 epsilon cross-reactive antibody, CD3-56-05 binds to human and cyno CD3 epsilon with 67 and 107 nM affinity, respectively.

Figure 14:
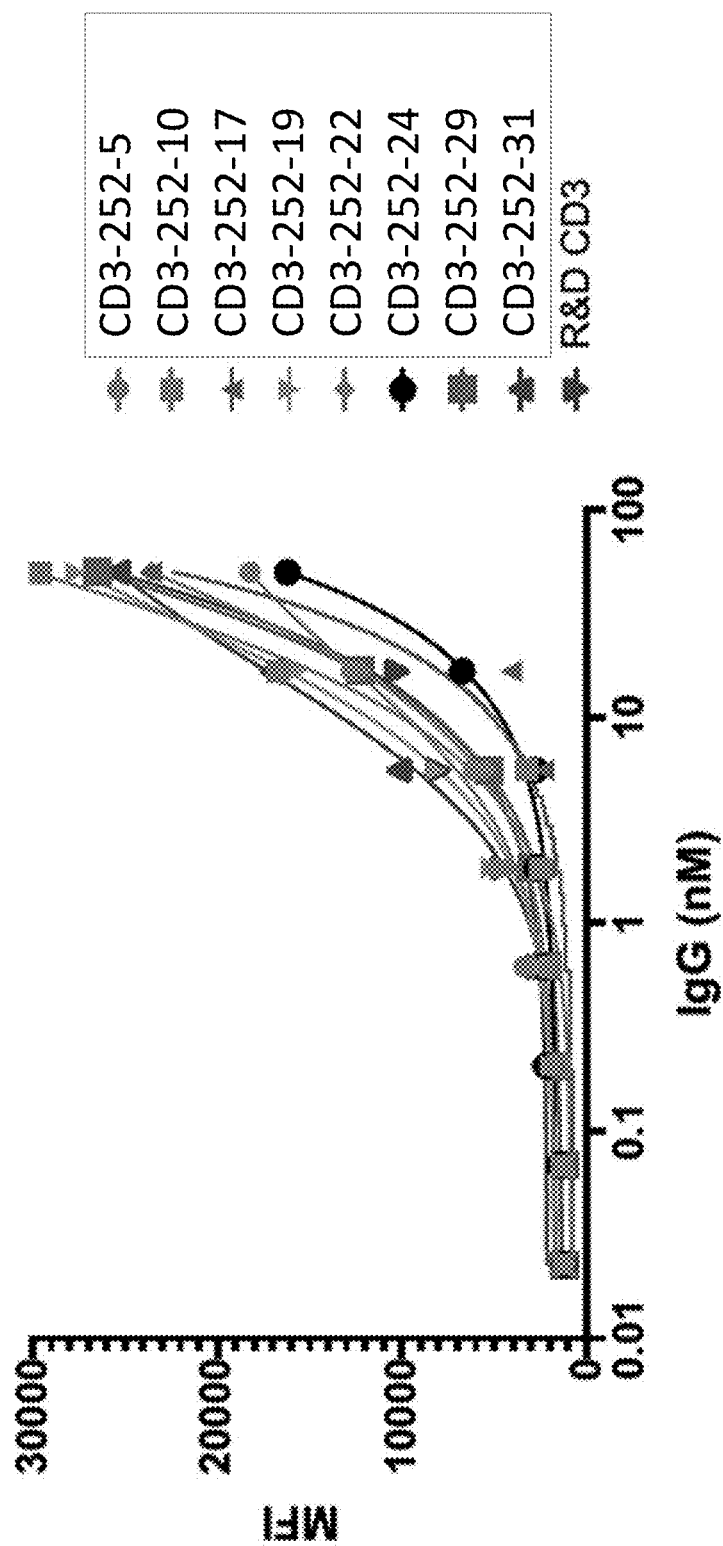
FIG. 14 depicts a graph of titration data for CD3-252-5, CD3-252-10-CD3-252-17, CD3-252-19, CD3-252-22, CD3-252-24, CD3-252-29, and CD3-252-31.

Addition, CD3 variant antibodies were identified from the VHH hShuffle and VHH hShuffle hyperimmune library. Data for CD3-252-5, CD3-252-10, CD3-252-7, CD3-252-19, CD3-252-22, CD3-252-24. CD3-252-29, and CD3-252-31 are seen in FIGS. 13A-13H. Top CD3 variant antibodies included CD3-252-10, CD3-252-19, CD3-252-22. CD3-252-29, and CD3-252-31. Titration data is seen in FIG. 14.

Example 6. Cytotoxicity Studies

Figure 15A:
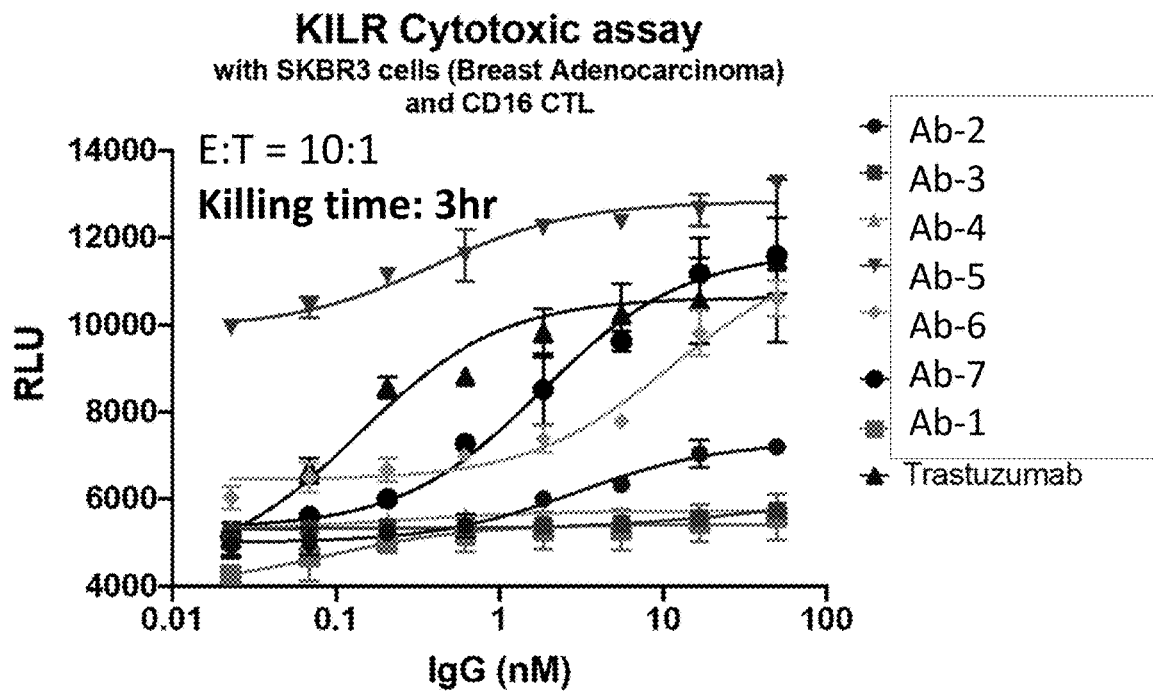
FIGS. 15A-15B depict cytotoxicity assay data from CD16 CTL cells at 3 hour killing time (FIG. 15A) and at 20 hours (FIG. 15B).
Figure 15B:
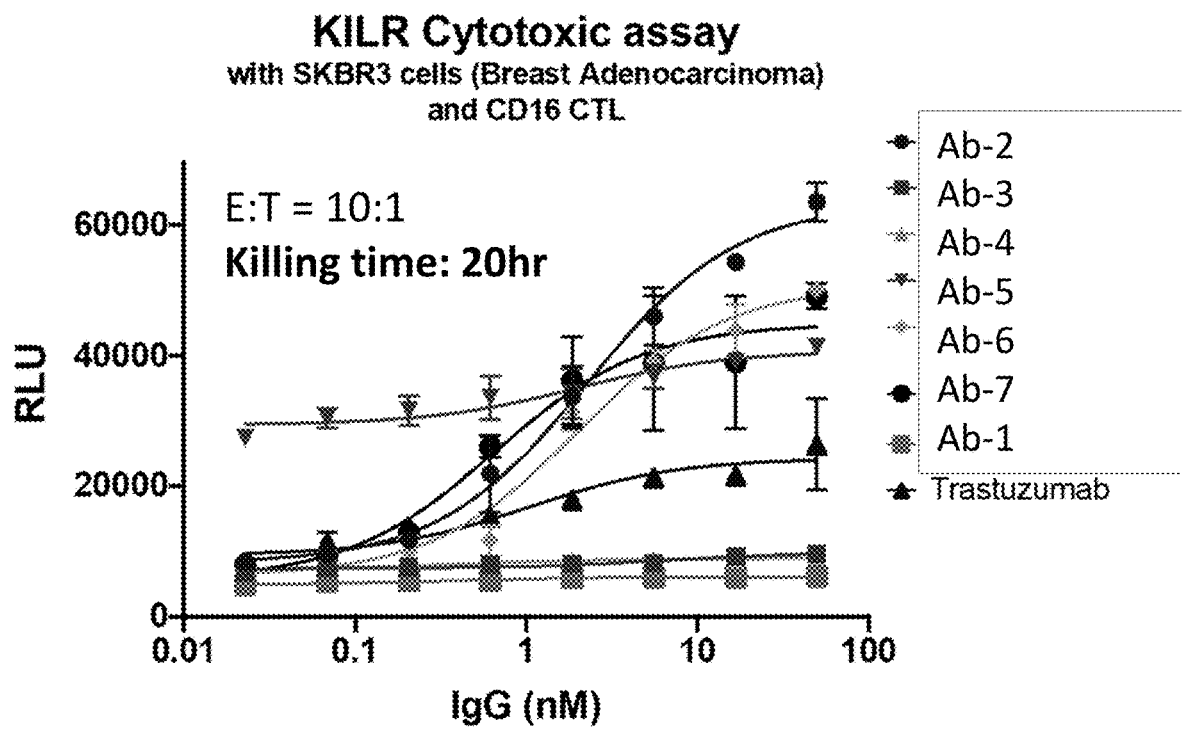
Figure 16A:
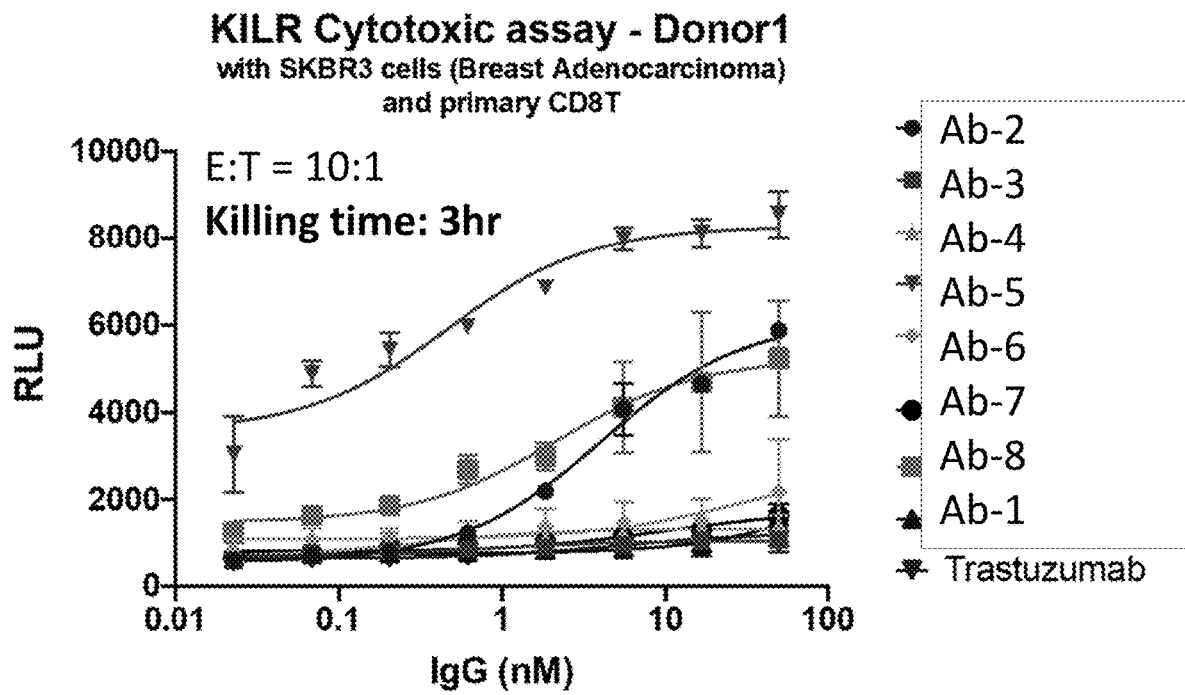
FIGS. 16A-16B depict cytotoxicity assay data from primary CD8 T cells at 3 hour killing time (FIG. 16A) and at 20 hours (FIG. 16B).
Figure 16B:
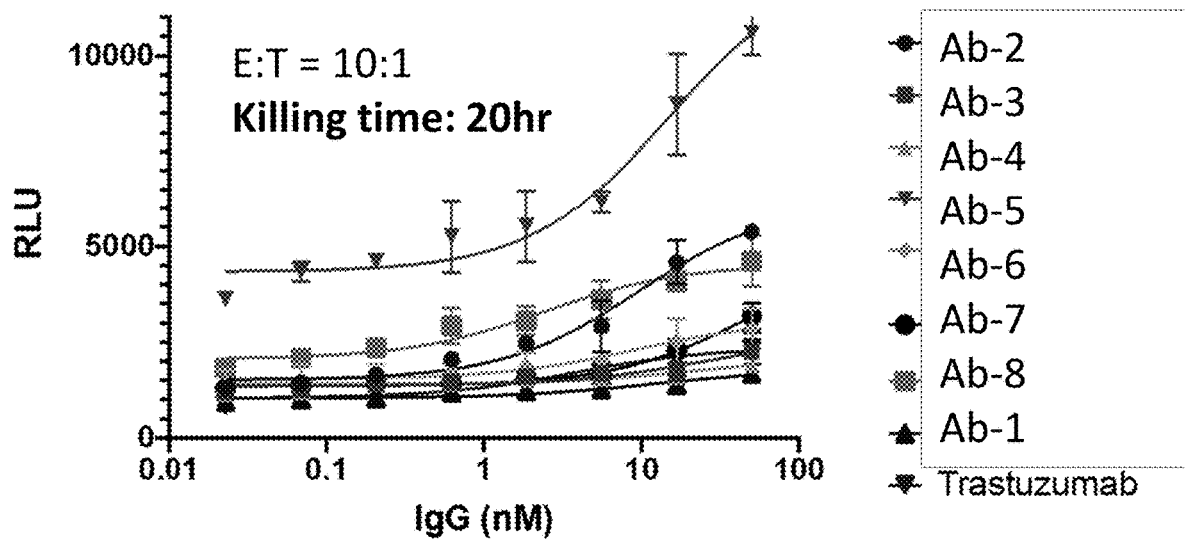
Figure 17A:
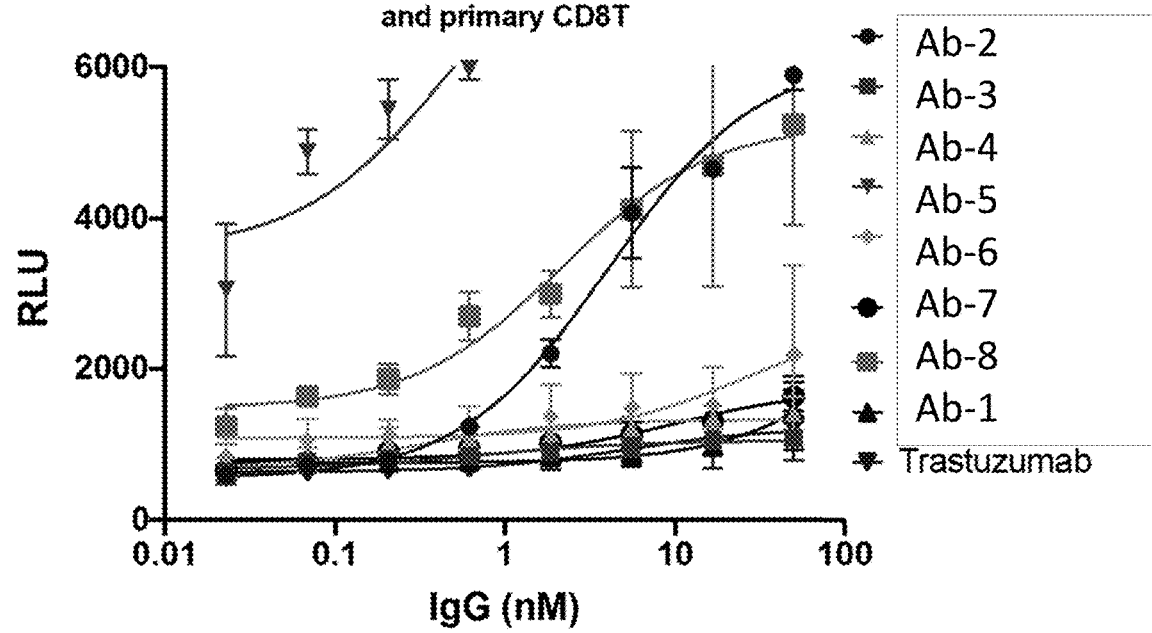
FIGS. 17A-17B depict enlarge versions of FIGS. 16A-16B.
Figure 17B:
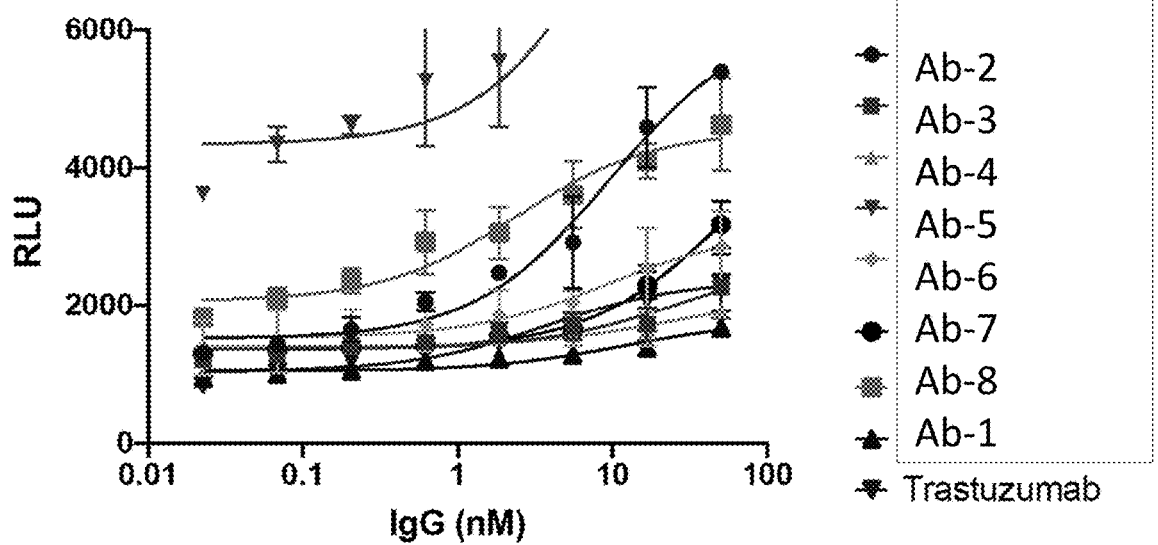

Variant CD3-ERBB bispecific antibodies were tested in cytotoxic and binding assays.
The antibodies used include the following:
Negative control (hIgG1mt)
Ab-1 (scfv): Transtu(erbb)+CD-3-56-5
Form1: (knob)
Ab-2: Transtu(erbb)+SP34(CD3)
Ab-3: Transtu(erbb)+CD3-138-6
Ab-4: Transtu(erbb)+CD3-155-3
Form2: (scfv)
Ab-5: Transtu(erbb)+SP34(CD3)
Ab-6: Transtu(erbb)+CD3-138-6
Ab-7: Transtu(erbb)+CD-3-155-3
Ab-8: Trastuzumah+CD3(TR66) BiTE control KILR® Cytotoxicity assays were performed according to manufacturer's instructions (Eurofins, DiscoverX). For the assays, the E:T ratio used for CD16 CTL cells was 10:1 and for PBMCs was 25:1. Cytotoxicity assay data from CD16 CTL cells is seen in FIG. 15A at 3 hour killing time and in FIG. 15B at 20 hours. Cytotoxicity assay data from primary CD8 T cells is seen in FIG. 16A at 3 hour killing time and in FIG. 16B at 20 hours. Enlarged versions of data from FIGS. 16A-16B is seen in FIGS. 17A-17B.

Figure 18:
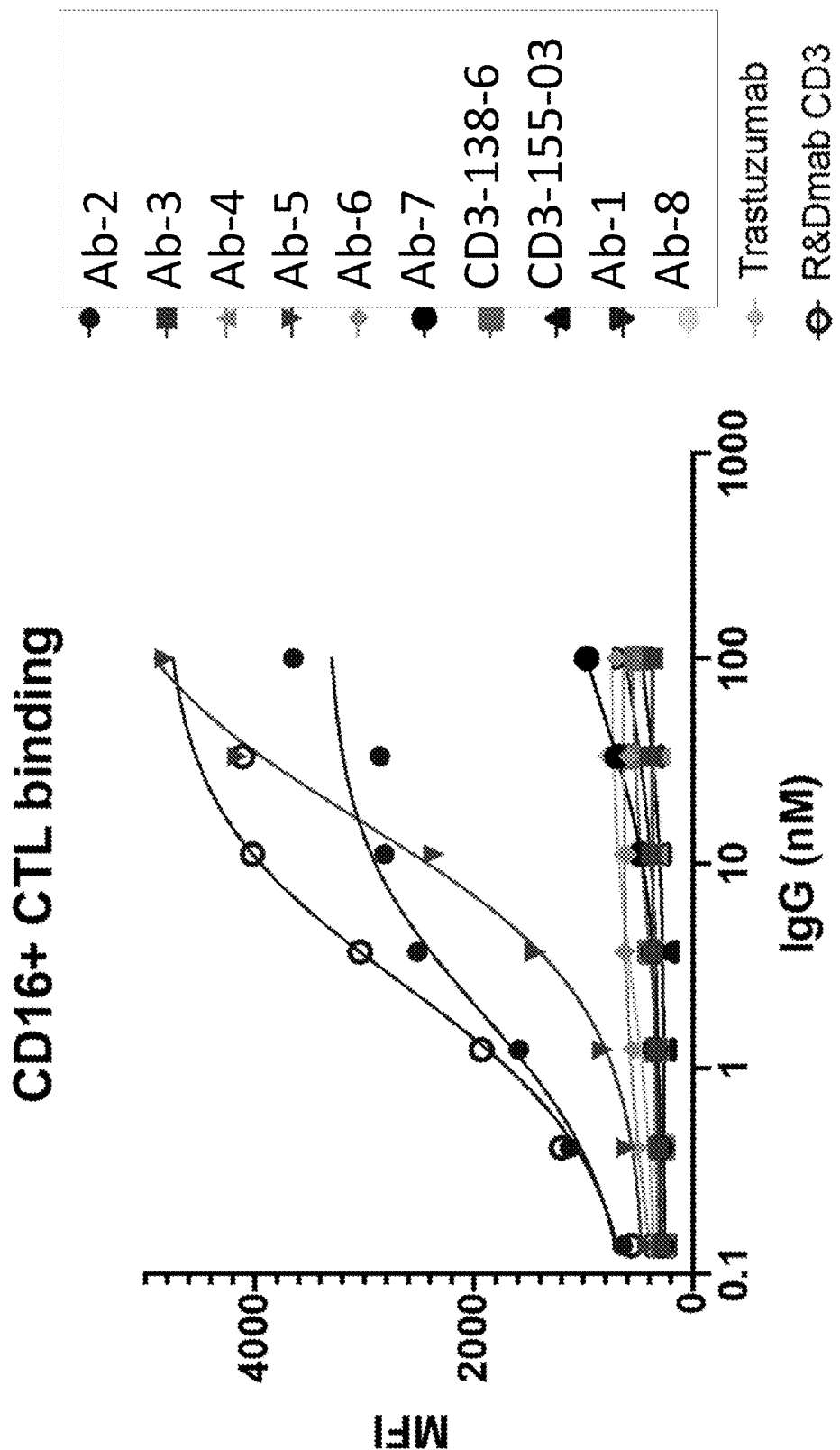
FIG. 18 depicts an assay of CD16+ CTL binding assays for CD3-ERBB bispecific antibodies.
Figure 19A:
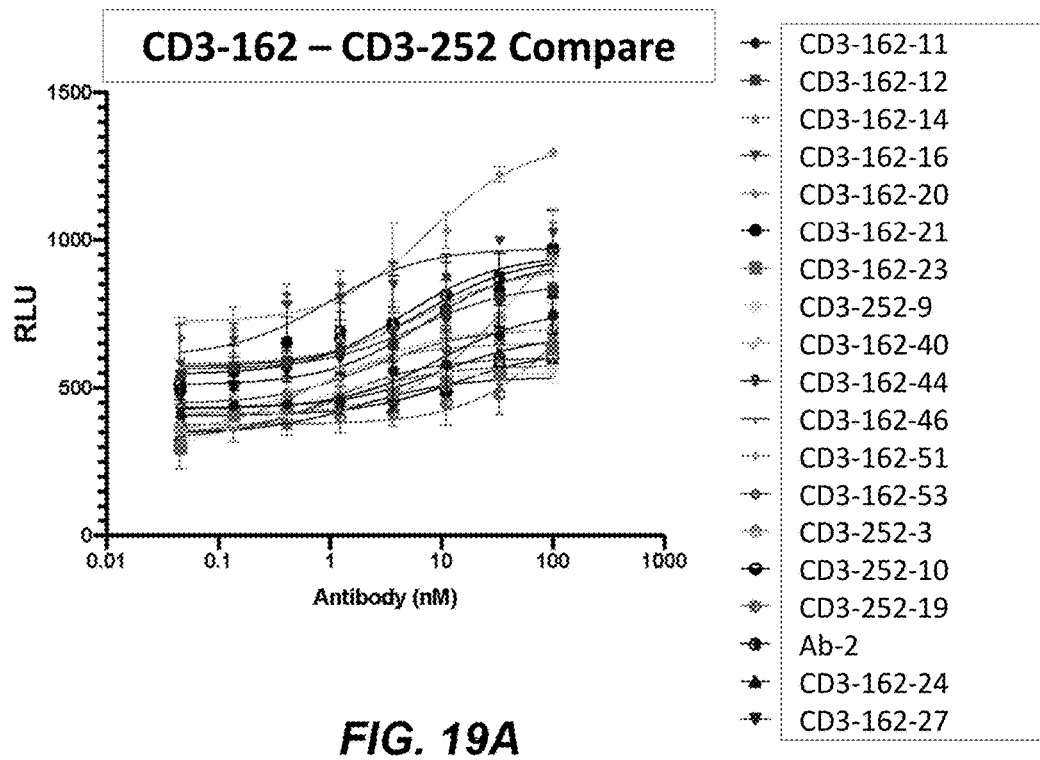
FIGS. 19A-19D depict a comparison of cytotoxic assays.
Figure 19B:
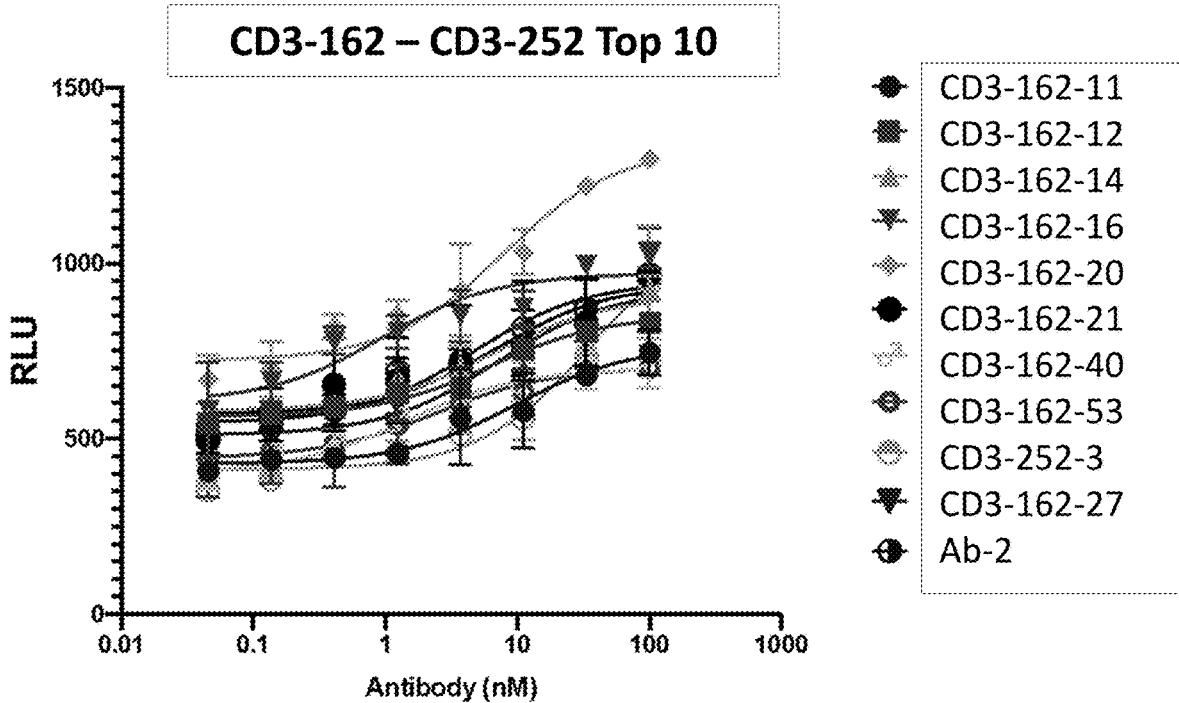
Figure 19C:
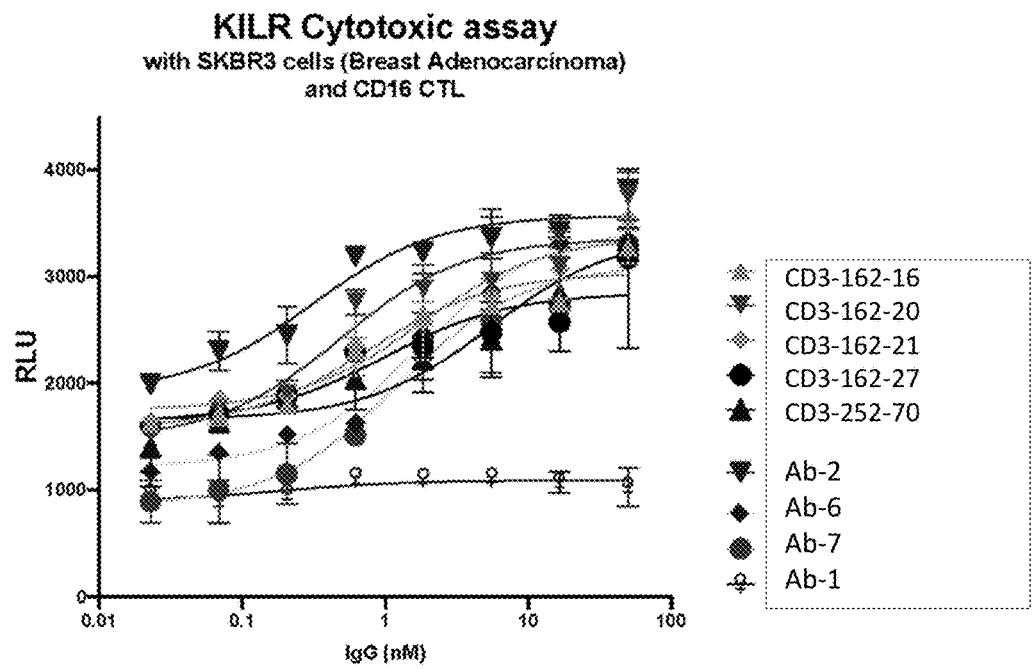
Figure 19D:
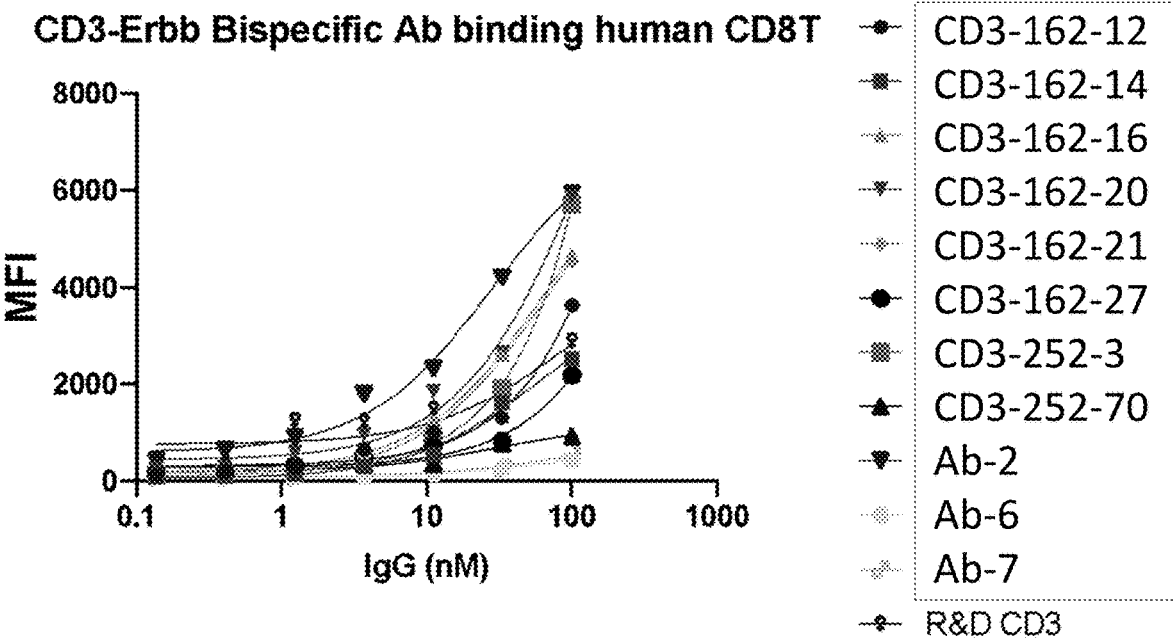
Figure 20A:
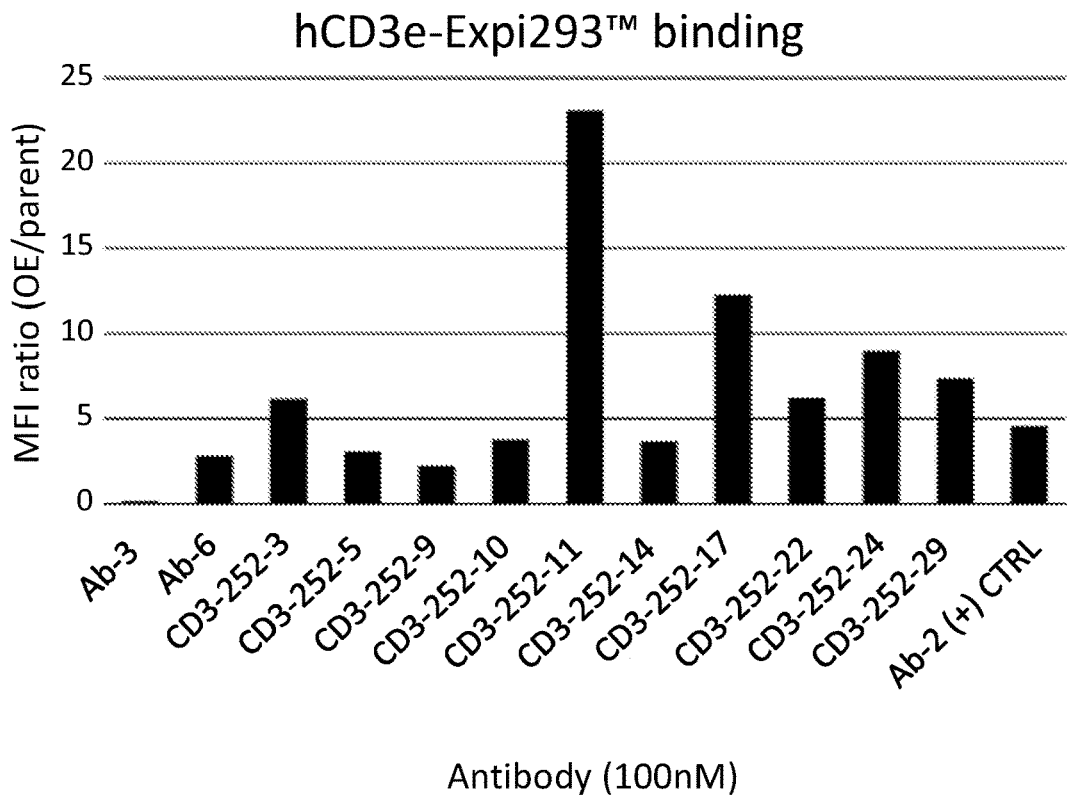
FIGS. 20A-20B depicts overexpressed human (FIG. 20A) and cynomolgus monkey (cyno) (FIG. 20B) Expi293™ cell binding.
Figure 20B:
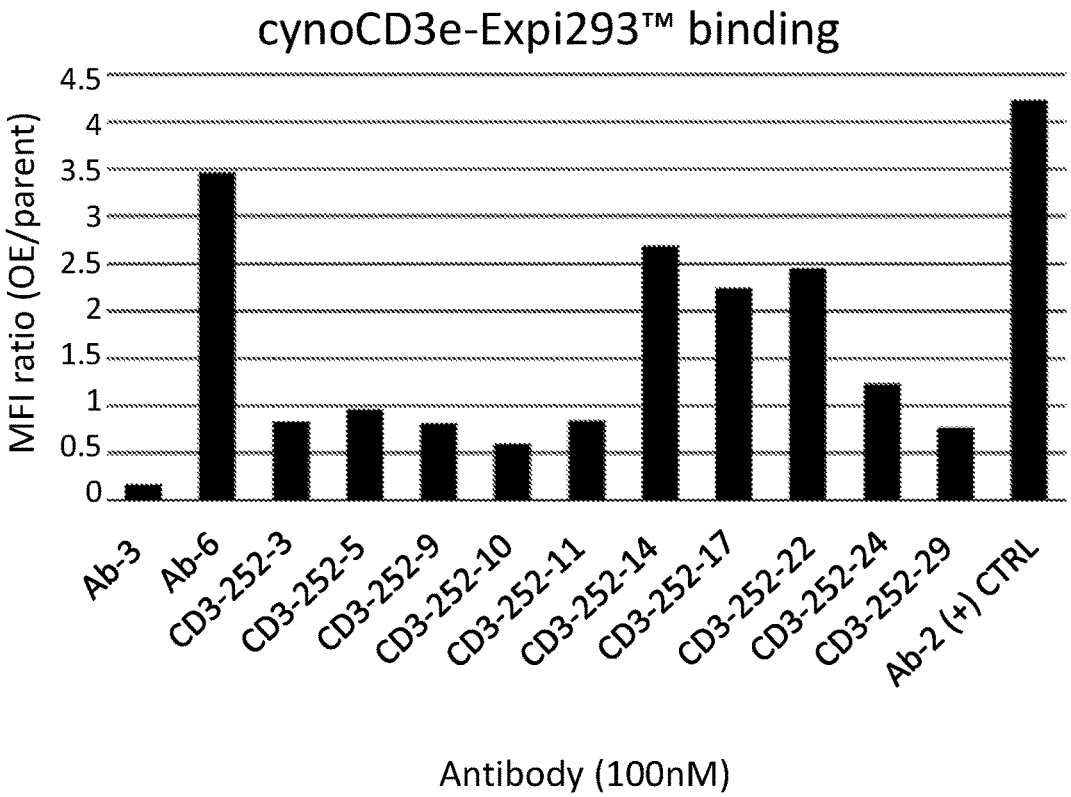
Figure 21A:
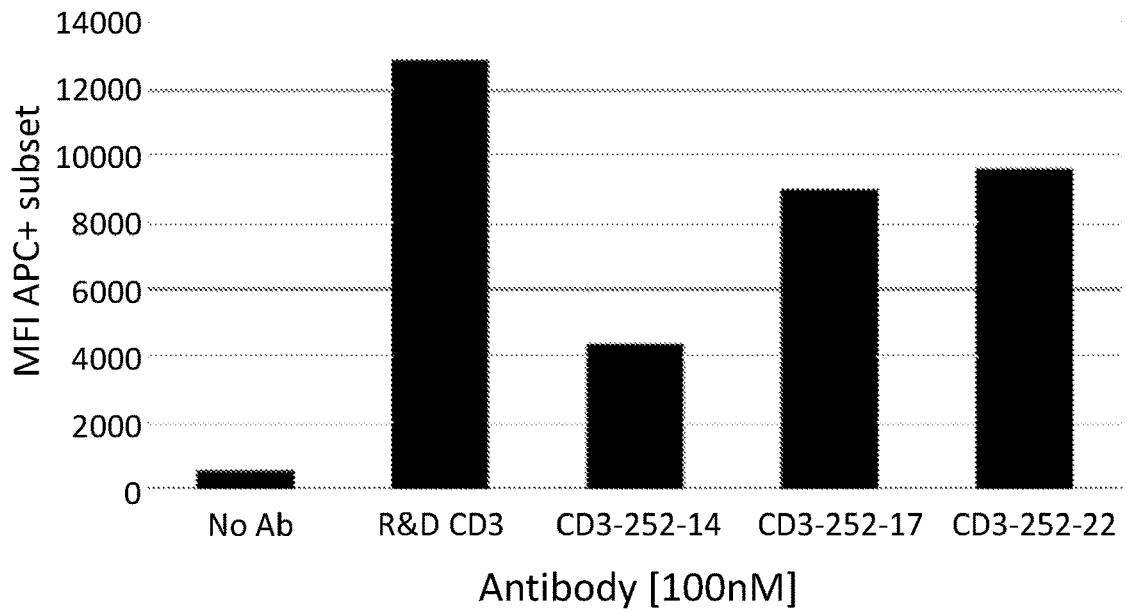
FIGS. 21A-21C depict monospecific cell binding of Ab binding primary CD8 T cells (FIG. 21A), hCD3e-Expi 293™ binding (FIG. 21B), and cynoCD3e-Expi293™ binding (FIG. 21C).
Figure 21B:
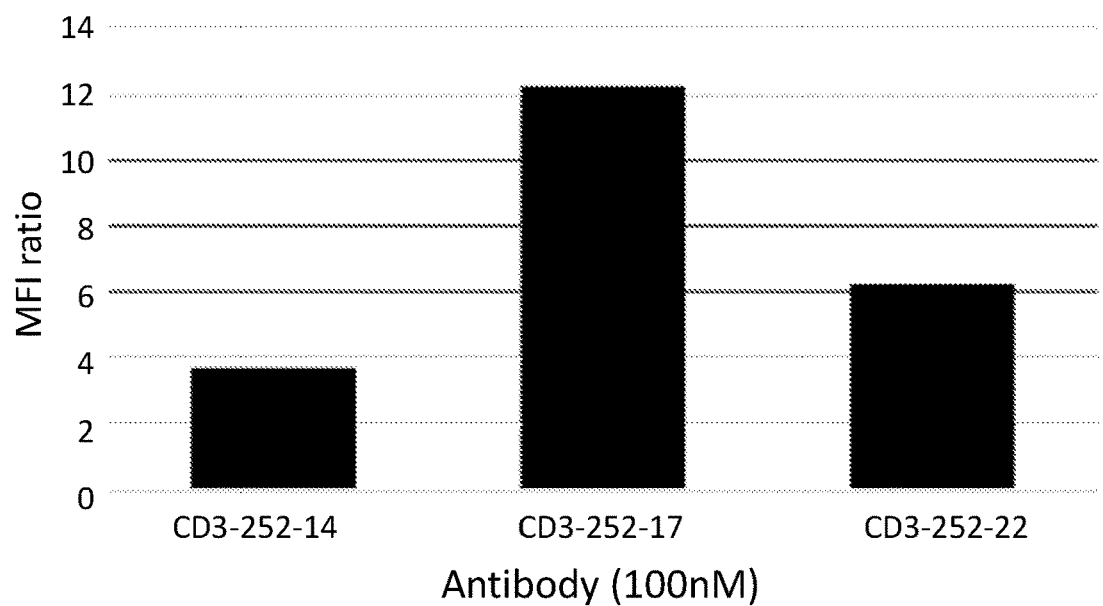
Figure 21C:
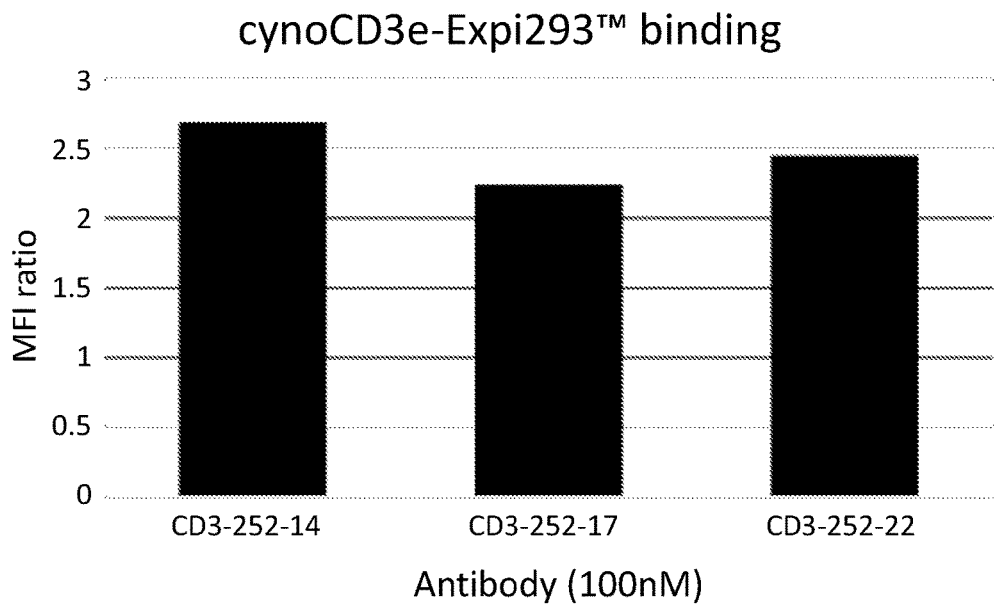
Figure 22A:
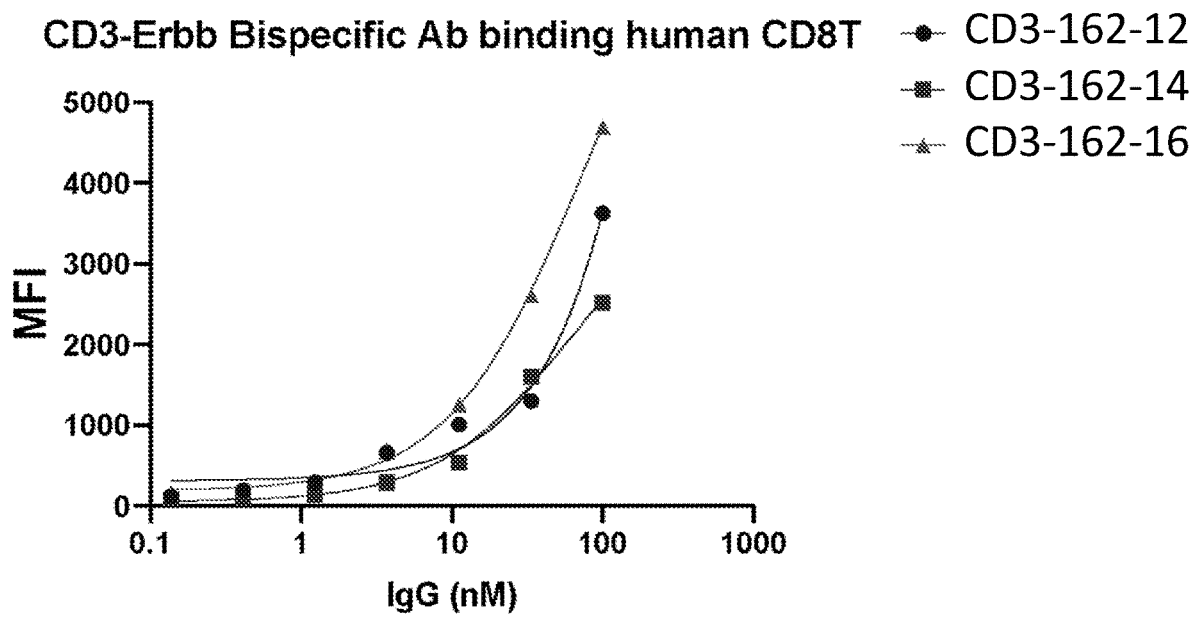
FIGS. 22A-22B depict bispecific cell binding in human (FIG. 22A) and cynomolgus monkey (FIG. 22B) samples.
Figure 22B:
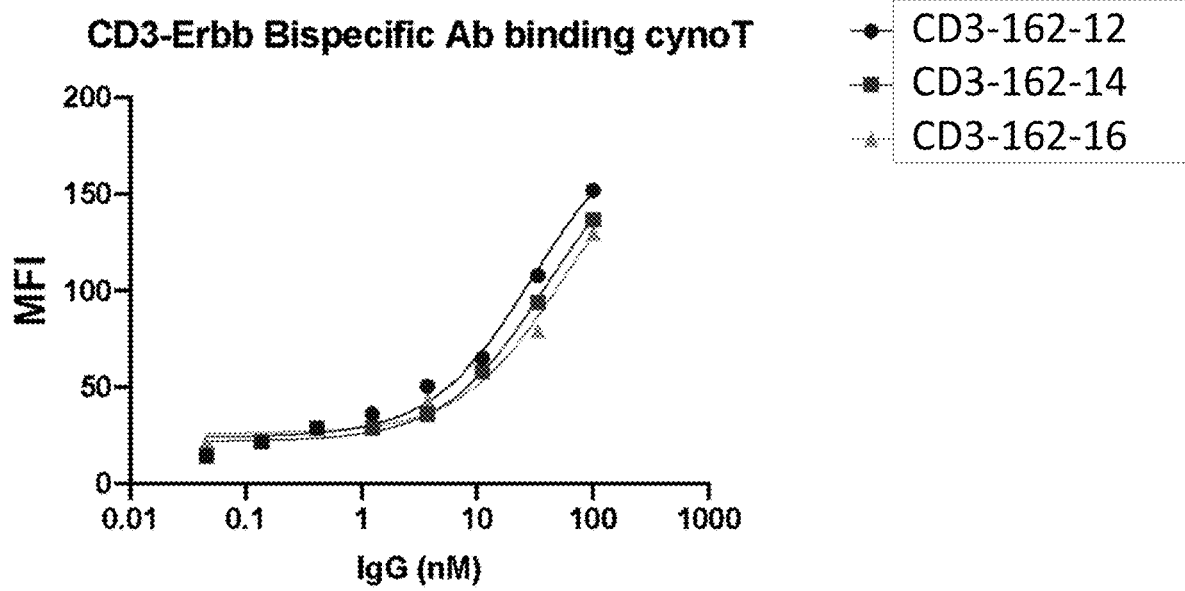
Figure 23:
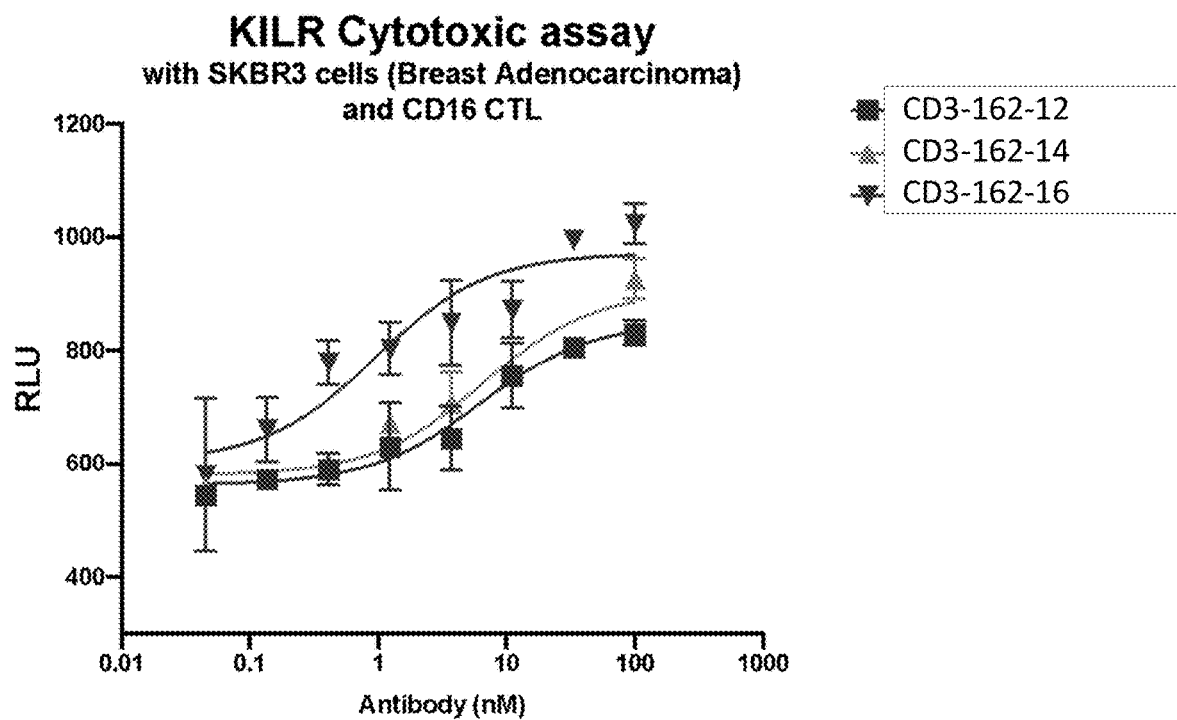
FIG. 23 depicts results from cytotoxic assays with SKBR3 cells (breast adenocarcinoma) and CD16 cytotoxic T lymphocytes.
Figure 24A:
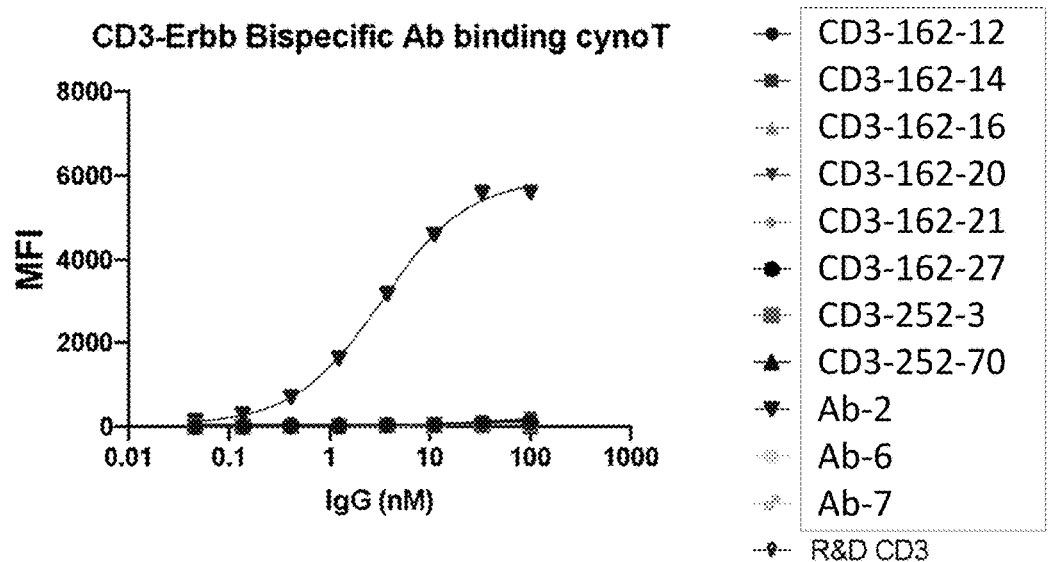
FIGS. 24A-24B depict the cell killing activity of top clones.
Figure 24B:
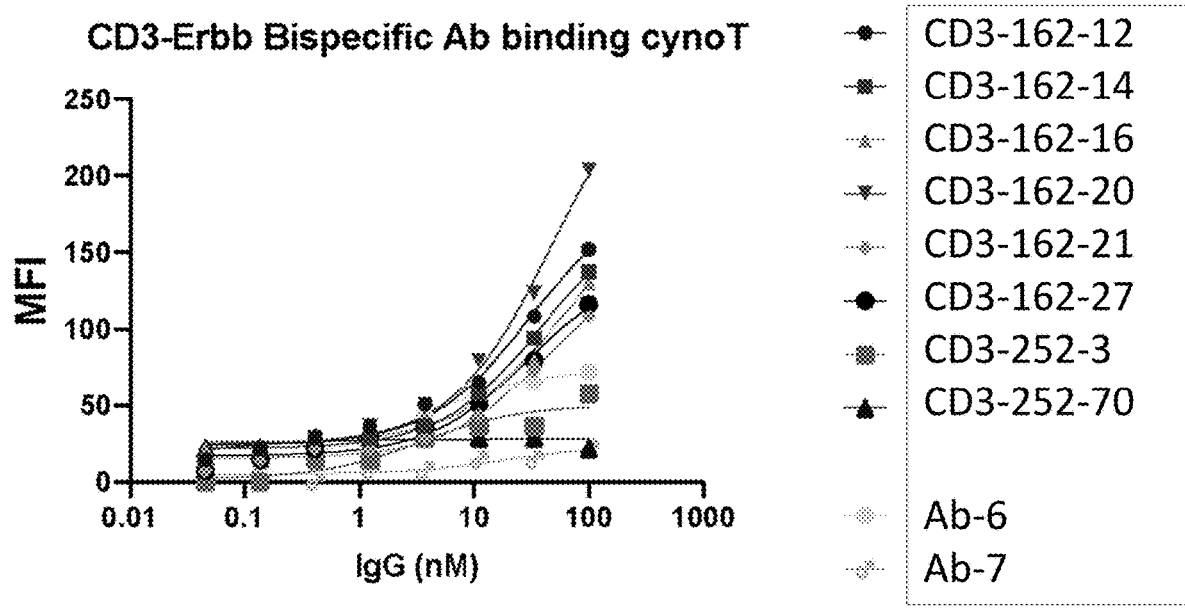

Variant CD3-ERBB bispecific antibodies were also assayed in CD16+ CTL binding assays. Data is seen in FIG. 18.

Based on the data, Ab-2, Ab-5, Ab-6, Ab-7, and AB-8 exhibited improved cytotoxicity. Ab-2, Ab-5, Ab-6, and Ab-7 also exhibited improved binding.

Example 7. Exemplary Sequences

Sequences for hCD3 epsilon and cCD3 epsilon immunoglobulins are seen in Table 9.

TABLE 9

CD3 epsilon sequences

| SEQ ID NO: | IgG | Amino Acid Sequence |
|---|---|---|
| | | Variable Heavy Chain CDR1 (CDRH1) |
| 1 | CD3-138-6 | GYTFTSNMH |
| 2 | CD3-56-5 | FTFSSYAMN |
| 3 | CD3-155-03 | FTFSSYAIN |
| | | Variable Heavy Chain CDR2 (CDRH2) |
| 4 | CD3-138-6 | VASISSYYGYTYYA |
| 5 | CD3-56-5 | VSAVSGSGGRTYYA |
| 6 | CD3-155-03 | VSALSGSGGSTYYA |
| | | Variable Heavy Chain CDR3 (CDRH3) |
| 7 | CD3-138-6 | GGNYYNLWTGYYPLAY |
| 8 | CD3-56-5 | ARERATTLDY |
| 9 | CD3-155-03 | ARRSAQLGDY |
| 10 | CD3-56-5A | CARERATTLDYW |
| 11 | CD3-56-11 | CARDSLTTRGYYYYMDVW |
| | | Variable Light Chain CDR1 (CDRL1) |
| 12 | CD3-138-6 | RASQDISTYLN |
| 13 | CD3-56-5 | RASQTIYSHLN |
| 14 | CD3-155-03 | RASQSISSFLN |

TABLE 9-continued

CD3 epsilon sequences

| SEQ ID NO: | IgG | Amino Acid Sequence |
|---|---|---|
| | | Variable Light Chain CDR2 (CDRL2) |
| 15 | CD3-138-6 | YTDRLQT |
| 16 | CD3-56-5 | VASRLQS |
| 17 | CD3-155-03 | AAPSLQS |
| | | Variable Light Chain CDR3 (CDRL3) |
| 18 | CD3-138-6 | QQGGALPFT |
| 19 | CD3-56-5 | QQSFSTSWT |
| 20 | CD3-155-03 | QQSFRTPFT |
| | | Variable Heavy Chain |
| 21 | CD3-56-5 | EVQLLESGGGLVQPGGSLRLSCAASGFTFSSYAMNWVRQAPGKGLEWVSAVSGSGGRTYYADSVKGRFTISRDNSKNTLYLQMNSLRAEDTAVYYCARERATTLDYWGQGTLVTVSS |
| 22 | CD3-56-11 | EVQLLESGGGLVQPGGSLRLSCAASGFRFSTYAMNWVRQAPGKGLEWVSGISGSGGSKYRADSVKGRFTISRDNSKNTLYLQMNSLRAEDTAVYYCARDSLTTRGYYYYMDVWGQGTLVTVSS |
| 23 | CD3-138-6 | EVQLLESGGGLVQPGGSLRLSCAASGGYTFTSNMHWVRQAPGKGLEWVASISSYYGYTYYADSVKGRFTISRDNSKNTLYLQMNSLRAEDTAVYYCGGNYYNLWTGYYPLAYWGQGTLVTVSS |
| 24 | CD3-155-9 | EVQLLESGGGLVQPGGSLRLSCAASGFTFSNYALNWVRQAPGKGLEWVSAVTGSGGSTYYADSVKGRFTISRDNSKNTLYLQMNSLRAEDTAVYYCARVRATTLDYWGQGTLVTVSS |
| 25 | CD3-252-005 | EVQLVESGGGLVQPGGSLRLSCAASGRISNINIMGWFRQAPGKEREFVAAISWNSGTTRYADSVKGRFTISADNSKNTAYLQMNSLKPEDTAVYYCASQGPGLYGSGSYLRYWGQGTLVTVSS |
| 26 | CD3-252-010 | EVQLVESGGGLVQPGGSLRLSCAASGRSLYDRAYVMGWFRQAPGKEREFVAAINRSGSALYADSVKGRFTISADNSKNTAYLQMNSLKPEDTAVYYCAAKAVTSRDHEWGQGTLVTVSS |
| 27 | CD3-252-017 | EVQLVESGGGLVQPGGSLRLSCAASVDIFTRNIMGWFRQAPGKEREFVAAIRSSDGTTYYADSVKGRFTISADNSKNTAYLQMNSLKPEDTAVYYCAKRAGRGYSYGYVDYWGQGTLVTVSS |
| 28 | CD3-252-019 | EVQLVESGGGLVQPGGSLRLSCAASGRTFSNNVMGWFRQAPGKEREFVAAISSSATTLYADSVKGRFTISADNSKNTAYLQMNSLKPEDTAVYYCAQKDTALKVWGQGTLVTVSS |
| 29 | CD3-252-022 | EVQLVESGGGLVQPGGSLRLSCAASGNIFTRHIMGWFRQAPGKEREFVAAITNGGSTKYADSVKGRFTISADNSKNTAYLQMNSLKPEDTAVYYCARQDYYDSSGHIRYWGQGTLVTVSS |
| 30 | CD3-252-024 | EVQLVESGGGLVQPGGSLRLSCAASGITFKRYVMGWFRQAPGKEREFVAAITNGGSTKYADSVKGRFTISADNSKNTAYLQMNSLKPEDTAVYYCARDLSAGPGKAVYWGQGTLVTVSS |
| 31 | CD3-252-029 | EVQLVESGGGLVQPGGSLRLSCAASGTTFRINVMGWFRQAPGKEREFVAAITSSGSSTLYADSVKGRFTISADNSKNTAYLQMNSLKPEDTAVYYCARGGGYHRLWGQGTLVTVSS |
| 32 | CD3-252-031 | EVQLVESGGGLVQPGGSLRLSCAASGSAFSSTVMGWFRQAPGKEREFVAAINNFGTTKYADSVKGRFTISADNSKNTAYLQMNSLKPEDTAVYYCAHRVRHYGDWEGGALDVWGQGTLVTVSS |
| | | Varitable Light Chain |
| 33 | CD3-56-5 | DIQMTQSPSSLSASVGDRVITICRASQTIYSHLNWYQQKPGKAPKLLIYVASRLQSGVPSRFSGSGSGTDFTLTISSLQPEDFATYYCQQSFSTSWTFGGGTKVEIK |
| 34 | CD3-56-11 | DIQMTQSQSSLSASVGDRVTITCRASQSIRTSLNWYQQPGKAPKLLIYAASRLQSGVPSRFSGSGSGTDFTLTISSLQPEDFATYYCQQSYSTLYSFGGGTKVEIK |

TABLE 9-continued

CD3 epsilon sequences

| SEQ ID NO: | IgG | Amino Acid Sequence |
|---|---|---|
| 35 | CD3-138-6 | DIQMTQSPSSLSASVGDRVTITCRASQDISTYLNWYQQKPGKAPKLLIYYTDRLQT GVPSRFSGSGSGTDFTLTISSLQPEDFATYYCQQGGALPFTFGQGTKVEIK |
| 36 | CD3-155-9 | DIQMTQSPSSLSASVGDRVTITCRTSQSISTYLNWYQQKPGKAPKLLIYTASRLQS GVPSRFSGSGSGTDFTLTISSLQPEDFATYYCQQSYSTPWTFGGGTKVEIK |

Antibody Sequence

| 37 | Ab-2 | MEWSWVFLFFLSVTTGVHSEVQLVESGGGLVQPGGSLKLSCAASGFTFN KYAMNWVRQAPGKGLEWVARIRSKYNNYATYYADSVKDRFTISRDDSK NTAYLQMNNLKTEDTAVYYCVRHGNFGNSYISYWAYWGQGTLVTVSS GGGGSGGGGSGGGGSQTVVTQEPSLTVSPGGTVTLTCGSSTGAVTSGNY PNWVQQKPGQAPRGLIGGTKFLAPGTPARFSGSLLGGKAALTLSGVQPED EAEYYCVLWYSNRWVFGGGTKLFVLGGGGSGGGGSEPKSSDKTHTCPP CPAPEAAGGPSVFLFPPKPKDTLMISRTPEVTCVVVDVSHEDPEVKFNWY VDGVEVHNAKTKPREEQYNSTYRVVSVLTVLHQDWLNGKEYKCKVSN KALPAPIEKTISKAKGQPREPQVYTLPPSREEMTKNQVSLSCAVKGFYPSD IAVEWESNGQPENNYKTTPPVLDSDGSFFLVSKLTVDKSRWQQGNVFSCS VMHEALHNRYTQKSLSLSPG |
| 38 | Ab-3 | EVQLLESGGGLVQPGGSLRLSCAASGGYTFTSNMHWVRQAPGKGLEWV ASISSYYGYTYYADSVKGRFTISRDNSKNTLYLQMNSLRAEDTAVYYCG GNYYNLWTGYYPLAYWGQGTLVTVSSGGGGSGGGGSGGGGSDIQMTQ SPSSLSASVGDRVTITCRASQDISTYLNWYQQKPGKAPKLLIYYTDRLQTG VPSRFSGSGSGTDFTLTISSLQPEDFATYYCQQGGALPFTFGQGTKVEIKG GGGSGGGGSEPKSSDKTHTCPPCPAPEAAGGPSVFLFPPKPKDTLMISRTP EVTCVVVDVSHEDPEVKFNWYVDGVEVHNAKTKPREEQYNSTYRVVSV LTVLHQDWLNGKEYKCKVSNKALPAPIEKTISKAKGQPREPQVYTLPPSR EEMTKNQVSLSCAVKGFYPSDIAVEWESNGQPENNYKTTPPVLDSDGSFF LVSKLTVDKSRWQQGNVFSCSVMHEALHNRYTQKSLSLSPG |

Additional VHH

| 39 | CD3-162-12 | EVQLVESGGGLVQPGGSLRLSCAASGISISTKVMGWFRQAPGKEREFVAA ITWSGGSTKYADSVKGRFTISADNSKNTAYLQMNSLKPEDTAVYYCAGR FARGRYYGMDVWGQGTLVTVSS |
| 40 | CD3-162-14 | EVQLVESGGGLVQPGGSLRLSCAASVDIFTRNIMGWFRQAPGKEREFVA AIRSSDGTTYYADSVKGRFTISADNSKNTAYLQMNSLKPEDTAVYYCAK RAGRGYSYGYVDYWGQGTLVTVSS |
| 41 | CD3-162-16 | EVQLVESGGGLVQPGGSLRLSCAASGNIFTRHIMGWFRQAPGKEREFVA AITNGGSTKYADSVKGRFTISADNSKNTAYLQMNSLKPEDTAVYYCARQ DYYDSSGHIRYWGQGTLVTVSS |

Additional Single-Chain Variable Fragments

| 42 | CD3-162-12 | EVQLVESGGGLVQPGGSLRLSCAASGFNIKDTYIHAVRQAPGKGLEWVA RIYPTNGYTRYADSVKGRFTISADTSKNTAYLQMNSLRAEDTAVYYCSR WGGDGFYAMDYWGQGTLVTVSSGGGGSGGGGSGGGGSGGGGSDIQMT QSPSSLSASVGDRVTITCRASQDVNTAVAWYQQKPGKAPKLLIYSASFLY SGVPSRFSGSRSGTDFTLTISSLQPEDFATYYCQQHYTTPPTFGQGTKVEIK EPKSSDKTHTCPPCPAPEAAGGPSVFLFPPKPKDTLMISRTPEVTCVVVDV SHEDPEVKFNWYVDGVEVHNAKTKPREEQYNSTYRVVSVLTVLHQDWL NGKEYKCKVSNKALPAPIEKTISKAKGQPREPQVYTLPPSREEMTKNQVS LTCLVKGFYPSDIAVEWESNGQPENNYKTTPPVLDSDGSFFLYSKLTVDK SRWQQGNVFSCSVMHEALHNHYTQKSLSLSPGGGGGSGGGGSGGGGSE VQLVESGGGLVQPGGSLRLSCAASGISISTKVMGWFRQAPGKEREFVAAI TWSGGSTKYADSVKGRFTISADNSKNTAYLQMNSLKPEDTAVYYCAGRF ARGRYYGMDVWGQGTLVTVSS |
| 43 | CD3-162-14 | EVQLVESGGGLVQPGGSLRLSCAASGFNIKDTYIHWVRQAPGKGLEWVA RIYPTNGYTRYADSVKGRFRISADTSKNTAYLQMNSLRAEDTAVYYCSR WGGDGFYAMDYWGQGTLVTVSSGGGGSGGGGSGGGGSGGGGSDIQMT QSPSSLSASVGDRVTITCRASQDVNTAVAWYQQKPGKAPKLLIYSASFLY SGVPSRFSGSRSGTDFTLTISSLQPEDFATYYCQQHYTTPPTFGQGTKVEIK EPKSSDKTHTCPPCPAPEAAGGPSVFLFPPKPKDTLMISRTPEVTCVVVDV SHEDPEVKFNWYVDGVEVHNAKTKPREEQYNSTYRVVSVLTVLHQDWL NGKEYKCKVSNKALPAPIEKTISKAKGQPREPQVYTLPPSREEMTKNQVS LTCLVKGFYPSDIAVEWESNGQPENNYKTTPPVLDSDGSFFLYSKLTVDK SRWQQGNVFSCSVMHEALHNHYTQKSLSLSPGGGGGSGGGGSGGGGSE VQLVESGGGLVQPGGSLRLSCAASVDIFTRNIMGWFRQAPGKEREFVAAI RSSDGTTYYADSVKGRFTISADNSKNTAYLQMNSLKPEDTAVYYCAKRA GRGYSYGYVDYWGQGTLVTVSS |

TABLE 9-continued

CD3 epsilon sequences

| SEQ ID NO: | IgG | Amino Acid Sequence |
|---|---|---|
| 44 | CD3-162-16 | EVQLVESGGGLVQPGGSLRLSCAASGFNIKDTYIHWVRQAPGKGLEWVA RIYPTNGYTRYADSVKGRFRISADTSKNTAYLQMNSLRAEDTAVYYCSR WGGDGFYAMDYWGQGTLVTVSSGGGGSGGGGSGGGGSGGGGSDIQMT QSPSSLSASVGDRVTITCRASQDVNTAVAWYQQKPGKAPKLLIYSASFLY SGVPSRFSGSRSGTDFTLTISSLQPEDFATYYCQQHYTTPPTFGQGTKVEIK EPKSSDKTHTCPPCPAPEAAGGPSVFLFPPKPKDTLMISRTPEVTCVVVDV SHEDPEVKFNWYVDGVEVHNAKTKPREEQYNSTYRVVSVLTVLHQDWL NGKEYKCKVSNKALPAPIEKTISKAKGQPREPQVYTLPPSREEMTKNQVS LTCLVKGFYPSDIAVEWESNGQPENNYKTTPPVLDSDGSFFLYSKLTVDK SRWQQGNVFSCSVMHEALHNHYTQKSLSLSPGGGGSGGGGSGGGGSE VQLVESGGGLVQPGGSLRLSCAASVDIFTRNIMGWFRQAPGKEREFVAAI TNGGSTKYADSVKGRFTISADNSKNTAYLQMNSLKPEDTAVYYCARQD YYDSSGHIRYWGQGTLVTVSS |

While preferred embodiments of the present disclosure have been shown and described herein, it will be obvious to those skilled in the art that such embodiments are provided by way of example only. Numerous variations, changes, and substitutions will now occur to those skilled in the art without departing from the disclosure. It should be understood that various alternatives to the embodiments of the disclosure described herein may be employed in practicing the disclosure. It is intended that the following claims define the scope of the disclosure and that methods and structures within the scope of these claims and their equivalents be covered thereby.

What is claimed is:

1. An antibody or antibody fragment thereof that binds CD3 epsilon, comprising an amino acid sequence as set forth in any one of SEQ ID NOs: 25-32.

2. The antibody or antibody fragment thereof of claim 1, wherein the antibody is a monoclonal antibody, a bi-specific antibody, a multispecific antibody, a grafted antibody, a humanized antibody, a synthetic antibody, a chimeric antibody, a camelized antibody, a single chain antibody, a single-domain antibody, a diabody, a fragment comprised of only a single monomeric variable domain, an intrabody, or an antigen-binding fragments thereof.

3. The antibody or antibody fragment thereof of claim 1, wherein the antibody or antibody fragment thereof binds to CD3 epsilon with a $K_D$ of less than 75 nM.

4. The antibody or antibody fragment thereof of claim 1, wherein the antibody or antibody fragment thereof binds to CD3 epsilon with a $K_D$ of less than 50 nM.

5. The antibody or antibody fragment thereof of claim 1, wherein the antibody or antibody fragment thereof binds to CD3 epsilon with a $K_D$ of less than 25 nM.

6. The antibody or antibody fragment thereof of claim 1, wherein the antibody or antibody fragment thereof binds to CD3 epsilon with a $K_D$ of less than 10 nM.

7. The antibody or antibody fragment thereof of claim 1, wherein the antibody or antibody fragment thereof is chimeric or humanized.

8. An isolated nucleic acid that encodes the antibody or antibody fragment thereof of claim 1.

* * * * *